United States Patent
Blakely et al.

(10) Patent No.: US 10,436,784 B2
(45) Date of Patent: Oct. 8, 2019

(54) BIODOSIMETRY PANELS AND METHODS

(71) Applicants: Meso Scale Technologies, LLC, Rockville, MD (US); The Henry M. Jackson Foundation for the Advancement of Military Medicine, Inc., Bethesda, MD (US)

(72) Inventors: William F Blakely, Silver Spring, MD (US); Eli N. Glezer, Del Mar, CA (US); John Kenten, Boyds, MD (US); Sudeep Kumar, Gaithersburg, MD (US); Anu Mathew, North Potomac, MD (US); Natalia I. Ossetrova, Silver Spring, MD (US); George Sigal, Rockville, MD (US)

(73) Assignees: Meso Scale Technologies, LLC, Rockville, MD (US); The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 638 days.

(21) Appl. No.: 14/854,514

(22) Filed: Sep. 15, 2015

(65) Prior Publication Data
US 2016/0003822 A1    Jan. 7, 2016

Related U.S. Application Data

(62) Division of application No. 14/348,275, filed as application No. PCT/US2012/057736 on Sep. 28, 2012, now abandoned.
(Continued)

(51) Int. Cl.
*G01N 33/53*    (2006.01)
*G01N 33/569*    (2006.01)
(Continued)

(52) U.S. Cl.
CPC ..... *G01N 33/56972* (2013.01); *G01N 33/566* (2013.01); *G01N 33/6893* (2013.01);
(Continued)

(58) Field of Classification Search
None
See application file for complete search history.

(56) References Cited

U.S. PATENT DOCUMENTS

2006/0205012 A1    9/2006 Debad et al.
2008/0076122 A1*   3/2008 Wyrobek ............. C12Q 1/6883
                                                      435/6.13
(Continued)

FOREIGN PATENT DOCUMENTS

JP           6251856      12/2017
WO    WO 2004/058055 A2   7/2004
WO    WO 2008/140463 A2   11/2008

OTHER PUBLICATIONS

European Communication dated Apr. 12, 2016 received from European Application No. 12 836 460.1.
(Continued)

*Primary Examiner* — Erik B Crawford
(74) *Attorney, Agent, or Firm* — Scully, Scott, Murphy & Presser, P.C.

(57) ABSTRACT

The present invention relates to methods and kits to assess an absorbed dose of ionizing radiation and/or the severity of tissue injury from radiation in a patient. The invention also relates to algorithms used to calculate an absorbed dose of radiation based on biomarker measurements of a plurality of biomarkers that are altered relative to a normal control in the event of radiation exposure.

7 Claims, 49 Drawing Sheets

Related U.S. Application Data

(60) Provisional application No. 61/540,584, filed on Sep. 29, 2011.

(51) Int. Cl.
    *G01N 33/68*     (2006.01)
    *G01N 33/566*     (2006.01)

(52) U.S. Cl.
    CPC .............. *G01N 2333/70535* (2013.01); *G01N 2333/70578* (2013.01); *G01N 2800/40* (2013.01); *G01N 2800/60* (2013.01)

(56) References Cited

U.S. PATENT DOCUMENTS

| | | |
|---|---|---|
| 2008/0176755 A1* | 7/2008 | Amundson ........... B01L 3/5027 506/7 |
| 2009/0289182 A1 | 11/2009 | Pevsner |
| 2010/0144558 A1 | 6/2010 | Zenhausern et al. |
| 2011/0003707 A1 | 1/2011 | Goix et al. |
| 2014/0315742 A1 | 10/2014 | Blakely et al. |

OTHER PUBLICATIONS

Bertho J M et al., "A Rapid Multiparametric Method for Victim Triage in Cases of Accidental Protracted Irradiation or Delayed Analysis", The British Journal of Radiology 82:764-770 (Sep. 2009).
Dainiak N., "Hematologic Consequences of Exposure to Ionizing Radiation", Experimental Hematology 30:513-528 (2002).
Dainiak N. et al., "The Hematologist and Radiation Casualties", Hematology 473-496 (2003).
Goans R.E. et al., "Early Dose Assessment Following Severe Radiation Accidents", Health Physics 72(4):513-518 (Apr. 1997).
Koc M. et al., "Levels of Some Acute-Phase Proteins in the Serum of Patients With Cancer During Radiotherapy", Biol. Pharm. Bull. 26(10):1494-1497 (2003).
Marchetti F. et al., "Candidate Protein Biodosimeters of Human Exposure to Ionizing Radiation", Int. J. Radiat. Biol. 82(9):605-639 (Sep. 2006).
Metcalf D., "The Granulocyte-Macrophage Colony-Stimulating Factors", Science 229:16-22 (Jul. 5, 1985).
Monroy R.L. et al., "The Effect of Recombinant GM-CSF on the Recovery of Monkeys Transplanted With Autologous Bone Marrow", Blood 70(5):1696-1699 (Nov. 1987).
Ossetrova N.I. et al., "Multiple Blood-Proteins Approach for Early-Response Exposure Assessment Using an In Vivo Murine Radiation Model", Int. J. Radiat. Biol. 85(10):837-850 (Oct. 2009).
Rawstron A.C. et al., "Quantitation of Minimal Disease Levels in Chronic Lymphocytic Leukemia Using a Sensitive Flow Cytometric Assay Improves the Prediction of Outcome and Can be Used to Optimize Therapy", Blood 98 (1):29-35 (Jul. 1, 2001).
Redon C.E. et al., "Recent Developments in the Use of y-H2AX as a Quantitative DNA Double-Strand Break Biomarker", Aging 3(2):168-174 (Feb. 2011).
Redon C.E. et al., "The Use of Gamma-H2AX as a Biodosimeter for Total-Body Radiation Exposure in Non-Human Primates", PLoS One 5(11):e15544 (8 pages total) (Nov. 2010).
Rothkamm K. et al., "y-H2AX as Protein Biomarker for Radiation Exposure", Ann Ist Super Sanita 45(3):265-271 (2009).
Taneja N. et al., "Histone H2AX Phosphorylation as a Predictor of Radiosensitivity and Target for Radiotherapy", The Journal of Biological Chemistry 279(3):2273-2280 (Jan. 2004).
Welte K. et al., "Recombinant Human Granulocyte Colony-Stimulating Factor-Effects on Hematopoiesis in Normal and Cyclophosphamide-Treated Primates", J. Exp. Med. 165:941-948 (Apr. 1987).
Wilson J.W. et al., "Radiation-Induced p53 and p21WAF-1/CIP1 Expression in the Murine Intestinal Epithelium", American Journal of Pathology 153(3):899-909 (Sep. 1998).
Bd Biosciences, "CD Marker Handbook-Human Mouse Welcome to More Choice Human and Mouse CD Marker Handbook", pp. 1-47, retrieved from the Internet: URL:https://www.bdbiosciences.com/documents/cd_marker_handbook.pdf (Jan. 1, 2010).
International Search Report dated Feb. 18, 2013 received from Application No. PCT/US2012/057736.
Extended Supplementary European Search Report dated Apr. 2, 2015 received from Application No. 12836460.1.
Japanese Notice of Reasons for Rejection dated Dec. 20, 2016 received in Japanese Patent Application No. 2014-533351, together with an English-language translation.
Japanese Notice of Reasons for Rejection dated Feb. 6, 2018 received from Japanese Patent Application No. 2017-054050, together with an English-language translation.
Yuan M. et al., "Leukocytes are Primed in Peripheral Blood for Activation During Term and Preterm Labour", Molecular Human Reproduction 15(11):713-724 (Jul. 23, 2009).
European Partial Search Report dated May 28, 2019 received in European Application No. 19 15 3115.1.
Sandgren D.J. et al., "Biodosimetry Assessment Tool (BAT) Software-Dose Prediction Algorithms", Health Physics 99:S171-S183 (Nov. 1, 2010).
European Extended Search Report dated Aug. 23, 2019 received in European Patent Application No. 19 15 3115.1.

* cited by examiner

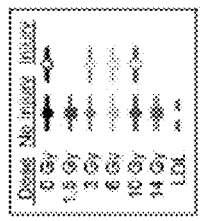
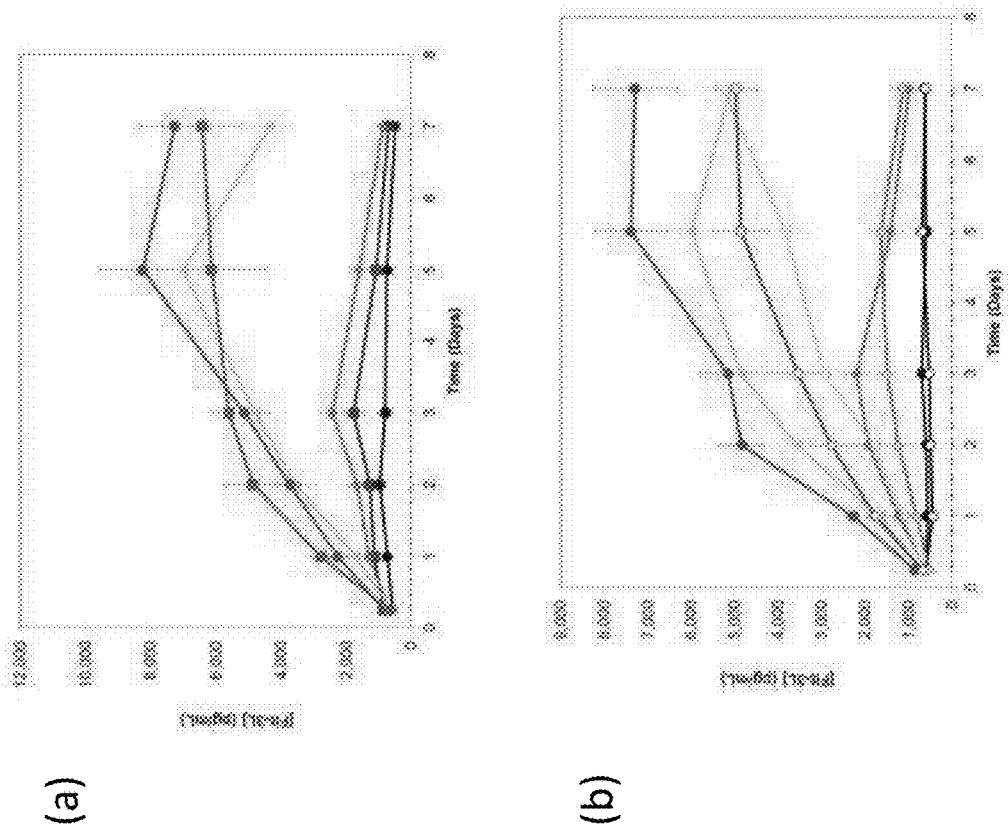
Figs. 1(a)-(b)

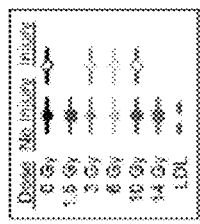
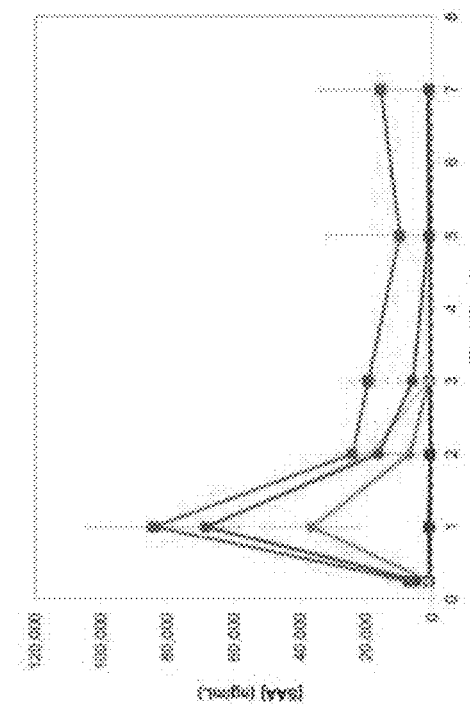
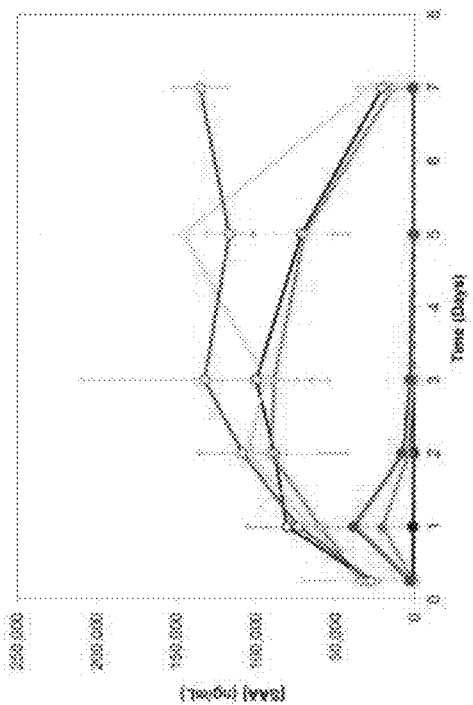
Figs. 2(a)-(b)

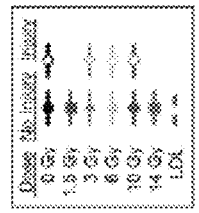
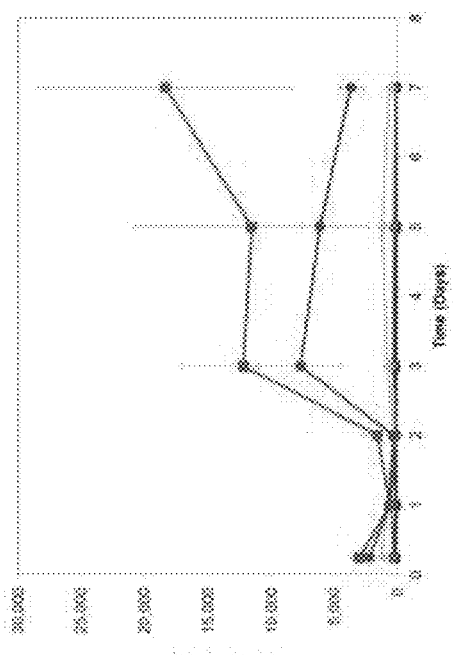
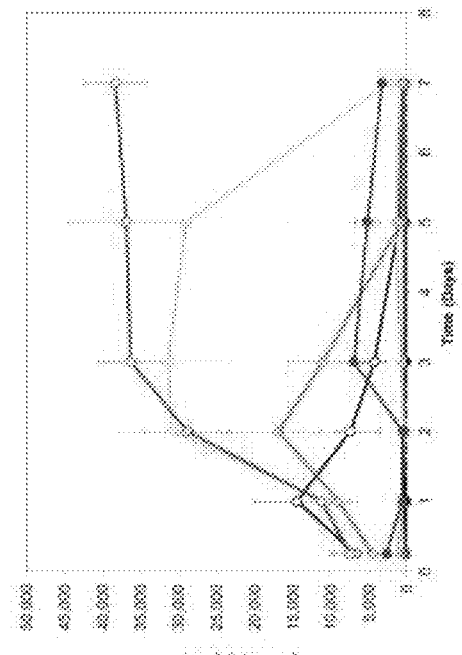
Figs. 3(a)-(b)

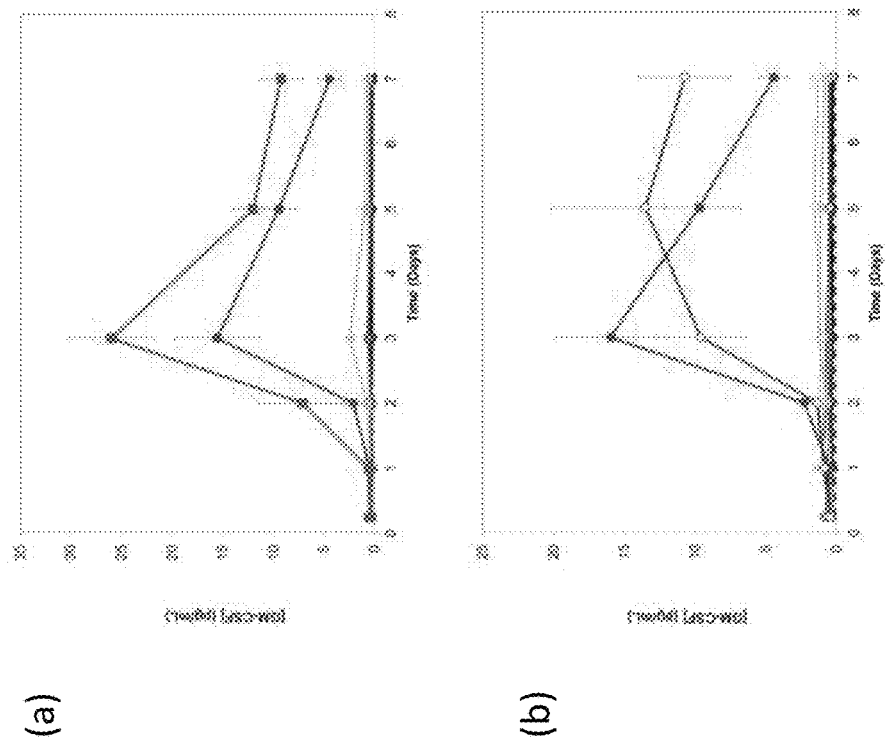
Figs. 4(a)-(b)

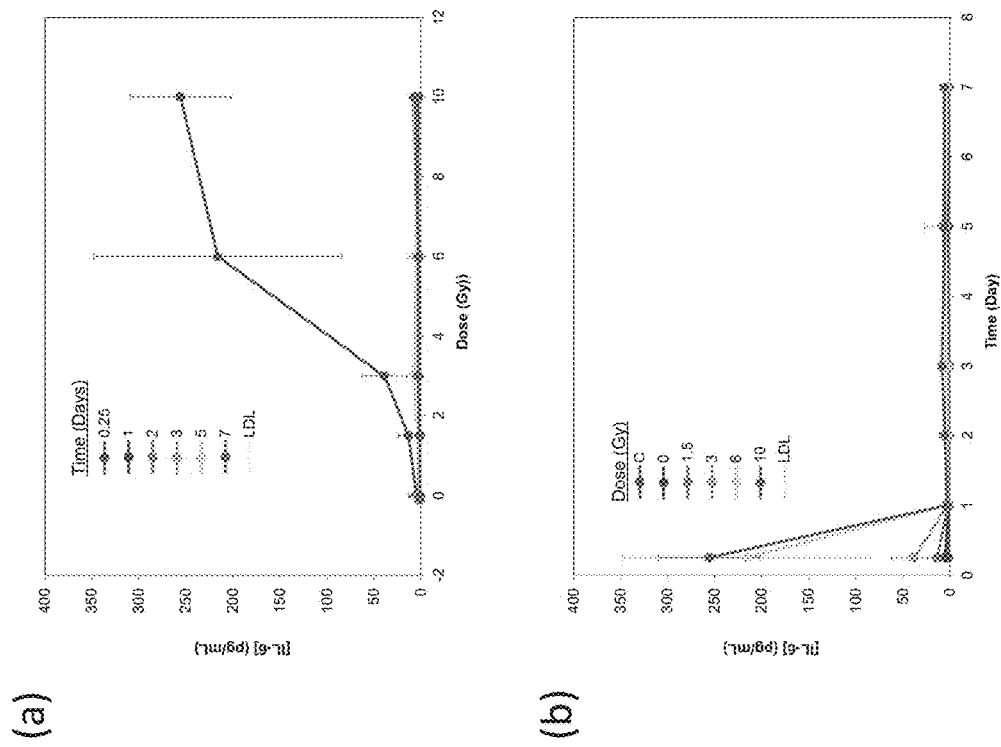
Figs. 5(a)-(b)

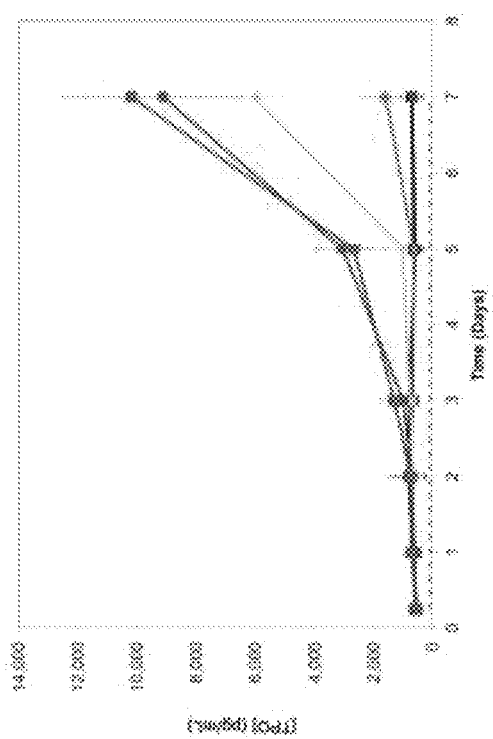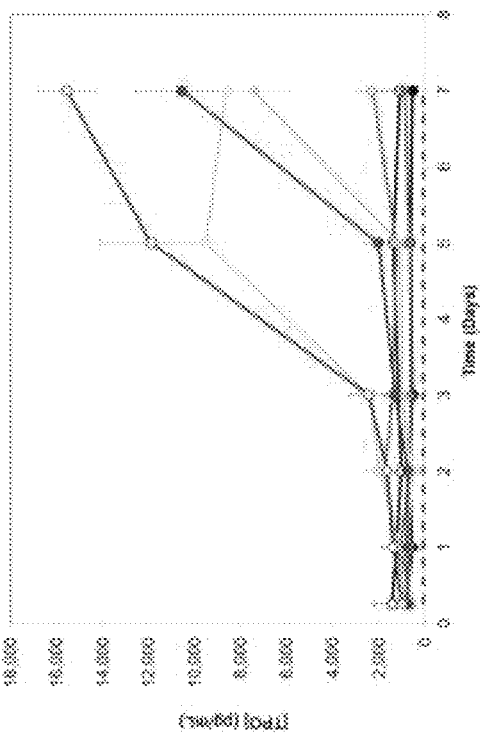
Figs. 6(a)-(b)

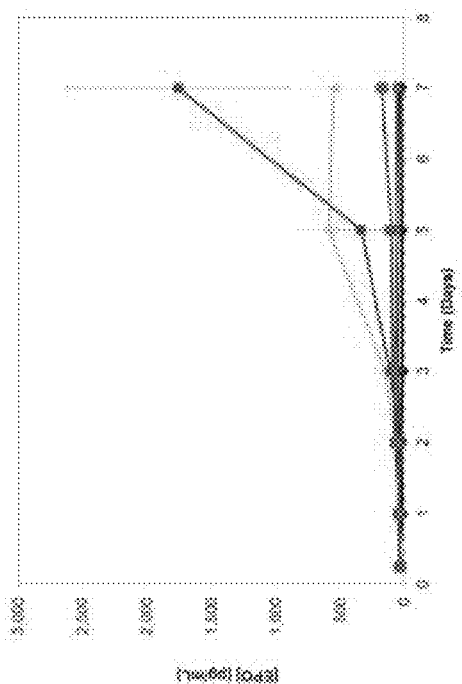
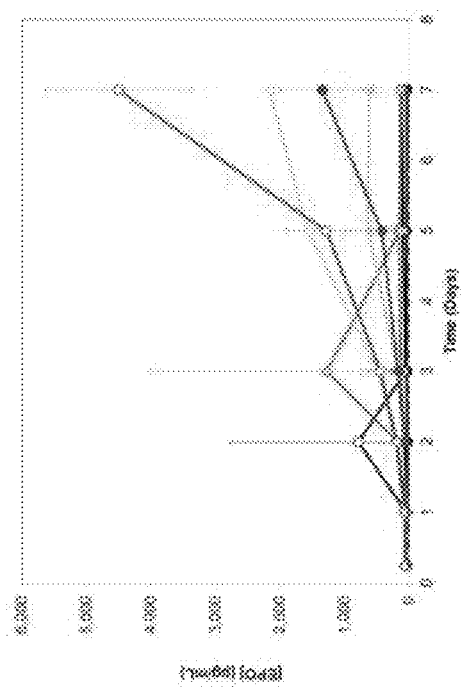
Figs. 7(a)-(b)

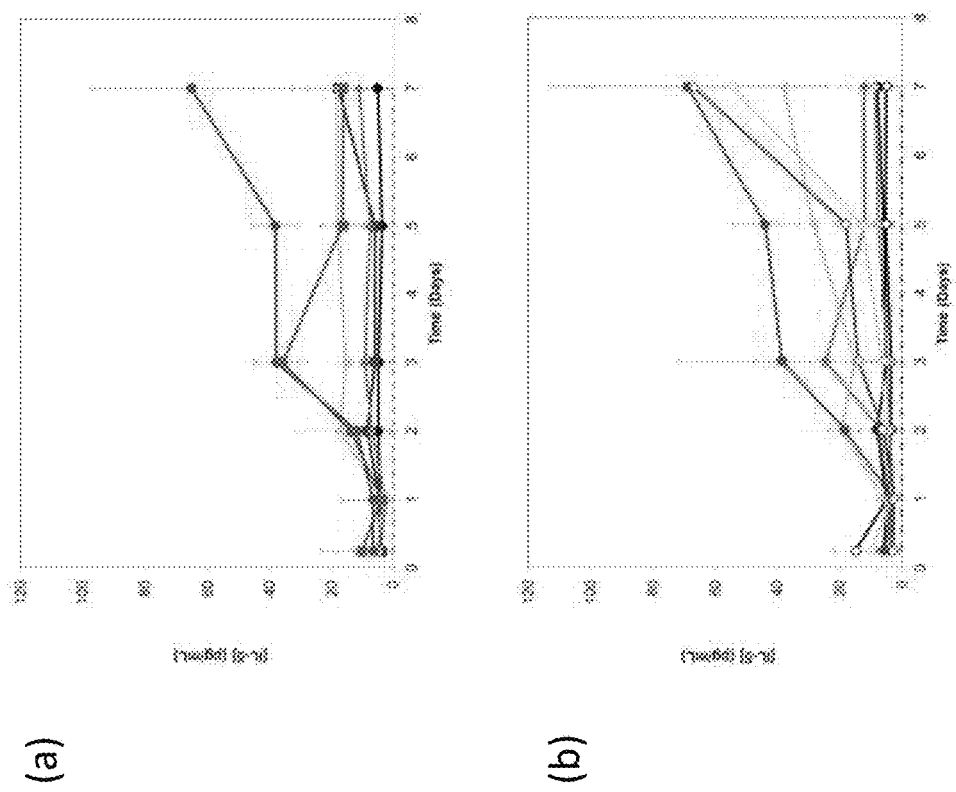
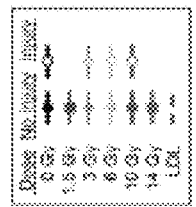
Figs. 8(a)-(b)

Table 16
| IL-10 | 1.5 Gy | 3 Gy | 6 Gy | 10 Gy |
|---|---|---|---|---|
| 6 hrs | 0.421 | 0.050 | 0.002 | 0.012 |
| 1 day | 0.817 | 0.897 | 0.691 | 0.347 |
| 2 day | 0.670 | 0.515 | 0.718 | 0.909 |
| 3 day | 0.133 | 0.344 | 0.406 | 0.061 |
| 5 day | 0.199 | 0.841 | 0.075 | 0.015 |
| 7 day | 0.932 | 0.657 | 0.906 | 0.973 |
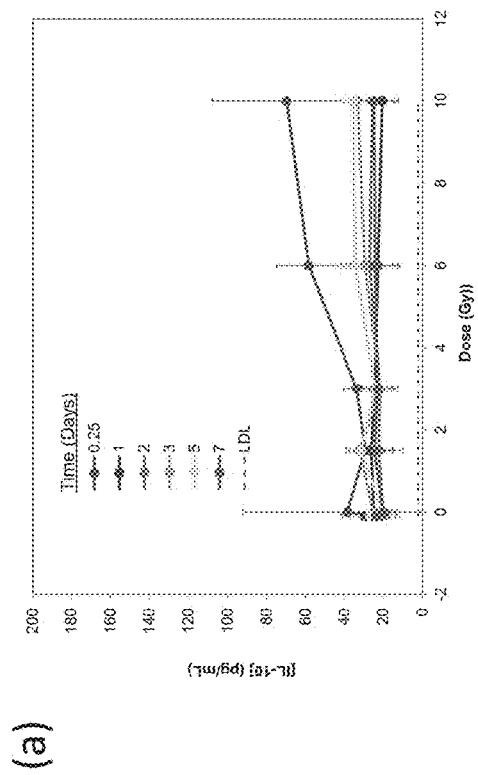
(a)
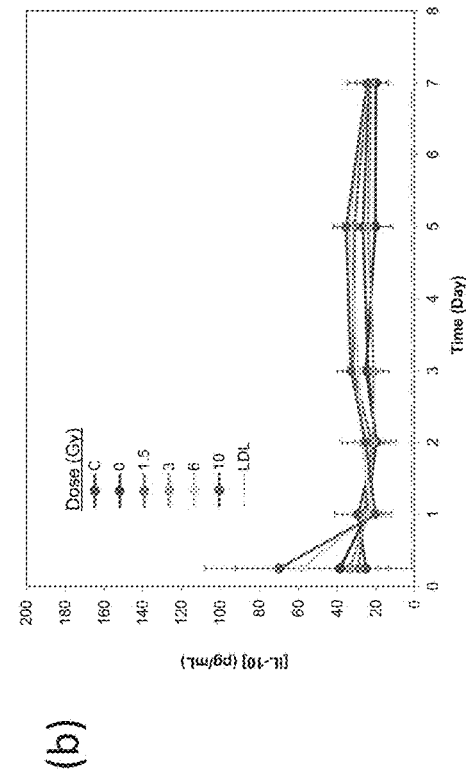
(b)
Figs. 9(a)-(b)

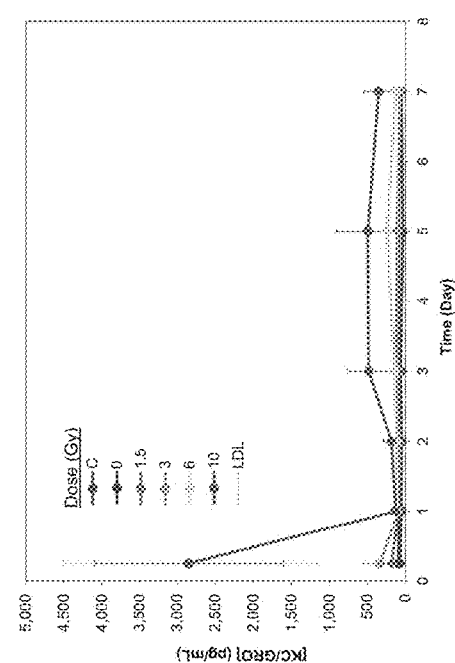
Table 17
| KC/GRO | 1.5 Gy | 3 Gy | 6 Gy | 10 Gy |
|---|---|---|---|---|
| 6 hrs | 0.063 | 0.025 | 0.010 | 0.042 |
| 1 day | 0.655 | 0.853 | 0.374 | 0.040 |
| 2 day | 0.991 | 0.488 | 0.256 | 0.005 |
| 3 day | 0.930 | 0.140 | 0.082 | 0.005 |
| 5 day | 0.564 | 0.447 | 0.153 | 0.029 |
| 7 day | 0.170 | 0.261 | 0.070 | 0.007 |
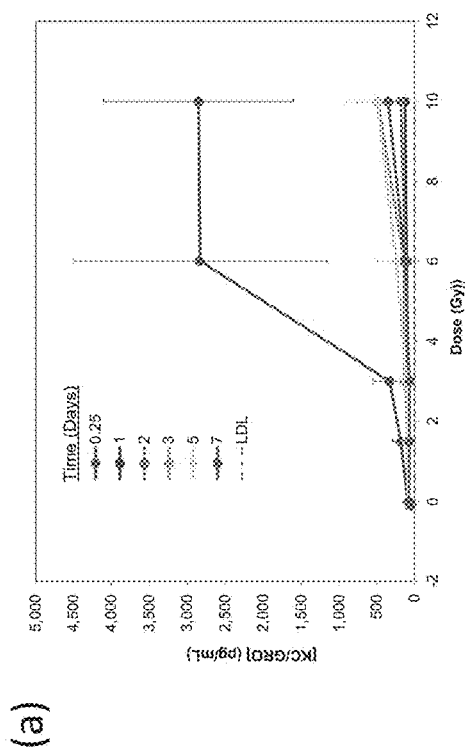
Figs. 10(a)-(b)

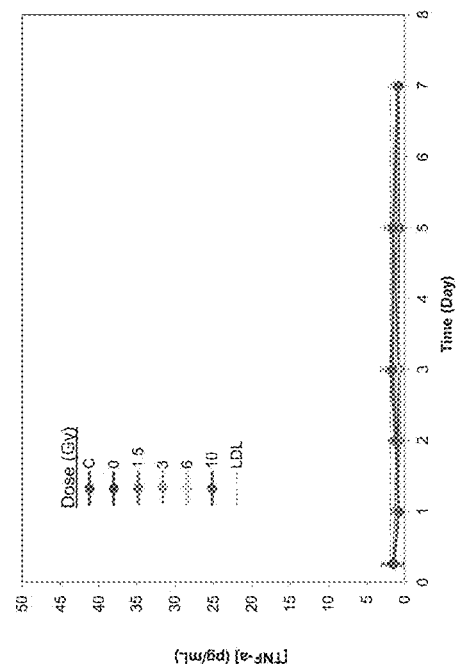
Table 18
| TNFa | 1.5 Gy | 3 Gy | 6 Gy | 10 Gy |
|---|---|---|---|---|
| 6 hrs | 0.294 | 0.177 | 0.296 | 0.129 |
| 1 day | 0.420 | 0.970 | 0.871 | 0.592 |
| 2 day | 0.483 | 0.100 | 0.395 | 0.460 |
| 3 day | 0.101 | 0.046 | 0.534 | 0.080 |
| 5 day | 0.985 | 0.765 | 0.091 | 0.184 |
| 7 day | 0.592 | 0.887 | 0.901 | 0.882 |
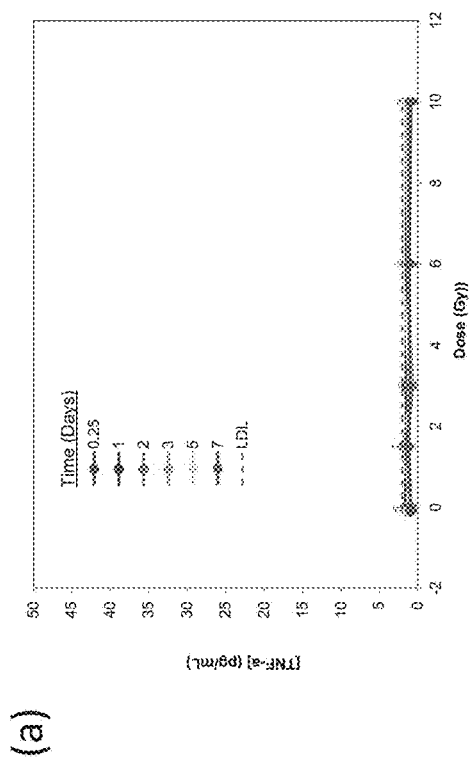
Figs. 11(a)-(b)

Table 19
| pH2AX | 1.5 Gy | 3 Gy | 6 Gy | 10 Gy |
|---|---|---|---|---|
| 6 hrs | 0.442 | 0.024 | 0.000 | 0.000 |
| 1 day | 0.533 | 0.009 | 0.011 | |
| 2 day | 0.155 | 0.016 | 0.412 | 0.978 |
| 3 day | 0.295 | 0.215 | 0.397 | 0.535 |
| 5 day | 0.209 | 0.684 | 0.024 | 0.019 |
| 7 day | 0.991 | 0.328 | 0.272 | |
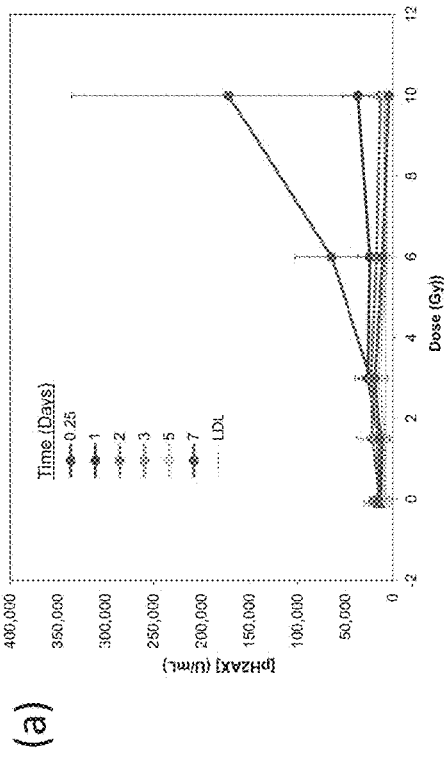
(a)
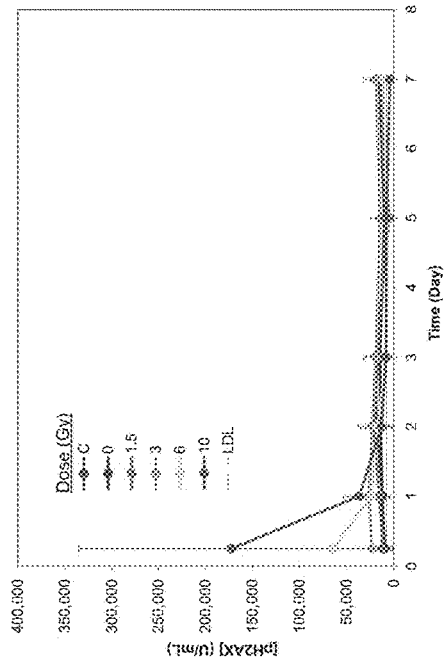
(b)
Figs. 12(a)-(b)

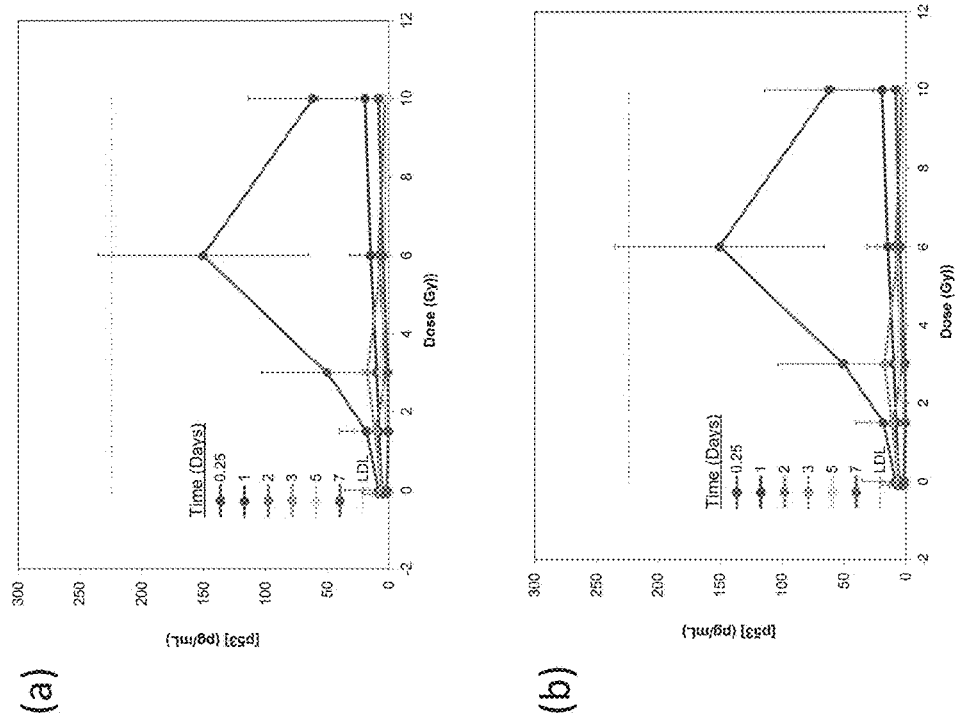
Figs. 13(a)-(b)

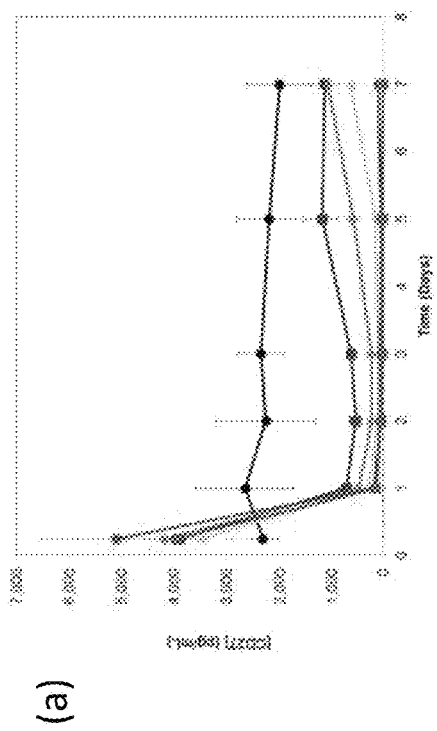
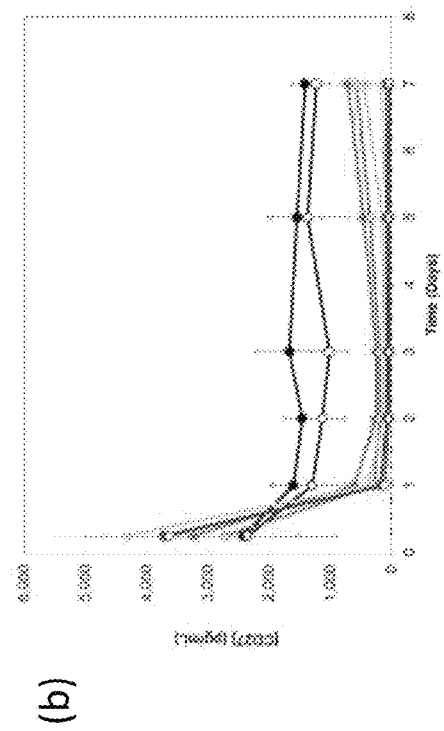
Figs. 14(a)-(b)

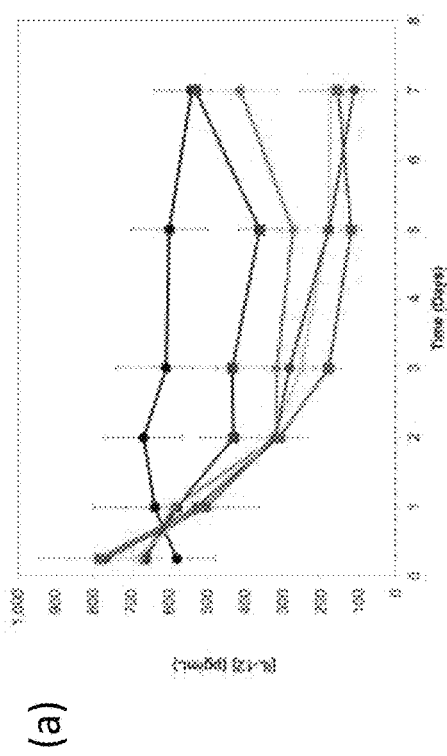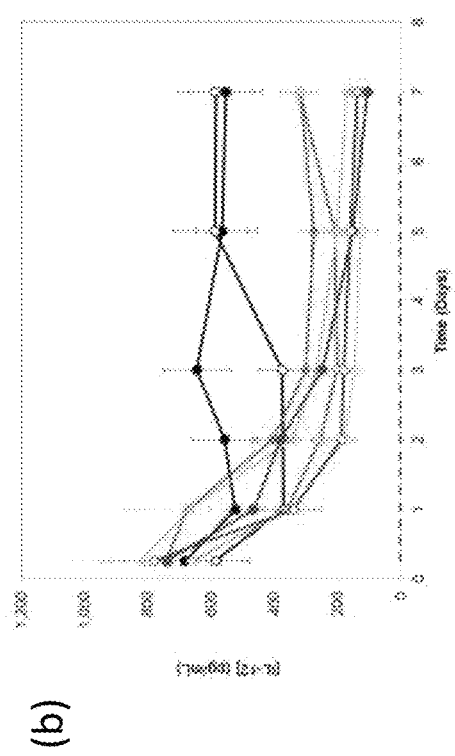
Figs. 15(a)-(b)

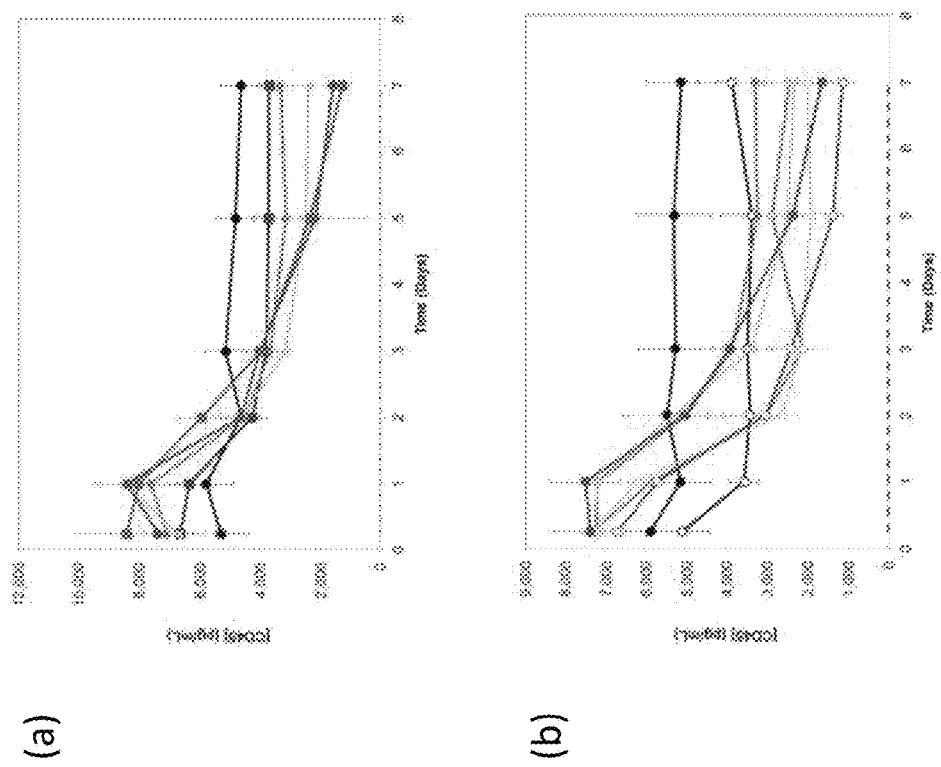
Figs. 16(a)-(b)

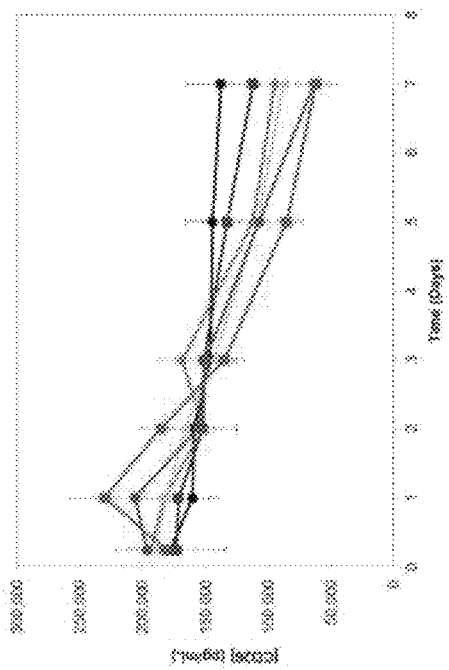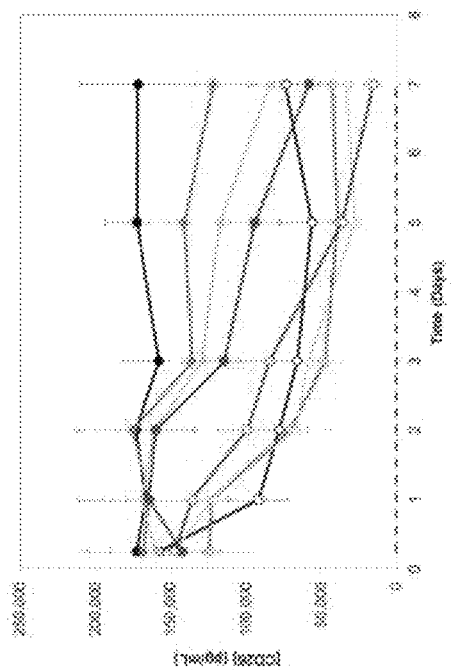
Figs. 17(a)-(b)

(a)

(b)

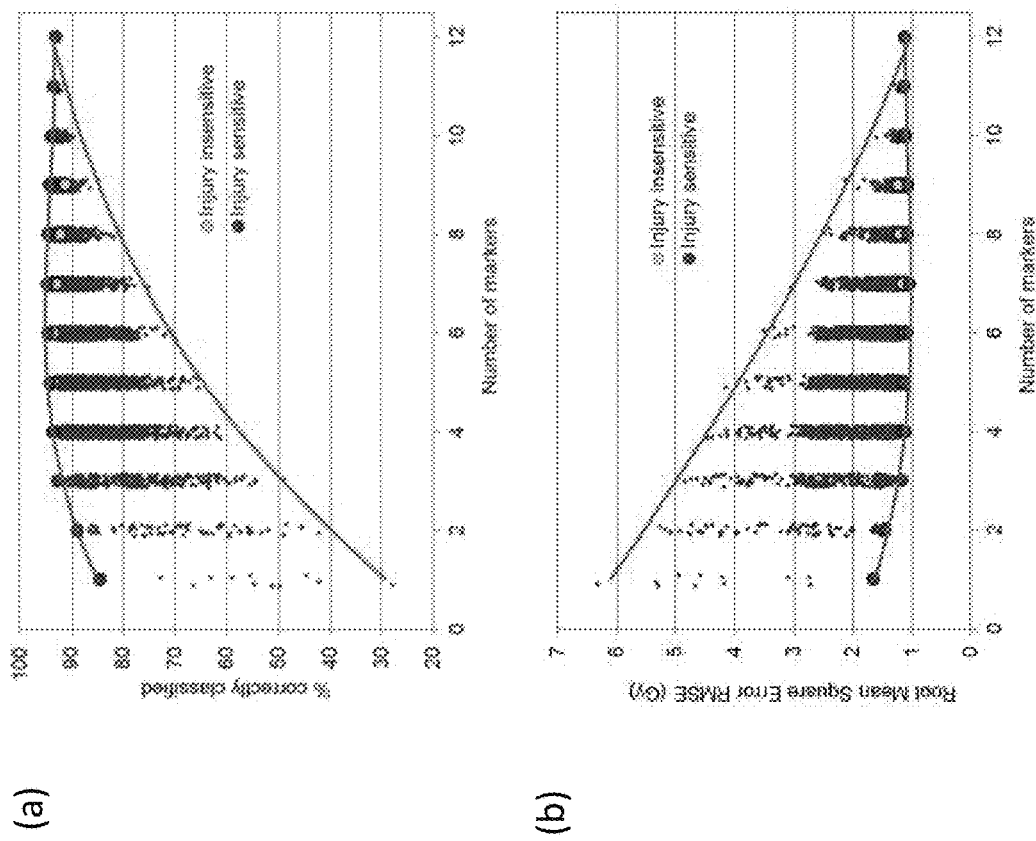
Figs. 20(a)-(b)

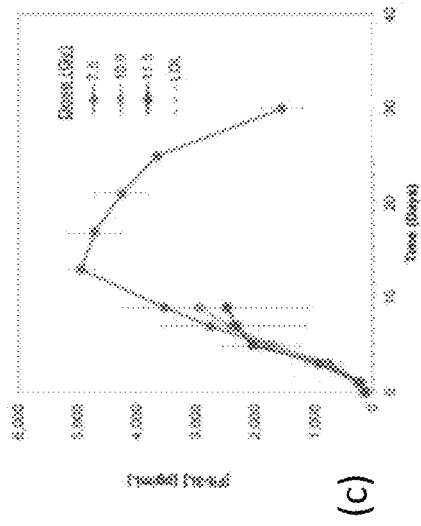
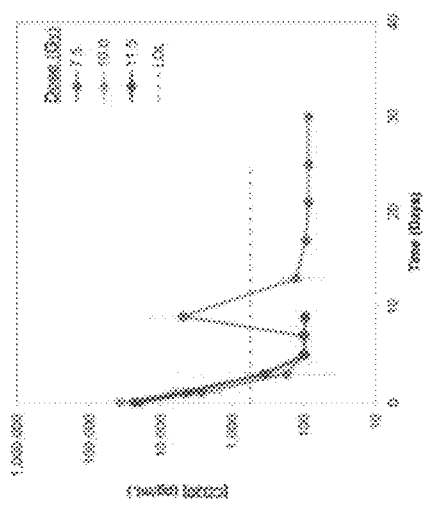
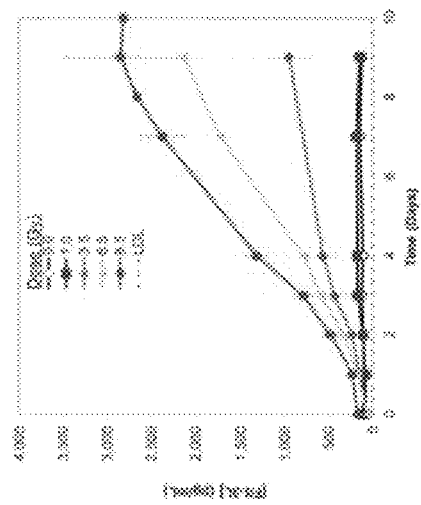
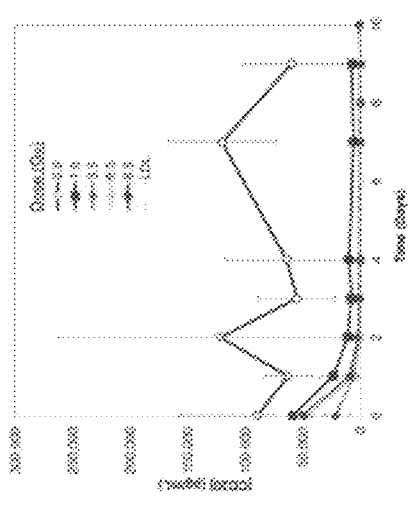
Figs. 24(a-d)

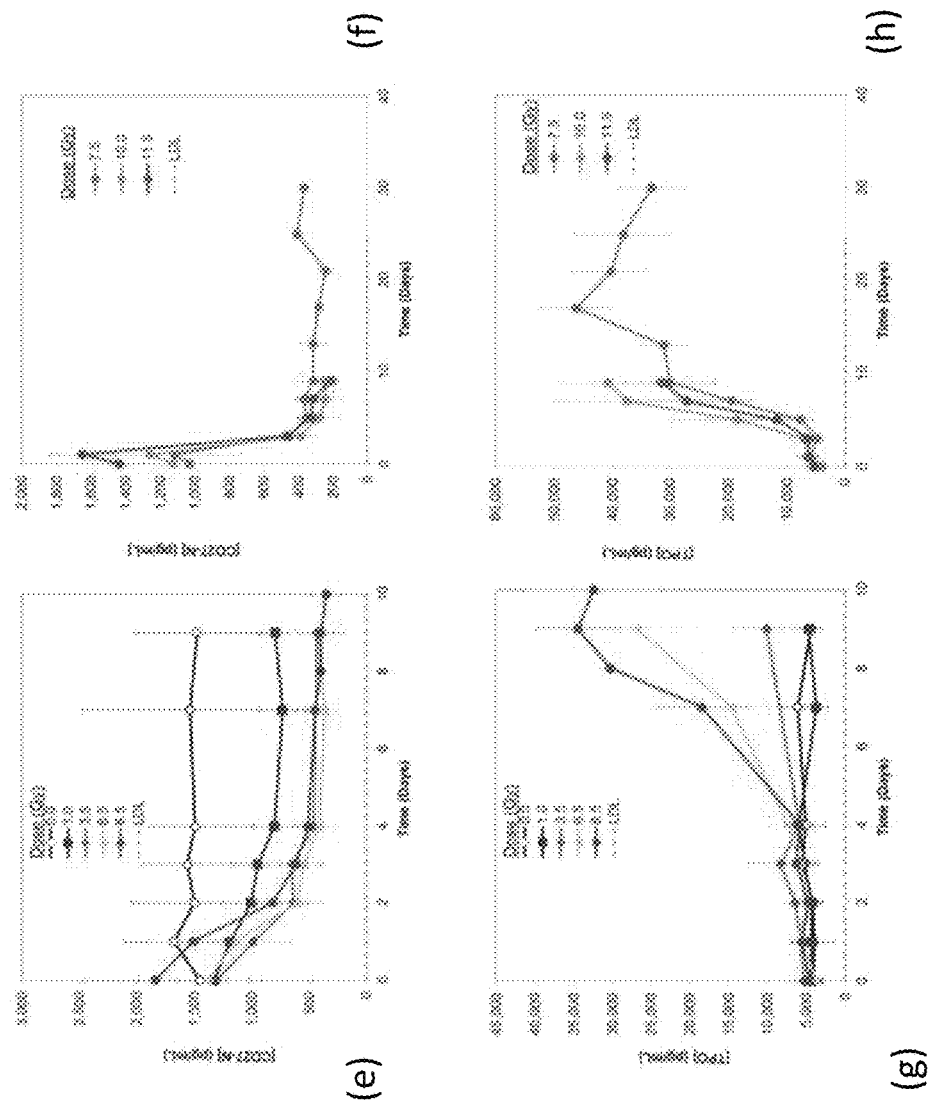
Figs. 24(e-h)

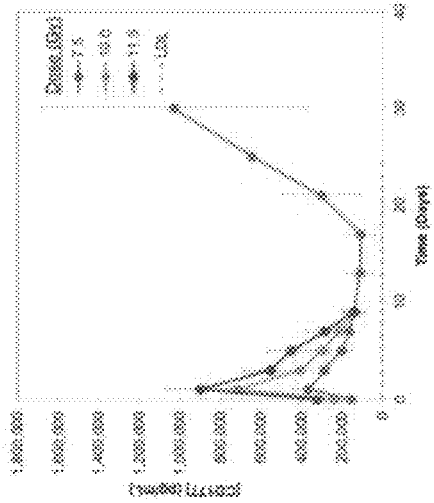
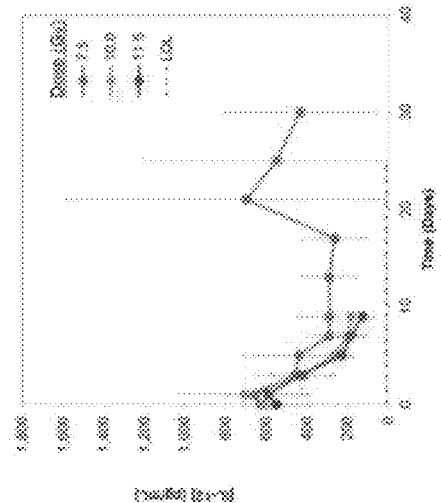
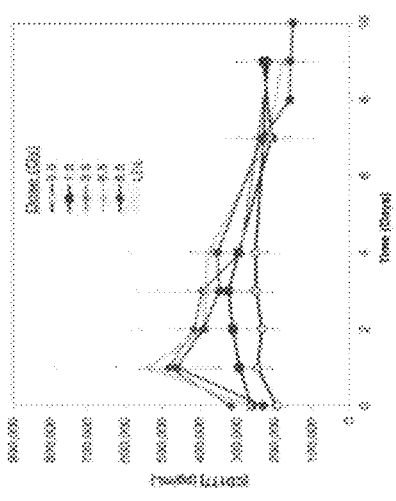
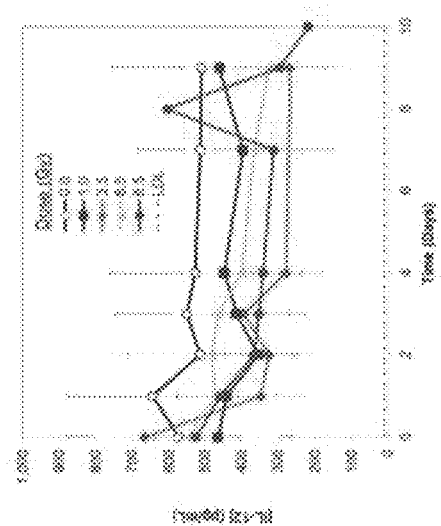
Figs. 24(i-l)

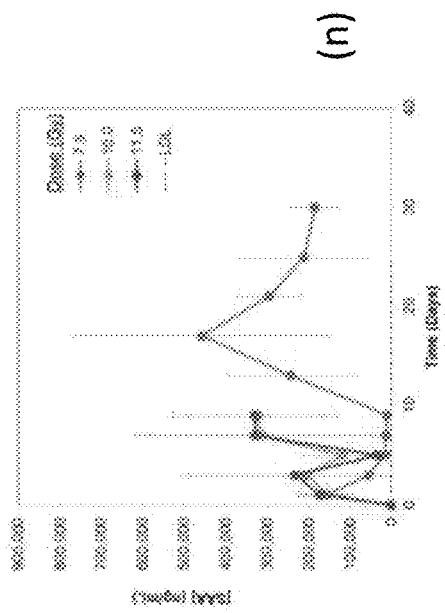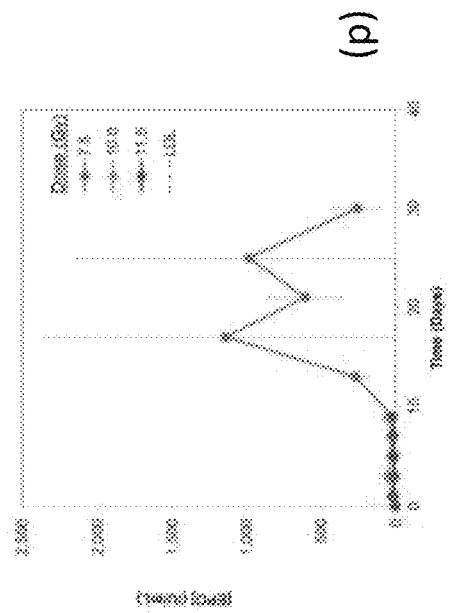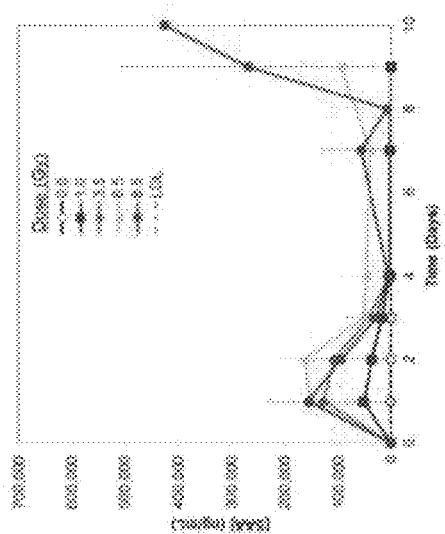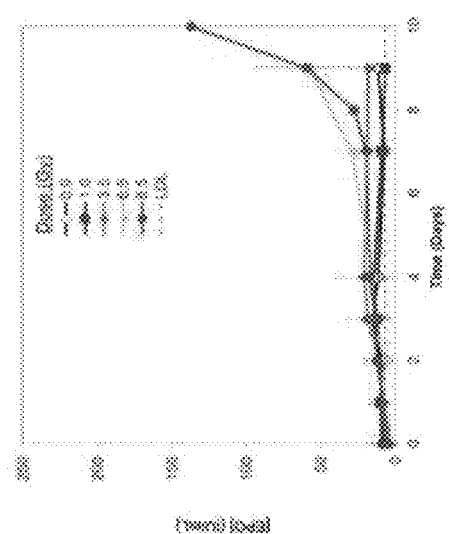
Figs. 24(m-p)

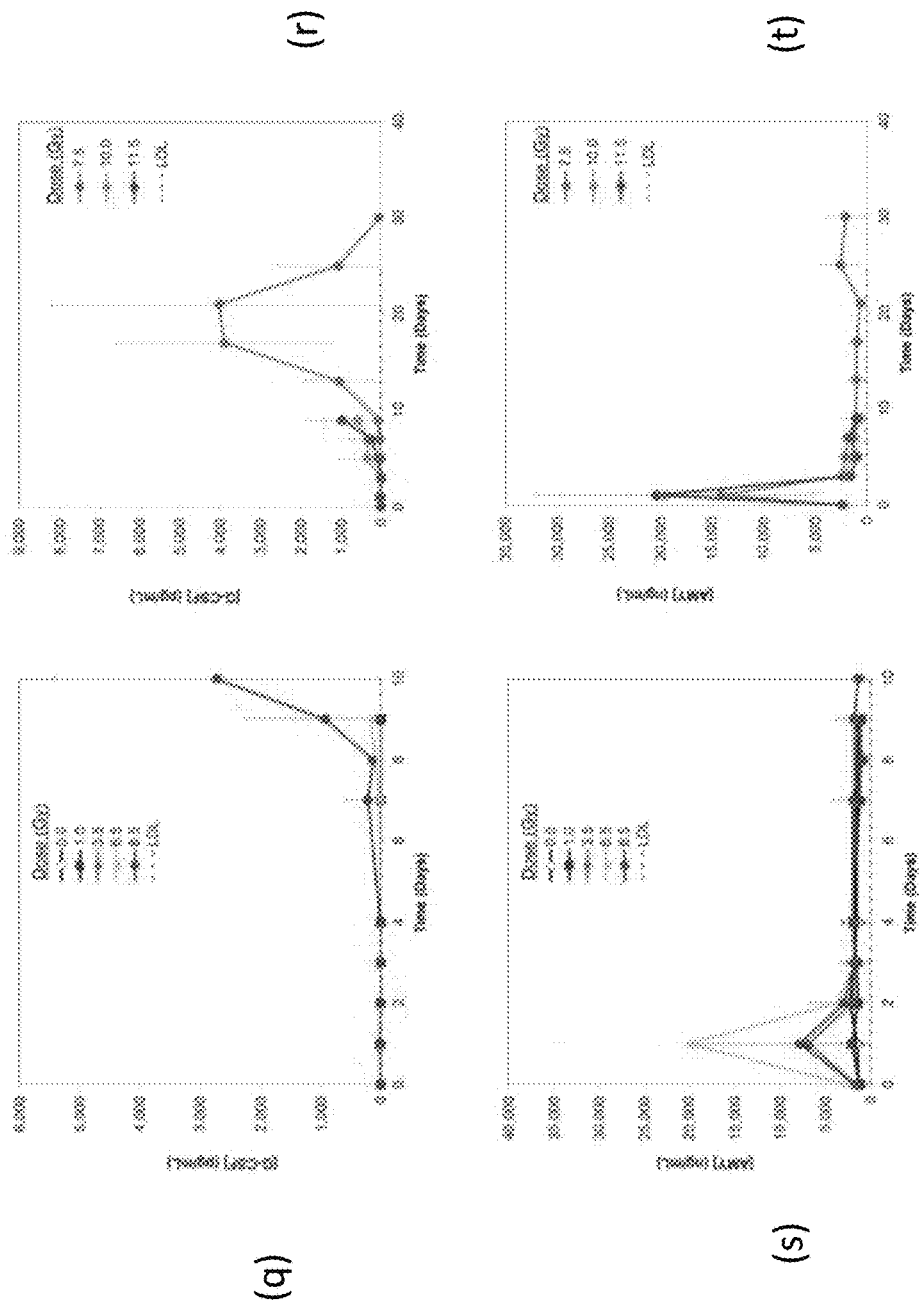
Figs. 24 (q-t)

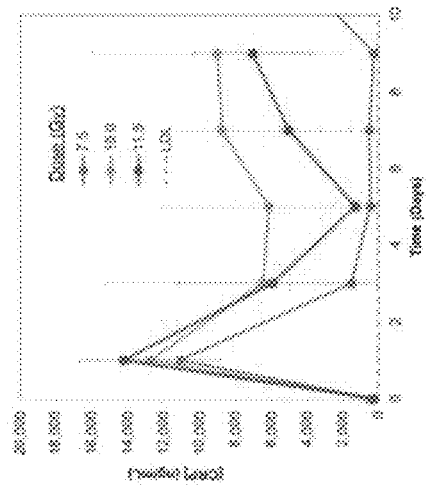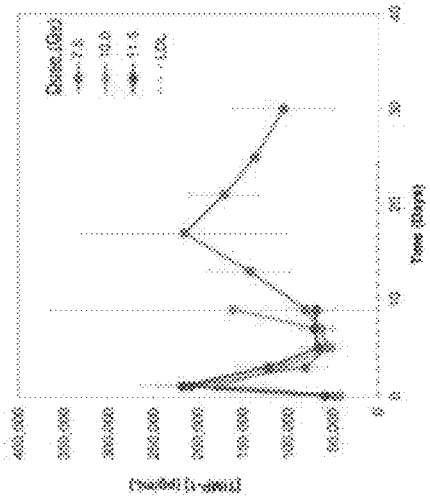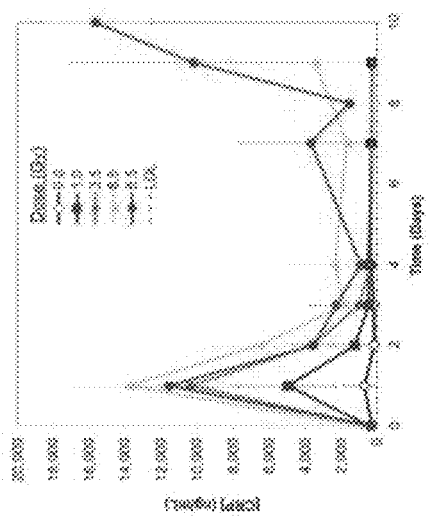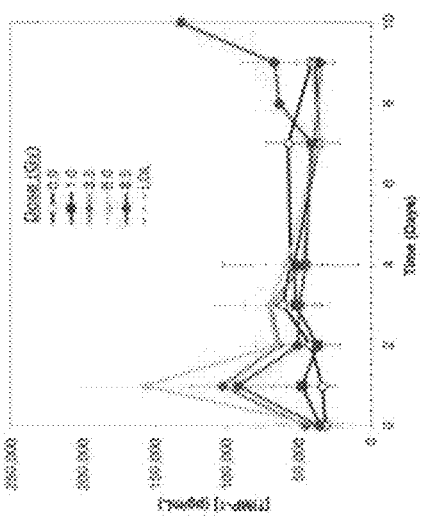
Figs. 24(u-x)

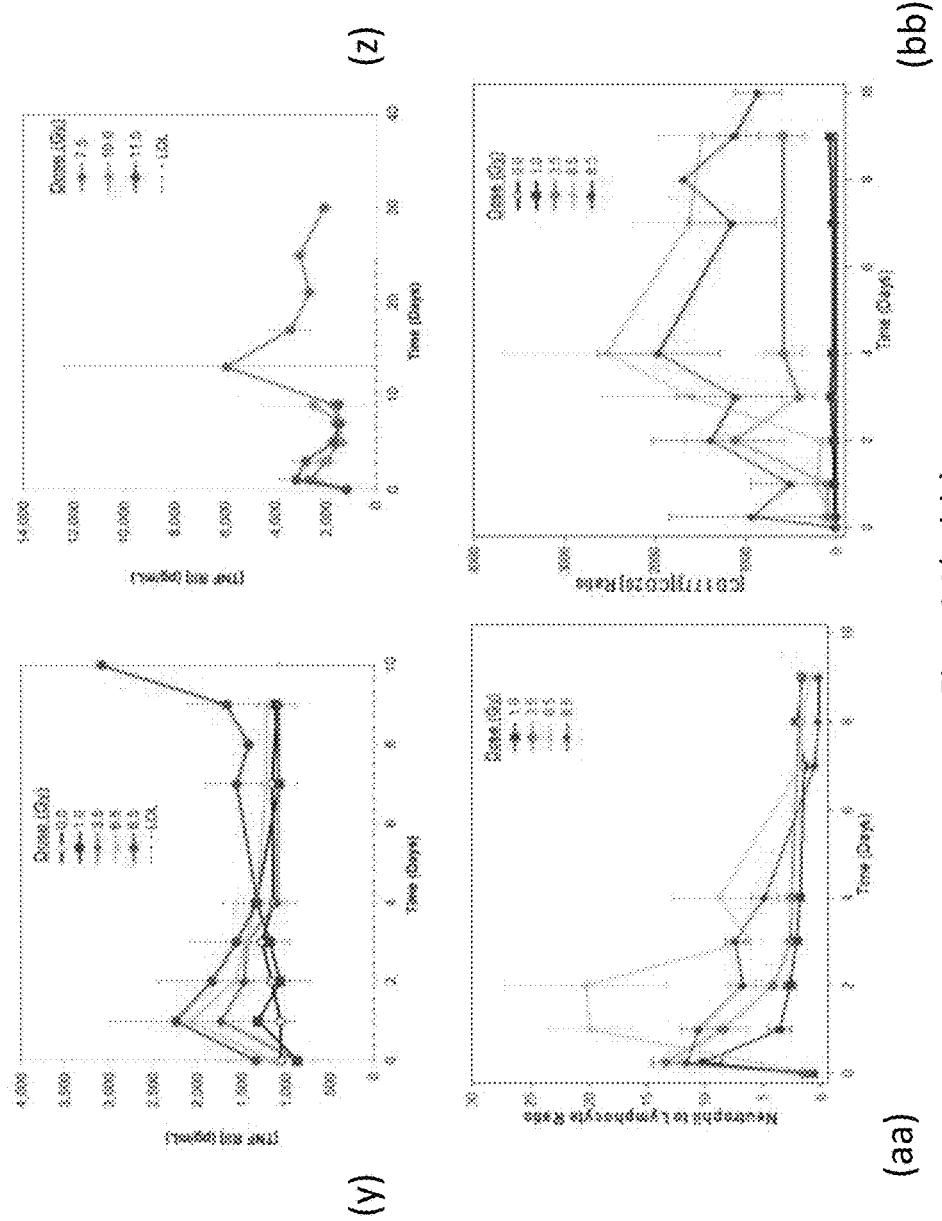
Figs. 24(y-bb)

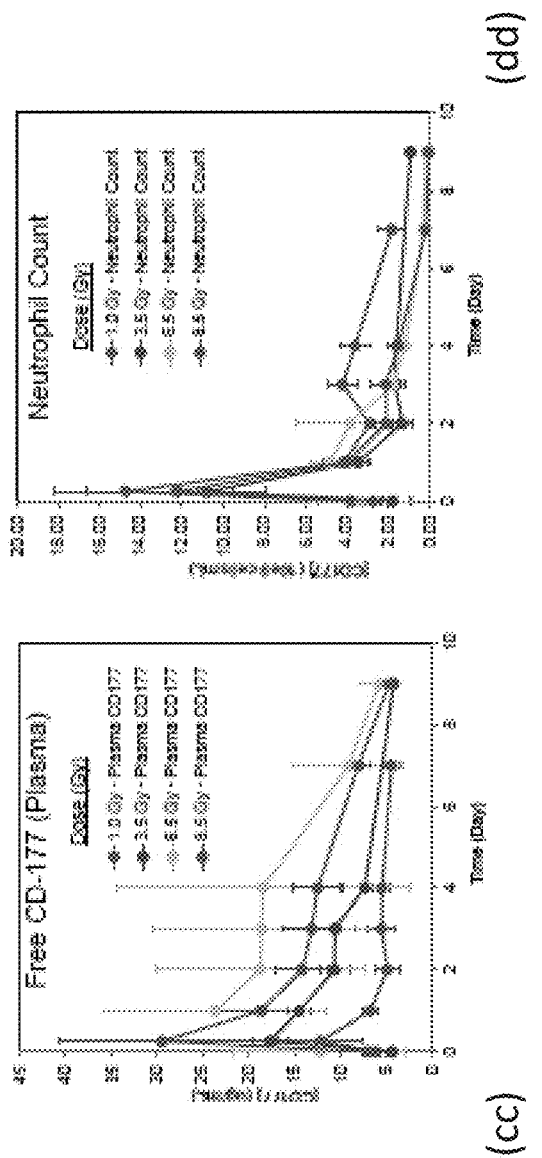
Figs. 24(cc-dd)

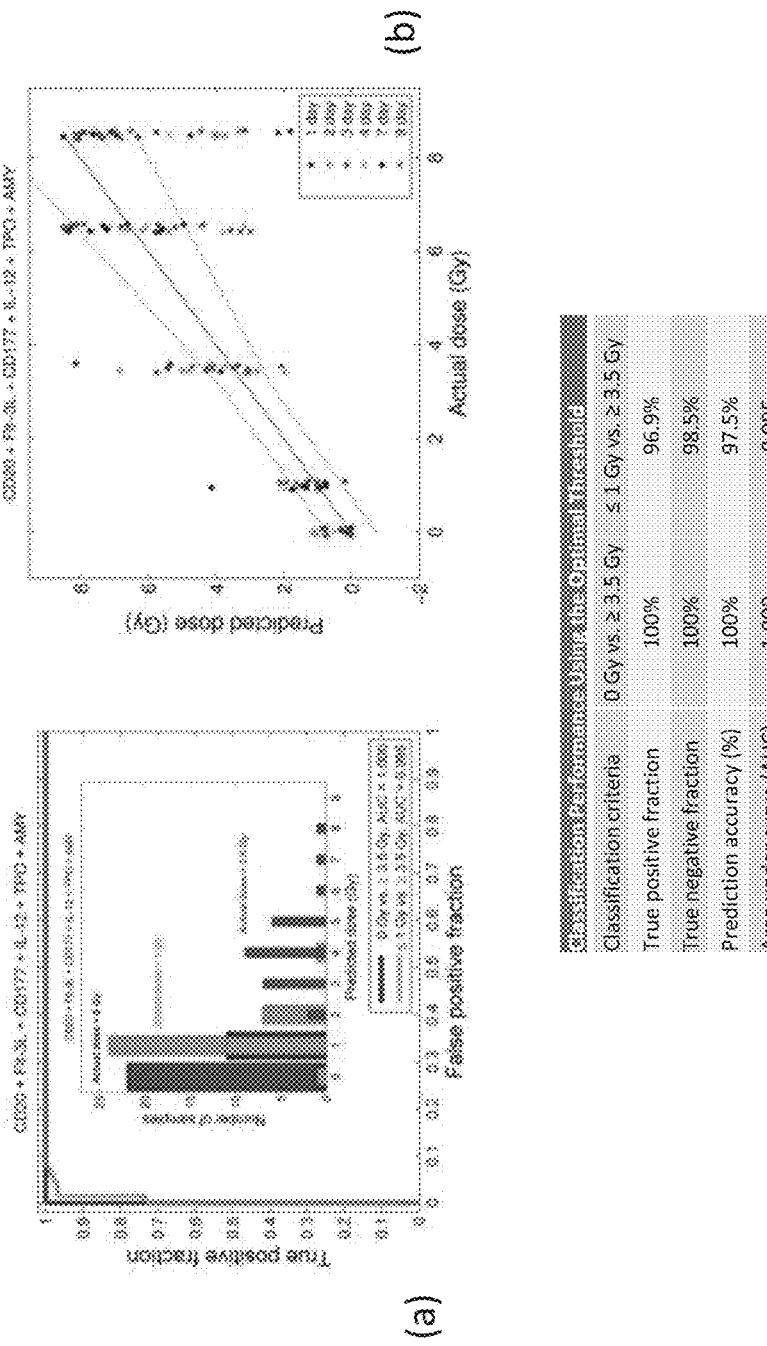
Figs. 25(a-b)

BIODOSIMETRY PANELS AND METHODS

CROSS REFERENCE TO RELATED APPLICATIONS

The present application is a divisional of U.S. patent application Ser. No. 14/348,275, filed Mar. 28, 2014, which is a 371 of International Application having Serial No. PCT/US2012/057736, filed Sep. 28, 2012, which claims benefit of U.S. Provisional Application No. 61/540,584 filed on Sep. 29, 2011, the contents of all of which are incorporated herein by reference.

STATEMENT REGARDING FEDERALLY-SPONSORED RESEARCH

This invention was made with federal support under HHSO100201000009C awarded by the Department of Health and Human Services. The U.S. government has certain rights in the invention.

FIELD OF THE INVENTION

This application relates to assay methods, modules and kits for conducting diagnostic assays useful in the detection of radiation exposure and the severity of tissue injury to radiation.

BACKGROUND OF THE INVENTION

In the aftermath of an incident in which a significant number of civilians are exposed to radiation or radioactive materials, health authorities will need to be able to rapidly identify individuals who have been exposed to life-threatening significant doses of radiation. The deadly effects of ionizing radiation (IR) are wide-ranging and include systemic and organ-specific damage. Acute effects of high-dose ionizing radiation (>2 Gy) include depletion of specific types of peripheral blood cells, immune suppression, mucosal damage, and potential injury to other sites such as bone and bone marrow niche cells, gastrointestinal system, lungs, kidneys, and the central nervous system. In addition, exposures to low or moderate doses (1-3 Gy) of ionizing radiation can result in increased mortality if accompanied by physical injuries, opportunistic infections, and/or hemorrhage. Long-term effects include dysfunction or fibrosis in a wide range of organs and tissues, cataracts, and, ultimately, a higher risk of cancer. In many cases, the effects of radiation exposure can be mitigated by early triage and treatment.

Although radioactive material can be detected with instruments, assessment of the radiation dose or injury that a person has already received is more difficult. Because current and foreseeable medical countermeasures for radiation injuries are often expensive, labor-intensive and time-consuming to administer (and monitor), have limited availability, and are occasionally associated with serious toxicities, they should only be administered to persons who will likely benefit from their use. Fast, accurate radiation dose and tissue injury assessment could greatly facilitate identification of exposed people who could benefit from early medical intervention.

No rapid diagnostic exists that can reliably discriminate levels of IR exposure based on samples collected at a single time point. The complete blood count, particularly the lymphocyte count, is useful, but optimally requires at least two samples spaced hours to days apart to estimate dose. The diagnostic "gold standard" in the field of radiation biodosimetry, the dicentric chromosome assay, is labor-intensive and slow, and its use in mass-casualty situations would be problematic.

Therefore, there is a need for sensitive and specific biodosimetry dose assessment tools that can be used to identify patients requiring urgent medical attention, improve risk assessment for the delayed or late effects of radiation exposure, improve patient tracking efficiency for repeated observation or therapeutic administration, and play a role in monitoring therapy and long-term follow-up. Such tools will also fill an important need for monitoring radiation received during medical care, for example, radiation received from medical imaging devices, radiation received as a medical therapy (for example to treat cancer), or radiation received in preparation for stem-cell transplants. The tools would provide the capability to detect individuals accidentally overexposed, to select individuals and optimize the schedule of countermeasure doses used in treatment as well as to monitor their efficacy for specific individuals.

SUMMARY OF THE INVENTION

The present invention provides a biodosimetry assay panel and methods to measure multiple radiation-sensitive protein biomarkers to assess radiation dose and tissue injury. The methods of the present invention can be used to triage and guide the treatment of individuals exposed to ionizing radiation after a major radiological or nuclear event. The tools can also be used to guide treatment of individuals exposed to ionizing radiation during medical treatment or as a result of an accidental exposure.

Accordingly, the present invention provides a multiplexed assay kit used to assess an absorbed dose of ionizing radiation or radiation-induced tissue injury in a patient sample, wherein the kit is configured to measure the level of a plurality of biomarkers in the sample and the plurality of biomarkers includes: (a) a DNA-damage biomarker; (b) an inflammatory-response biomarker; (c) a tissue-damage biomarker; (d) a tissue-damage repair biomarker; (e) a hematology-surrogate marker; and (f) combinations thereof. Also contemplated is a device capable of receiving a kit such as this or a component thereof to measure level of said plurality of biomarkers, said device operatively associated with a computer system, said computer system having stored thereon a computer program which, when executed by said computer system, causes the computer program to perform a method comprising correlating the level of said plurality of biomarkers present in the sample with the dose of radiation absorbed by the patient.

Also provided is a multiplexed assay kit used to assess an absorbed dose of ionizing radiation in a patient sample, said kit is configured to measure the level of a plurality of biomarkers in said sample, said plurality of biomarkers comprising (i) one or more biomarkers including Flt-3L, G-CSF, GM-CSF, EPO, CD27, CD45, SAA, CD26, IL-12, TPO, and combinations thereof; and (ii) an additional biomarker including: (a) a DNA-damage biomarker; (b) an inflammatory-response biomarker; (c) a tissue-damage biomarker; (d) a tissue-damage repair biomarker; (e) a hematology-surrogate marker; and (f) combinations thereof. In a preferred embodiment, the plurality of biomarkers comprises Flt-3L, GM-CSF, SAA, TPO, CD27, CD45, CD26, and IL-12.

The invention also includes a method of assessing an absorbed dose of ionizing radiation in a patient sample, said method comprising (a) measuring levels of a plurality of biomarkers in said sample; (b) applying, by a processor, an algorithm to assess said absorbed dose in said patient based on said levels of said plurality of biomarkers in said sample; wherein said plurality of biomarkers comprises: (i) a DNA-damage biomarker; (ii) an inflammatory-response biomarker; (iii) a tissue-damage biomarker; (iv) a tissue-damage repair biomarker; (v) a hematology-surrogate marker; and (vi) combinations thereof.

In addition, the invention contemplates a method of assessing an absorbed dose of ionizing radiation in a patient sample, said method including (a) measuring levels of a plurality of biomarkers in said sample; (b) applying, by a processor, an algorithm to assess said absorbed dose in said patient based on said levels of said plurality of biomarkers in said sample; said plurality of biomarkers comprising (i) one or more biomarkers comprises Flt-3L, G-CSF, GM-CSF, EPO, CD27, CD45, SAA, CD26, IL-12, TPO, and combinations thereof; and (ii) an additional biomarker comprising: (a) a DNA-damage biomarker; (b) an inflammatory-response biomarker; (c) a tissue-damage biomarker; (d) a tissue-damage repair biomarker; (e) a hematology-surrogate marker; and (f) combinations thereof. In a preferred embodiment, the plurality of biomarkers comprises Flt-3L, GM-CSF, SAA, TPO, CD27, CD45, CD26, and IL-12.

The invention provides a number of multiplexed biodosimetry assay kit(s) used to assess an absorbed dose of ionizing radiation in a patient sample, said kit is configured to measure a level of a plurality of biomarkers in said sample, wherein the plurality of biomarkers comprises (a) Flt-3L, G-CSF, GM-CSF, EPO, CD27, CD45, SAA, CD26, IL-12, and/or TPO; and/or (b) Flt-3L, GM-CSF, SAA, TPO, CD27, CD45, CD26, and/or IL-12.

The invention also provides a variety of biodosimetry assay kits used to assess an absorbed dose of ionizing radiation in a patient sample, the kit(s) is (are) configured to measure a level of Flt-3L, G-CSF, GM-CSF, EPO, CD27, CD45, SAA, CD26, IL-12, TPO, and to compare said level(s) to a level of a normal control.

Another embodiment of the invention is a method of assessing an absorbed dose of ionizing radiation in a patient sample, said method comprising (a) measuring levels of a plurality of biomarkers in said sample;

(b) applying, by a processor, an algorithm to assess said absorbed dose in said patient based on said levels of said plurality of biomarkers in said sample; said plurality of biomarkers comprising (a) Flt-3L, G-CSF, GM-CSF, EPO, CD27, CD45, SAA, CD26, IL-12, TPO; or (b) Flt-3L, GM-CSF, SAA, TPO, CD27, CD45, CD26, IL-12.

Additionally, the invention includes a method of assessing an absorbed dose of ionizing radiation in a patient sample, said method comprising (a) measuring a level of Flt-3L, G-CSF, GM-CSF, EPO, CD27, CD45, SAA, CD26, IL-12, TPO in said sample; and (b) applying, by a processor, an algorithm to assess said absorbed dose in said patient based on said biomarker level in said sample.

Another embodiment of the invention is a method of determining an injury severity value comprising (a) measuring a level of a plurality of biomarkers in a patient sample, wherein one or more biomarkers of said plurality of biomarkers are altered relative to a normal control in the event of an injury in a patient;

(b) fitting, by a processor, said measured level to a response surface model as a function of an injury severity index and/or time;

(c) computing a cost function for combining said plurality of biomarkers; and (d) identifying an injury severity value that minimizes said cost function at a known time interval.

In addition, the invention includes a method of determining a radiation dose comprising (a) measuring a level of a plurality of biomarkers in a patient sample, wherein one or more biomarkers of said plurality of biomarkers are altered relative to a normal control in the event of radiation exposure;

(b) fitting, by a processor, said measured level to a response surface model as a function of radiation dose or time;

(c) computing a cost function for combining said plurality of biomarkers; and (d) selecting a radiation dose that minimizes said cost function at a known time interval.

In addition, the invention contemplates a computer readable medium having stored thereon a computer program which, when executed by a computer system operably connected to an assay system configured to measure a level of a plurality of biomarkers in a patient sample, causes the computer system to perform a method of calculating an injury severity value by a method comprising:

(a) fitting said measured level to a response surface model as a function of a injury severity index or time;

(b) computing a cost function for combining said plurality of biomarkers; and (c) identifying an injury severity value that minimizes said cost function at a known time interval.

In a further embodiment, the invention includes a computer readable medium having stored thereon a computer program which, when executed by a computer system operably connected to an assay system configured to measure a level of a plurality of biomarkers in a patient sample, causes the computer system to perform a method of calculating radiation dose by a method comprising:

(a) fitting said measured level to a response surface model as a function of radiation dose or time;

(b) computing a cost function for combining said plurality of biomarkers; and (c) selecting a radiation dose that minimizes said cost function at a known time interval.

An additional embodiment includes a multiplexed hematology surrogate biomarker assay kit configured to measure a level of a plurality of biomarkers in a sample, said plurality of biomarkers comprises a lymphocyte cell surface marker, a neutrophil cell surface marker, and combinations thereof.

And a final embodiment of the invention is a method of assaying peripheral blood leukocyte status in a sample comprising (a) measuring a level of a plurality of hematology surrogate biomarkers in a sample, said plurality of biomarkers comprises a lymphocyte cell surface marker, a neutrophil cell surface marker, and combinations thereof;

(b) comparing said level of said biomarkers in said sample to a level of said biomarkers in a normal control sample; and (c) determining said peripheral blood leukocyte status based on said comparison step (b).

BRIEF DESCRIPTION OF THE FIGURES

FIGS. 1(a)-(b) shows the effect of radiation on plasma Flt-3L levels in mice. Panel (a) shows the biomarker level as a function of time after radiation ($^{60}$Co γ-ray), with each line representing a different dose. Table 8 shows the significance (p values, unpaired t test, highlighting p values<0.01) for the change in the biomarker level for each irradiation condition, relative to the 0 Gy controls. Panel (b) shows the results of a Combined Injury Study comparing biomarker levels in mice receiving radiation alone (closed circles) vs. mice receiving radiation combined with a 15% surface area puncture wound (open circles). Each point on both plots represents the average level from 8 replicate animals.

FIGS. 2(a)-(b) shows the effect of radiation on plasma SAA levels in mice. Panel (a) shows the biomarker level as a function of time after radiation ($^{60}$Co γ-ray), with each line representing a different dose. Table 9 shows the significance (p values, unpaired t test, highlighting p values<0.01) for the change in the biomarker level for each irradiation condition, relative to the 0 Gy controls. Panel (b) shows the results of a Combined Injury Study comparing biomarker levels in mice receiving radiation alone (closed circles) vs. mice receiving radiation combined with a 15% surface area puncture wound (open circles). Each point on both plots represents the average level from 8 replicate animals.

FIGS. 3(a)-(b) shows the effect of radiation on plasma G-CSF levels in mice. Panel (a) shows the biomarker level as a function of time after radiation ($^{60}$Co γ-rays), with each line representing a different dose. Table 10 shows the significance (p values, unpaired t test, highlighting p values<0.01) for the change in the biomarker level for each irradiation condition, relative to the 0 Gy controls. Panel (b) shows the results of a Combined Injury Study comparing biomarker levels in mice receiving radiation alone (closed circles) vs. mice receiving radiation combined with a 15% surface area puncture wound (open circles). Each point on both plots represents the average level from 8 replicate animals.

FIGS. 4(a)-(b) shows the effect of radiation on plasma GM-CSF levels in mice. Panel (a) shows the biomarker level as a function of time after radiation ($^{60}$Co γ-rays), with each line representing a different dose. Table 11 shows the significance (p values, unpaired t test, highlighting p values<0.01) for the change in the biomarker level for each irradiation condition, relative to the 0 Gy controls. Panel (b) shows the results of a Combined Injury Study comparing biomarker levels in mice receiving radiation alone (closed circles) vs. mice receiving radiation combined with a 15% surface area puncture wound (open circles). Each point on both plots represents the average level from 8 replicate animals.

FIGS. 5(a)-(b) shows the results of a mouse radiation dose study, and in particular, the response of plasma IL-6 showing concentration vs time (panel (a)), concentration vs. dose (panel (b)) and the p values for irradiated vs. controls (unpaired t test, highlighting p values<0.01) for the response to each irradiation condition (Table 12).

FIGS. 6(a)-(b) shows the effect of radiation on plasma TPO levels in mice. Panel (a) shows the biomarker level as a function of time after radiation ($^{60}$Co γ-rays), with each line representing a different dose. Table 13 shows the significance (p values, unpaired t test, highlighting p values<0.01) for the change in the biomarker level for each irradiation condition, relative to the 0 Gy controls. Panel (b) shows the results of a Combined Injury Study comparing biomarker levels in mice receiving radiation alone (closed circles) vs. mice receiving radiation combined with a 15% surface area puncture wound (open circles). Each point on both plots represents the average level from 8 replicate animals.

FIGS. 7(a)-(b) shows the effect of radiation on plasma EPO levels in mice. Panel (a) shows the biomarker level as a function of time after radiation ($^{60}$Co γ-rays), with each line representing a different dose. Table 14 shows the significance (p values, unpaired t test, highlighting p values<0.01) for the change in the biomarker level for each irradiation condition, relative to the 0 Gy controls. Panel (b) shows the results of a Combined Injury Study comparing biomarker levels in mice receiving radiation alone (closed circles) vs. mice receiving radiation combined with a 15% surface area puncture wound (open circles). Each point on both plots represents the average level from 8 replicate animals.

FIGS. 8(a)-(b) shows the effect of radiation on plasma IL-5 levels in mice. Panel (a) shows the biomarker level as a function of time after radiation ($^{60}$Co γ-ray), with each line representing a different dose. Table 15 shows the significance (p values, unpaired t test, highlighting p values<0.01) for the change in the biomarker level for each irradiation condition, relative to the 0 Gy controls. Panel (b) shows the results of a Combined Injury Study comparing biomarker levels in mice receiving radiation alone (closed circles) vs. mice receiving radiation combined with a 15% surface area puncture wound (open circles). Each point on both plots represents the average level from 8 replicate animals.

FIGS. 9(a)-(b) shows the results of a mouse radiation dose study, and in particular, the response of plasma IL-10 showing concentration vs time (panel (a)), concentration vs. dose (panel (b)) and the p values for irradiated vs. controls (unpaired t test, highlighting p values<0.01) for the response to each irradiation condition (Table 16).

FIGS. 10(a)-(b) shows the results of a mouse radiation dose study, and in particular, the response of plasma KC/GRO showing concentration vs time (panel (a)), concentration vs. dose (panel (b)) and the p values for irradiated vs. controls (unpaired t test, highlighting p values<0.01) for the response to each irradiation condition.

FIGS. 1 (a)-(b) shows the results of a mouse radiation dose study, and in particular, the response of plasma TNF-α showing concentration vs time (panel (a)), concentration vs. dose (panel (b)) and the p values for irradiated vs. controls (unpaired t test, highlighting p values<0.01) for the response to each irradiation condition (Table 17).

FIGS. 12(a)-(b) shows the results of a mouse radiation dose study, and in particular, the response of γ-H2AX in blood cell pellets showing concentration vs time (panel (a)), concentration vs. dose (panel (b)) and the p values for irradiated vs. controls (unpaired t test, highlighting p values<0.01) for the response to each irradiation condition (Table 19).

FIGS. 13(a)-(b) shows the results of a mouse radiation dose study, and in particular, the response of p53 in blood cell pellets showing concentration vs time (panel (a)), concentration vs. dose (panel (b)) and the p values for irradiated vs. controls (unpaired t test, highlighting p values<0.01) for the response to each irradiation condition (Table 20).

FIGS. 14(a)-(b) shows the effect of radiation on plasma CD-27 levels in mice. Panel (a) shows the biomarker level as a function of time after radiation ($^{60}$Co γ-rays), with each line representing a different dose. Table 21 shows the significance (p values, unpaired t test, highlighting p values<0.01) for the change in the biomarker level for each irradiation condition, relative to the 0 Gy controls. Panel (b) shows the results of a Combined Injury Study comparing biomarker levels in mice receiving radiation alone (closed circles) vs. mice receiving radiation combined with a 15% surface area puncture wound (open circles). Each point on both plots represents the average level from 8 replicate animals.

FIGS. 15(a)-(b) shows the effect of radiation on plasma IL-12 levels in mice. Panel (a) shows the biomarker level as a function of time after radiation ($^{60}$Co γ-rays), with each line representing a different dose. Table 22 shows the significance (p values, unpaired t test, highlighting p values<0.01) for the change in the biomarker level for each irradiation condition, relative to the 0 Gy controls. Panel (b) shows the results of a Combined Injury Study comparing biomarker levels in mice receiving radiation alone (closed circles) vs. mice receiving radiation combined with a 15% surface area puncture wound (open circles). Each point on both plots represents the average level from 8 replicate animals.

FIGS. 16(a)-(b) shows the effect of radiation on plasma CD45 levels in mice. Panel (a) shows the biomarker level as a function of time after radiation ($^{60}$Co γ-rays), with each line representing a different dose. Table 23 shows the significance (p values, unpaired t test, highlighting p values<0.01) for the change in the biomarker level for each irradiation condition, relative to the 0 Gy controls. Panel (b) shows the results of a Combined Injury Study comparing biomarker levels in mice receiving radiation alone (closed circles) vs. mice receiving radiation combined with a 15% surface area puncture wound (open circles). Each point on both plots represents the average level from 8 replicate animals.

FIGS. 17(a)-(b) shows the effect of radiation on plasma CD26 levels in mice. Panel (a) shows the biomarker level as a function of time after radiation ($^{60}$Co γ-rays), with each line representing a different dose. Table 24 shows the significance (p values, unpaired t test, highlighting p values<0.01) for the change in the biomarker level for each irradiation condition, relative to the 0 Gy controls. Panel (b) shows the results of a Combined Injury Study comparing biomarker levels in mice receiving radiation alone (closed circles) vs. mice receiving radiation combined with a 15% surface area puncture wound (open circles). Each point on both plots represents the average level from 8 replicate animals.

FIGS. 20(a)-(b) show the dose classification accuracy for the mouse Biomarker Discovery data set using a multi-parameter algorithm. Two performance metrics are plotted as a function of the number of biomarkers used. Each point represents the performance of a different combination of biomarkers; all possible combinations of the 12 most radiation sensitive biomarkers are shown. In Panel (a), accuracy is displayed as the percent of samples correctly classified by dose (within 1.5 Gy for doses≤6 Gy and within 25% for doses>6 Gy). In Panel (b), prediction error is displayed as the RMS error in the dose prediction across all samples. Two high-performing biomarker combinations were selected for each panel size: a panel that did not include injury sensitive markers (yellow data points) and a panel that did include injury-sensitive markers (red data points). The performance metrics for these selected panels are tabulated in Table 8.

FIGS. 24(a)-(z) show the effect of radiation on plasma biomarkers (Flt-3L, CD20, CD27, TPO, CD177, IL-12, SAA, EPO, G-CSF, salivary amylase (AMY), CRP, TIMP-1 and TNF-RII, respectively) in Rhesus macaque. Plots show levels as a function of the time after radiation. Panels shown on the left reflect the results using samples exposed to $^{60}$Co γ-rays and panels shown on the right reflect the results using samples exposed to 3 MV LINAC photons. Each point in the plots represents 5 to 6 animals for the $^{60}$Co γ-rays samples, 3 to 4 animals for the 3 MV LINAC samples up to the 9 day time point and 2 animals for the time points>9 days. Graphs are linear, with the exception of FIGS. 25(b) and (d) which is logarithmic.

FIGS. 24(aa)-(dd) show the analysis of CD20, CD177, neutrophils, and lymphocytes in irradiated NHP samples, demonstrating the potential of the biomarkers as surrogates radiation-responsive biomarkers in lieu of blood cell counting. Each graph shows the time course effects of radiation on the biomarker or biomarker ratio in NHPs (n=6 for each dose and time cohort).

FIGS. 25(a)-(b) show the performance of the multi-parameter algorithm for classifying NHP samples from sample set (A) by radiation dose. The data set was used to train and test the algorithm using a random sub-sampling approach to avoid training bias. The focus of the analysis shown in this plot is the ability of the algorithm to correctly classify samples above or below the critical 2 Gy dose threshold in humans, which is roughly equivalent to 3 Gy in the NHP model. Panel A shows ROC curves for distinguishing doses≥3.5 Gy from non-irradiated controls (blue) and for distinguishing doses≥3.5 Gy from doses≤1 Gy. The ROC curves were generated by varying the value of the predicted dose used to classify the samples. The histogram inset shows the distribution of the predicted doses for samples receiving 0 Gy, 1 Gy or 3.5 Gy doses and demonstrates the separation of these distributions. Classification performance at the optimal predicted dose thresholds is provided in the table below the plot. Panel B shows predicted doses for the NHP samples plotted as a function of actual dose.

DETAILED DESCRIPTION OF THE INVENTION

Figure 18A:
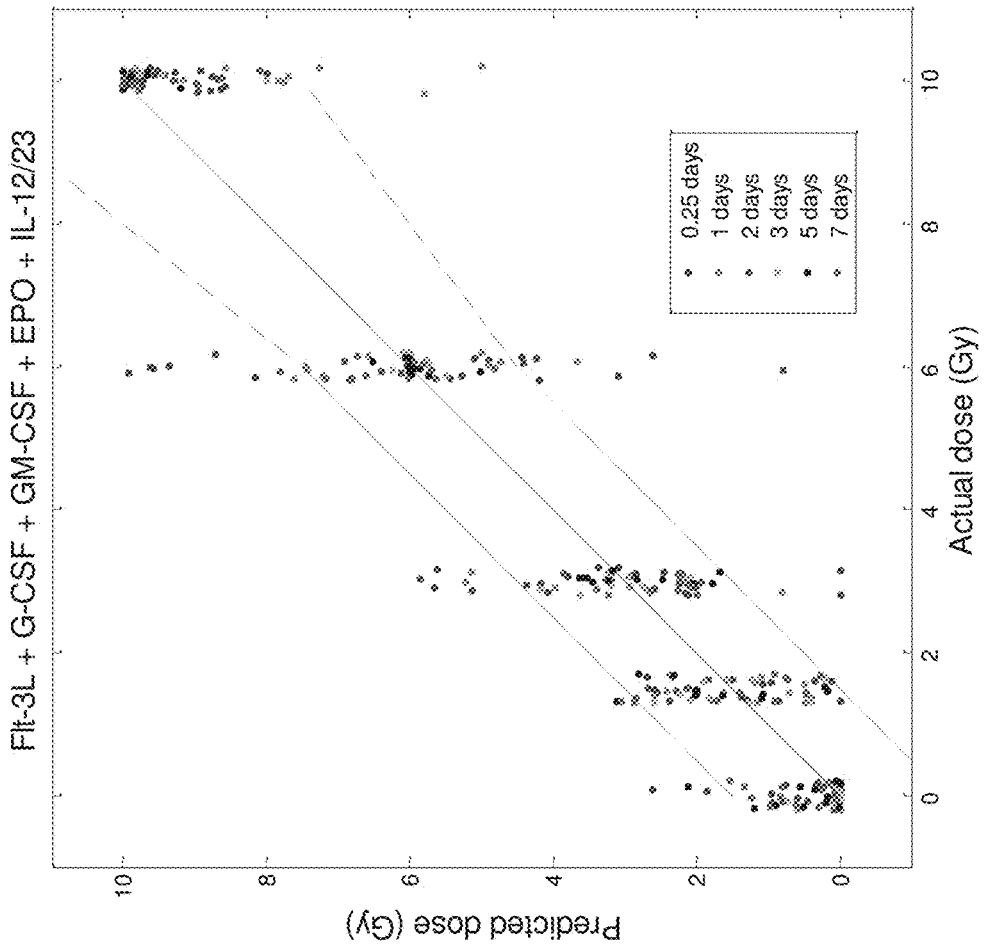
FIGS. 18(a)-(b) are scatter plots showing the predicted dose as a function of actual dose for the full mouse radiation dose study sample set using a multi-parameter dose assessment algorithm. The different colors correspond to different sampling times. The data are slightly dithered along the X-axis to make the points clearly visible. Points on the solid lines exactly match the actual dose. Points within the dashed lines are within 1.5 Gy of the actual dose (below 6 Gy) or within 25% of the actual dose (above 6 Gy). Panel (a) includes results using the optimal 5 biomarker panel (Flt-3L, G-CSF, GM-CSF, EPO, IL12/23). Panel (b) includes results using a smaller LPS-insensitive panel (Flt-3L, EPO).

Unless otherwise defined herein, scientific and technical terms used herein shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

One embodiment of the invention is a multiplexed biodosimetry assay kit and methods that can be used to assess an absorbed dose of ionizing radiation in a patient sample. The methods and kits of the invention can be used to assess the likelihood or risk of developing acute radiation syndrome (ARS) and/or to assess the clinical severity of ARS in a patient. Depending on the type of radiation exposure, the methods and kits of the present invention may be used to assess radiation dose in any suitable unit of measurement. For example, an absorbed dose of ionizing radiation following external exposure can be measured in a variety of suitable units of measurement, including but not limited to Gray (or rad), and sievert (or rem); a dose of radiation after internal contamination is measured as Committed Effective Dose Equivalent (CEDE); and a dose associated with external and internal exposure is measured as Total Effective Dose Equivalent (TEDE).

Assay panel(s) employed in certain embodiments of the instant invention include a plurality of radiation biomarkers used to assess radiation exposure. A radiation biomarker can be any substance that acts as an indicator of the exposure of an organism to radiation, including but not limited to, proteins, nucleic acids, carbohydrates and metabolites. In one embodiment, the biomarkers included in the panel are all proteins.

Suitable assay panels comprise at least one radiation biomarker from at least 1, 2, 3, 4 or 5 of the following biomarker classes: DNA-damage biomarkers, inflammatory-response biomarkers, tissue-damage biomarkers, tissue-damage repair biomarkers, and hematology-surrogate biomarkers. As used herein, a DNA-damage biomarker is a radiation biomarker associated with the host response to radiation induced DNA damage. An inflammatory-response biomarker is a radiation biomarker that is up- or down-regulated during a systemic or localized inflammatory response caused by radiation exposure. A tissue-damage biomarker is a radiation biomarker that is released from a tissue as a result of local tissue damage caused by radiation, whereas a tissue-damage repair biomarker is a protein that is up- or down-regulated during a repair, regeneration, or fibroblastic phase following tissue damage. Tissue-damage repair biomarkers may also include proteins associated with soft-tissue repair processes, including but not limited to fibroblast formation, collagen synthesis, tissue remodeling, and realignment. Finally, hematology-surrogate biomarkers are cell-surface markers for blood cells, which may be used as surrogates to traditional blood cell counts, for assessing the effect of radiation on specific blood-cell populations. Useful hematology surrogate markers include markers found on general classes of cells (e.g., leukocytes) or more specific cell types within those classes such as lymphocytes, neutrophils and platelets or, even more specifically, T-cells or B-cells.

There may be some overlap between the biomarker categories described above. For example, some inflammatory response biomarkers may also be associated with tissue-damage repair. In one embodiment, the radiation biomarker panel includes at least one inflammatory-response biomarker and at least one tissue-damage repair biomarker. In an alternate embodiment, the panel includes a biomarker that is both an inflammatory response biomarker and a tissue-damage repair biomarker.

A non-limiting list of biomarkers that can be used in the instant invention is provided in Table 1 below.

TABLE 1

| Biomarker Class | Exemplary Biomarkers | |
| --- | --- | --- |
| DNA-damage biomarker | p53 | ATM |
| | p21 | phosphorylated H2AX histone |
| | GADD45a | (γ-H2AX) |
| Inflammatory-response biomarker | IL-6 | IFN |
| | CRP | IL-2 |
| | SAA | IL-4 |
| | IL-1 | TNF-alpha |
| | IL-5 | IL-12 |
| | IL-10 | IL-3 |
| | IL12/23 | IL-7 |
| | KC/GRO | |

TABLE 1-continued

| Biomarker Class | Exemplary Biomarkers | |
| --- | --- | --- |
| Tissue-damage biomarker | salivary alpha-amylase citrullinated proteins S100B SP-D BPI TSP CA15-3 | CKBB CKMB CKMM FABP2 GFAP NSE |
| Tissue-damage repair biomarker | Flt-3L G-CSF KFG EPO | TPO GM-CSF SDF-1a |
| Hematology-surrogate biomarker | CD5 CD-16b CD20 CD177 | CD26 CD27 CD40 CD45 |

In a preferred embodiment, the assay panel used in the present invention is configured to measure a level of a plurality of biomarkers in a sample, wherein the plurality of biomarkers includes one or more of Flt-3L, G-CSF, GM-CSF, EPO, CD27, CD45, SAA, CD26, IL-12, TPO, and combinations thereof, and/or an additional biomarker comprising a DNA-damage biomarker, an inflammatory-response biomarker, a tissue-damage biomarker, a tissue-damage repair biomarker, a hematology-surrogate biomarker, and combinations thereof. In a specific embodiment, the panel includes Flt-3L, GM-CSF, SAA, TPO, CD27, CD45, CD26, IL-12, and combinations thereof. In one embodiment, the IL-12 assay is specific for the IL-12 p40 subunit in the IL-12 p70 heterodimer and may also cross-react with IL-23 (which also comprises the p40 subunit). In another embodiment, the IL-12 assay is specific for the full IL-12 p70 heterodimer.

The selected biomarkers for assessing exposure to radiation are, preferably, not significantly affected by chronic diseases with high prevalence in the human population, such as diabetes, asthma, high blood pressure, heart disease, arthritis and/or other chronic inflammatory or autoimmune diseases. The selected biomarkers for assessing exposure to radiation are, preferably, also not affected by other types of trauma (e.g., wounding, burns and/or mental stress) that may also be experienced by individuals in a radiation event. In one embodiment, the biomarker response associated with total body radiation exposure (for example, at 2, 6, 10 or 12 Gy) is less than the biomarker response associated with the biomarker response associated with wound, burn and/or mental trauma. Such comparison, may be determined through the use of a combined injury animal model. We note that biomarkers that have a significant confounding effect from confounding diseases or trauma may still be selected and have value in a dose assessment algorithm. In one embodiment, biomarkers that may be affected by such confounding effects are included, and information about the presence or absence of such confounding conditions is included in the algorithm for dose assessment. For example, if a potentially confounding condition is identified in a patient (such as a confounding disease or trauma) approaches that may be taken to minimize the effect of the confounding condition on the accuracy of a dose assessment algorithm include: i) excluding the patient from analysis using the algorithm; ii) applying the algorithm, but using a redacted biomarker panel that excludes or applies less weight to biomarkers that are likely to be affected by the confounding condition or iii) applying a different algorithm employing a biomarker panel that has been selected to be robust to the confounding condition.

The kits of the present invention can further include devices, reagents, and/or consumables for measuring hematological parameters, such as peripheral blood cell counts, or for measuring "Acute Phase Reaction" (APR) biomarkers. Such assay components can be modifications of commercially available products for assessing blood cell counts and APR biomarkers, such as the Quikread CRP finger-prick device (Orion Diagnostica, Finland) which measures the level of C-reactive protein.

In a preferred embodiment, the invention includes assays for cell-surface markers for lymphocytes and neutrophils which are useful as surrogates for lymphocyte and neutrophil counts. The invention provides a method of conducting a multiplexed hematology-surrogate biomarker assay and kits therefor, including a kit configured to measure a level of a plurality of biomarkers in a sample, including lymphocyte cell-surface markers and/or neutrophil cell-surface markers. In one embodiment, the lymphocyte-surface marker comprises CD5, CD20, CD26, CD27, CD40, or combinations thereof. Additionally, the neutrophil cell-surface marker includes CD16b, CD177, or combinations thereof. The hematology-surrogate biomarker assay methods of the present invention can be conducted on a sample comprising whole blood, blood cell pellets, serum, and/or plasma. In one embodiment, the measurements are carried out in samples prepared by reconstituting dried blood spots. In another embodiment, such measurements are carried out using serum and/or plasma samples. In a preferred embodiment, measurements are carried out using plasma samples. Surprisingly, we have discovered that the free (i.e., non-cell bound) forms of neutrophil and lymphocyte surface markers can be measured in plasma and the levels of these markers in plasma after radiation exposure provide useful diagnostic information for assessment of the effects of radiation on neutrophils and lymphocytes.

One of average skill in the art of biological assays will be aware of numerous suitable approaches and instrumentation for measuring the biomarkers and biomarker panels of the invention. In one embodiment, the kit is configured to measure biomarker levels using an immunoassay. In a preferred embodiment, the kit includes a multi-well assay plate comprising a plurality of assay wells configured to measure the level of said plurality of biomarkers in one or more samples. Preferably, the wells are configured to enable the use of individual wells to conduct multiplexed measurements of a plurality of different biomarkers. In one such assay plate, a well of the assay plate includes a plurality of assay domains, at least two of the assay domains comprising reagents for measuring different biomarkers. In an alternative preferred embodiment, the kit includes an assay cartridge to measure biomarkers in a sample. Preferably, the cartridge comprises a flow cell having an inlet, an outlet and a detection chamber, said inlet, detecting chamber, and outlet defining a flow path through said flow cell, said detection chamber configured to measure said level of said plurality of biomarkers in said sample. Kits used in the present method can further include one or more additional assay reagents used in an assay and those additional reagents can be provided in one or more vials, containers, or compartments of a kit. Moreover, a kit for assessing exposure to radiation can also include (a) a bar-coded patient identification tag; (b) a dried blood spot collection card comprising a bar code that for example, can be used to facilitate sample identification; (c) a sample transport bag comprising desiccant; (d) a capillary with a plunger; and/or (e) a lancet.

The samples that can be analyzed in the kits and methods of the invention include but are not limited to, any biological fluid, cell, tissue, organ and combinations or portions thereof, which includes or potentially includes a biomarker of a disease, disorder, or abnormality of interest. For example, a sample can be a histologic section of a specimen obtained by biopsy, or cells that are placed in or adapted to tissue culture. A sample further can be a subcellular fraction or extract, or a crude or substantially pure nucleic acid molecule or protein preparation. In one embodiment, the samples that are analyzed in the assays of the present invention are blood or blood fractions such as, blood pellet, serum, or plasma. Other suitable samples include biopsy tissue, intestinal mucosa, urine, parotid gland, hematological tissues, intestine, liver, pancreas, or nervous system. The sample can be taken from any patient, including but not limited to animals, mammals, primates, non-human primates, humans, and the like. In one embodiment, the level is measured using an immunoassay. The radiation biomarker panels disclosed herein may be used at the onset and throughout the course of the acute radiation syndrome to assess and monitor patient health. In a preferred embodiment, a sample is collected from a patient within about 1 to 7 days of radiation exposure.

As used herein, a "biomarker" is a substance that is associated with a particular biological state, which can be a disease or abnormal condition. A change in the levels of a biomarker can correlate with the risk or progression of a disease or abnormality or with the susceptibility of the disease or abnormality to a given treatment. A biomarker can be useful in the diagnosis of disease risk or the presence of disease in an individual, or to tailor treatments for the disease in an individual (choices of drug treatment or administration regimes). In evaluating potential drug therapies, a biomarker can be used as a surrogate for a natural endpoint such as survival or irreversible morbidity. If a treatment alters a biomarker that has a direct connection to improved health, the biomarker serves as a "surrogate endpoint" for evaluating clinical benefit.

As used herein, the term "level" refers to the amount, concentration, or activity of a biomarker. The term "level" can also refer to the rate of change of the amount, concentration or activity of a biomarker. A level can be represented, for example, by the amount or synthesis rate of messenger RNA (mRNA) encoded by a gene, the amount or synthesis rate of polypeptide corresponding to a given amino acid sequence encoded by a gene, or the amount or synthesis rate of a biochemical form of a biomarker accumulated in a cell, including, for example, the amount of particular post-synthetic modifications of a biomarker such as a polypeptide, nucleic acid or small molecule. The term can be used to refer to an absolute amount of a biomarker in a sample or to a relative amount of the biomarker, including amount or concentration determined under steady-state or non-steady-state conditions. Level can also refer to an assay signal that correlates with the amount, concentration, activity or rate of change of a biomarker. The level of a biomarker can be determined relative to a control marker in a sample.

Specific biomarkers valuable in distinguishing between normal and diseased/exposed patients can be identified by visual inspection of the data, for example, by visual classification of data plotted on a one-dimensional or multidimensional graph, or by using statistical methods such as characterizing the statistically weighted difference between control individuals and diseased patients and/or by using Receiver Operating Characteristic (ROC) curve analysis. A variety of suitable methods for identifying useful biomarkers and setting detection thresholds/algorithms are known in the art and will be apparent to the skilled artisan.

For example and without limitation, diagnostically valuable biomarkers can be first identified using a statistically weighted difference between control individuals and exposed or abnormal patients, calculated as $$\frac{D-N}{\sqrt{\sigma_D * \sigma_N}}$$

wherein D is the median level of a biomarker in patients diagnosed as having been exposed to radiation, N is the median (or average) of the control individuals, $\delta_D$ is the standard deviation of D and $\sigma_N$ is the standard deviation of N. The larger the magnitude, the greater the statistical difference between the diseased and normal populations.

According to one embodiment of the invention, biomarkers resulting in a statistically weighted difference between control individuals and diseased/exposed patients of greater than, e.g., 1, 1.5, 2, 2.5 or 3 could be identified as diagnostically valuable markers.

Another method of statistical analysis for identifying biomarkers is the use of z-scores, e.g., as described in Skates et al. (2007) Cancer Epidemiol. Biomarkers Prev. 16(2):334-341.

Another method of statistical analysis that can be useful in the inventive methods of the invention for determining the efficacy of particular candidate analytes, such as particular biomarkers, for acting as diagnostic marker(s) is ROC curve analysis. An ROC curve is a graphical approach to looking at the effect of a cut-off criterion, e.g., a cut-off value for a diagnostic indicator such as an assay signal or the level of an analyte in a sample, on the ability of a diagnostic to correctly identify positive or negative samples or subjects. One axis of the ROC curve is the true positive rate (TPR, i.e., the probability that a true positive sample/subject will be correctly identified as positive, or alternatively, the false negative rate (FNR=1−TPR, the probability that a true positive sample/subject will be incorrectly identified as a negative). The other axis is the true negative rate, i.e., TNR, the probability that a true negative sample will be correctly identified as a negative, or alternatively, the false positive rate (FPR=1−TNR, the probability that a true negative sample will be incorrectly identified as positive). The ROC curve is generated using assay results for a population of samples/subjects by varying the diagnostic cut-off value used to identify samples/subjects as positive or negative and plotting calculated values of TPR or FNR and TNR or FPR for each cut-off value. The area under the ROC curve (referred to herein as the AUC) is one indication of the ability of the diagnostic to separate positive and negative samples/subjects. In one embodiment, a biomarker provides an AUC≥0.7. In another embodiment, a biomarker provides an AUC≥0.8. In another embodiment, a biomarker provides an AUC≥0.9.

Diagnostic indicators analyzed by ROC curve analysis can be a level of an analyte, e.g., a biomarker, or an assay signal. Alternatively, the diagnostic indicator can be a function of multiple measured values, for example, a function of the level/assay signal of a plurality of analytes, e.g., a plurality of biomarkers, or a function that combines the level or assay signal of one or more analytes with a patient's scoring value that is determined based on visual, radiological and/or histological evaluation of a patient. The multi-parameter analysis can provide more accurate diagnosis relative to analysis of a single marker.

Candidates for a multi-analyte panel could be selected by using criteria such as individual analyte ROC areas, median difference between groups normalized by geometric interquartile range (IQR) etc. The objective is to partition the analyte space to improve separation between groups (for example, normal and disease populations) or to minimize the misclassification rate.

One approach is to define a panel response as a weighted combination of the response for the individual analytes and then compute an objective function like ROC area, product of sensitivity and specificity, etc. See e.g., WO 2004/058055, as well as US2006/0205012, the disclosures of which are incorporated herein by reference in their entireties. The weighting coefficients define the partitioning object; for linear combinations the object is a line in 2 dimensions, a plane in 3 dimensions and a hyperplane in higher dimensions. The optimal coefficients maximize the objective function and can be determined using algorithms for finding function extrema in multiple dimensions, e.g., gradient descent methods, downhill simplex methods, simulated annealing and the like; more details can be found in "Numerical Recipes in C, The Art of Scientific Computing", W. Press et al., Cambridge University Press, 1992.

Another approach is to use discriminant analysis, where a multivariate probability distribution (normal, multinomial etc.) is used to describe each group. Several distributions result in partitioning hyperplanes in analyte space. One advantage of this approach is the ability to classify measurements into multiple groups (e.g. normal, disease 1, disease 2) simultaneously, rather than two at a time. For further details, see "Principles of Multivariate Analysis, A User's Perspective", W. J. Krzanowski, Oxford University Press, 2000 and "Multivariate Observations", G. A. F. Seber, John Wiley, 2004.

Once the partitioning hyperplanes have been determined, the robustness of different assay panels can be compared by evaluating a distance metric to the separating hyperplanes for each group. It is noteworthy that the algorithms described above are designed to find the best classification between groups; therefore these algorithms can also be used to distinguish between different diseases or populations or subgroups of the same disease or population. Finally, categorical data (age, gender, race, ethnicity, etc.) can also be coded into different levels and used as an optimizing variable in this process.

In one embodiment, the invention provides a radiation dose-calculation algorithm that includes (a) measuring the levels of a plurality of radiation biomarkers in a patient sample; (b) fitting said measured levels to response surface models for the response of said biomarkers as a function of radiation dose and sample time; (c) computing a cost function for combining the plurality of biomarkers; (d) selecting a calculated radiation dose and calculated sample time that minimizes the cost function; and optionally, (e) comparing said calculated radiation dose to a threshold value to classify individuals according to dose received (for example, to distinguish exposed from non-exposed individuals or to identify patients who would benefit from a treatment option.

Sample time, as used herein, refers to the time between the radiation exposure event and the time at which the sample was collected. In applications where the sample time is known or is expected to be known, for example when the exposure occurred in a defined time frame, the actual sample time can be provided to the algorithm. In these cases, only the calculated radiation dose needs to be selected in step (d) above.

In a preferred embodiment, 2-parameter response functions are determined, i.e., $M_i$ (dose, time), where $M_i$ is the expected level of marker i as a function of dose and sample time. Alternatively, $M_i$ may also represent the expected level of a derived value i derived from the level of one or more biomarkers, such as the reciprocal of a marker level, the log of a marker level, the ratio or product of the levels of two markers, etc. Preferably, the response functions are established based on pre-existing data from human, animal or in vitro studies.

Based on these established response functions, one can determine the radiation exposure dose (and, optionally the sample time, if the dose is known but the sample time is not known) that provides the best overall fit of the different markers (or derived values) to their respective response functions. One general form of a cost function (F) that can be minimized to find the best fit is provided by the equation below. $E_i$ is a function that provides a value associated with the discrepancy between the measured level of a biomarker (or derived value) i ($m_i$) and the expected level of the biomarker (or derived value) predicted by the response surface for a given dose-time condition ($M_i$(dose,time)). $W_i$ is a weighting function that may be dose-dependent and/or time-dependent for each marker i. The weighting function may be used to vary the importance given to certain markers in certain dose and time ranges. In one embodiment, the weighting is determined based on the statistical significance of the measurement at that dose and time point. A number of different weighting functions can be used, e.g., the inverse of the coefficient of variation (CV) of the biomarker level at that dose and time. Optionally, the weighting function may be omitted.

$$F(\text{dose, time}) = \sum_{i=1}^{n} W_i(\text{dose, time}) E_i(m_i, M_i(\text{dose, time}))$$

Examples of possible methods for calculating $E_i$ include calculating the difference, the absolute value of the difference or the square of the difference of $m_i$ and $M_i$. In one embodiment, the values of $m_i$ and $M_i$ are normalized to avoid over-emphasizing the more abundant biomarkers by, for example, dividing them by the minimum, maximum, median or average value for normal samples or for all expected samples. One specific example of a preferred cost function with a normalization factor is provided below, which corresponds to a "least squares fit" with each term normalized to the product of the measured value and fit value, and scaled by a weighting function.

$$F(\text{dose, time}) = \sum_{i=1}^{n} W_i(\text{dose, time}) \frac{(m_i - M_i(\text{dose, time}))^2}{m_i \times M_i(\text{dose, time})}$$

The cost function may also transform the values of $M_i$ and $m_i$. In the preferred cost function described below, log values are used to minimize an over-emphasis on biomarkers with the largest fold-changes and also to minimize bias for biomarkers with higher abundances.

$$F(\text{dose}) = \sum_{i=1}^{n} \left| \text{Log}\left(\frac{m_i}{M_i(\text{dose})}\right) \right|$$

The measured and fit values for the biomarker levels may also be added linearly or in quadrature to the limit of detection (LOD) or lower limit of quantitation to minimize the effect on the cost function of changes in levels near to the detection limit as in the function below.

$$F(\text{dose}) = \sum_{i=1}^{n} \left| \text{Log}\left( \frac{m_i + LOD_i}{M_i(\text{dose}) + LOD_i} \right) \right|,$$

wherein $m_i$ is the measured value for biomarker i, $M_i$ is the predicted biomarker value as a function of dose at a known time post-exposure, $LOD_i$ is the assay Limit of Detection for biomarker i, and n is the total number of biomarkers being used.

The algorithm described above for assessing radiation dose can also be applied more generally to disease conditions that can be assessed in the clinical setting using a severity index, i.e., a classification scale used by clinicians to characterize the stage of a disease or disorder. A variety of conditions are assessed using severity indices, e.g., comprising traumatic brain injury, stroke, embolism, liver disease, kidney disease, heart disease, inflammatory bowel disease, Alzheimer's disease, dementia, thyroid disease, rheumatoid arthritis, multiple sclerosis, psoriasis, systemic lupus erythematosus, Hashimoto's thyroiditis, Pernicious anemia, Addison's disease, Type I diabetes, dermatomyositis, Sjogren syndrome, myasthenia gravis, reactive arthritis, Grave's disease, Celiac disease, or cancer.

Figure 38A:
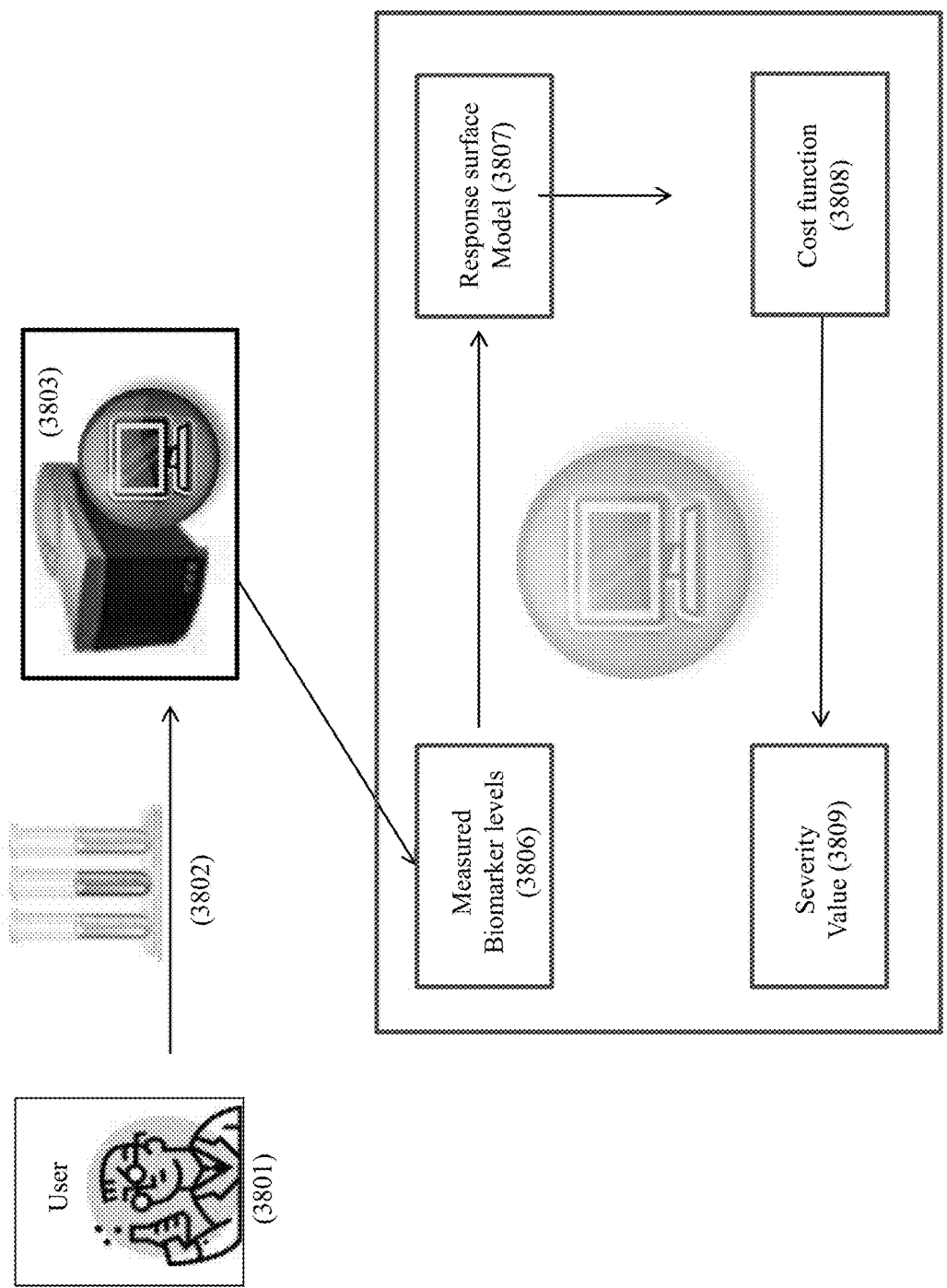
FIGS. 38(a)-(b) show the use of the statistical methods described herein to generate a severity value or a radiation dose, respectively, from a patient sample by analyzing one or more biomarkers in the same and correlating the level(s) of those biomarkers with an injury severity value or a radiation dose, respectively.
Figure 38B:
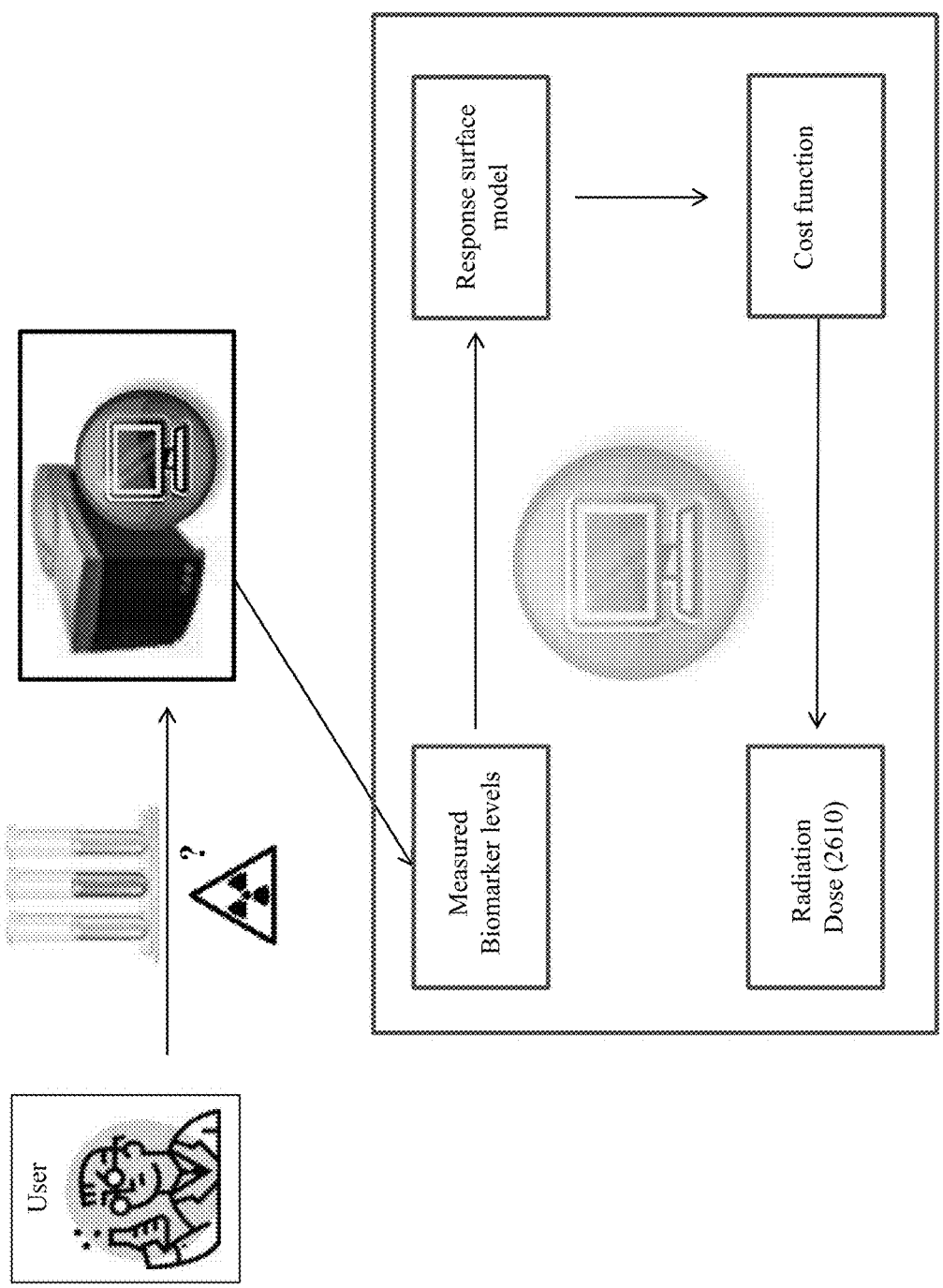
Figure 38C:
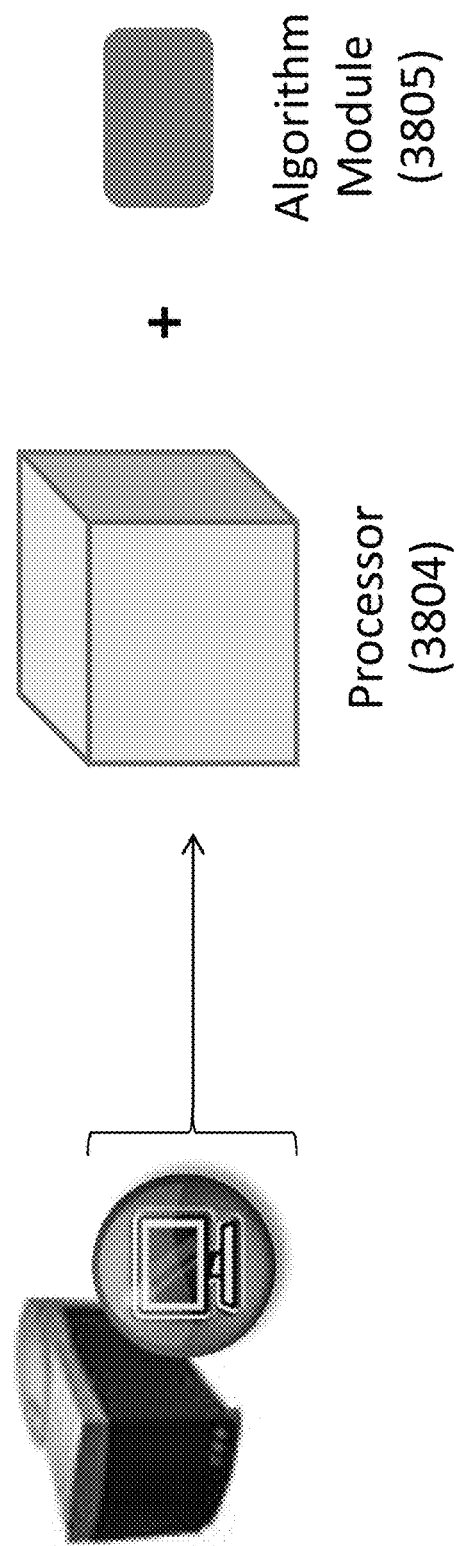
FIG. 38(c) illustrates one non-limiting example of a system used to analyze a sample using the statistical methods described herein, wherein the system includes a processor and an algorithm module.

In this regard, the algorithm described above can be used as an injury severity value calculation algorithm that includes (a) measuring a level of a plurality of biomarkers in a patient sample, wherein one or more biomarkers of the plurality of biomarkers are altered relative to a normal control in the event of to injury in a patient; (b) fitting the measured level to a response surface model as a function of an injury severity index or time; (c) computing a cost function for combining the plurality of biomarkers; (d) identifying an injury severity value that minimizes the cost function at a known time interval; and optionally, (e) comparing the injury severity value to a threshold value, wherein an injury severity value above the threshold value indicates the relative severity of the injury. This is illustrated in FIG. 38(a), in which a user (3801) measures a plurality of biomarkers in a patient sample (3802) using an assay system (3803) (including a processor (3804) and an algorithm module (3805), as illustrated in FIG. 38(c)). The processor and algorithm module of the assay system fits the measured biomarker levels (3806) to a response surface model (3807), computes a cost function (3808), and identifies a severity index (3809). Likewise, the use of the statistical methods to analyze a radiation dose in a sample is illustrated in FIG. 38(b) in which a radiation dose (3810) is generated using the statistical method.

In this embodiment, the cost function is $$F(SI) = \sum_{i=1}^{n} \left| \text{Log}\left( \frac{m_i + LOD_i}{M_i(SI) + LOD_i} \right) \right|,$$

wherein $m_i$ is the measured value for biomarker i, $M_i$ is the predicted biomarker value as a function of a severity index (SI) at a known time post-injury, $LOD_i$ is the assay limit of detection for biomarker i, or n is the total number of biomarkers being used. Preferably, the cost function is:

$$F(SI) = \sum_{i=1}^{n} \left| \text{Log}\left( \frac{m_i}{M_i(SI)} \right) \right|.$$

wherein $m_i$ is the measured value for biomarker i, $M_i$ is the predicted biomarker value as a function of a severity index (SI) at a known time post-injury, or n is the total number of biomarkers being used.

Other statistical methods can be used to conduct multivariate analyses of biomarker levels. For example, a neural net approach can be used (see e.g., Musavi, et al., Neural Networks (1992) (5): 595-603; Wang, et al., Artif. Intell. Med. (2010) 48 (2-3): 119-127; Lancashire, L. et al., Computational Intelligence in Bioinformatics and Computational Biology (2005): pp. 1-6, 14-15). Neural networks are a wide class of flexible models used for simulating nonlinear systems. They consist of an often large number of "neurons," i.e. simple linear or nonlinear computing elements, interconnected in often complex ways and often organized into layers. Other modeling approaches include but are not limited to linear models, support vector machines and discriminant analysis (Lancashire et al., "Utilizing Artificial Neural Networks to Elucidate Serum Biomarker Patterns Which Discriminate Between Clinical Stages in Melanoma," Proceedings of the 2005 IEEE Symposium on Computational Intelligence in Bioinformatics and Computational Biology, Nov. 14-15, 2005, pp. 1-6; Wang et al., "Method of regulatory network that can explore protein regulations for disease classification," Artif Intell Med., 48 (2-3) (2010), pp. 119-127).

Therefore, the methods of the present invention can be used to assess an absorbed dose of ionizing radiation in a patient sample by measuring levels of a plurality of biomarkers in a sample and applying an algorithm to assess the absorbed dose in the sample based on the levels of the plurality of biomarker in the samples, wherein the plurality of biomarkers comprise a DNA-damage biomarker, an inflammatory-response biomarker, a tissue-damage biomarker, a tissue-damage repair biomarker, or a hematology-surrogate biomarker. In a preferred embodiment, the algorithm quantifies an absorbed dose of ionizing radiation in the range of about 1-10 Gy, preferably between about 1-6 Gy, more preferably between about 2-6 Gy, or between about 6-10 Gy.

All or one or more parts of the algorithm(s) and statistical method(s) disclosed herein can be performed by or executed on a processor, general purpose or special purpose or other such machines, integrated circuits or by any combination thereof. Moreover, the software instructions for performing the algorithm(s) and statistical methods(s) disclosed herein may also be stored in whole or in part on a computer-readable medium, i.e., a storage device for use by a computer, processor, general or special purpose or other such machines, integrated circuits or by any combination thereof. A non-limiting list of suitable storage devices includes but is not limited to a computer hard drive, compact disk, transitory propagating signals, a network, or a portable media device to be read by an appropriate drive or via an appropriate connection.

In addition to biomarker measurements, biodosimetry assessment can benefit from additional inputs, such as information regarding clinical symptoms. For example, the Biodosimetry Assessment Tool (BAT) is a software application that equips healthcare providers with diagnostic information (clinical signs and symptoms, physical dosimetry, etc.) relevant to the management of human radiation casualties. Designed primarily for prompt use after a radiation incident, the software application facilitates the collection, integration, and archival of data obtained from exposed persons. Data collected in templates are compared with established radiation dose responses, obtained from the literature, to provide multi-parameter dose assessments. The program archives clinical information (extent of radioactive contamination, wounds, infection, etc.) useful for casualty management, displays relevant diagnostic information in a concise format, and can be used to manage both military and civilian radiation accidents.

Biomarker levels can be measured using any of a number of techniques available to the person of ordinary skill in the art, e.g., direct physical measurements (e.g., mass spectrometry) or binding assays (e.g., immunoassays, agglutination assays and immunochromatographic assays). Biomarkers identified herein can be measured by any suitable immunoassay method, including but not limited to, ELISA, microsphere-based immunoassay methods, lateral flow test strips, antibody based dot blots or western blots. The method can also comprise measuring a signal that results from a chemical reactions, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc. Suitable detection techniques can detect binding events by measuring the participation of labeled binding reagents through the measurement of the labels via their photoluminescence (e.g., via measurement of fluorescence, time-resolved fluorescence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemiluminescence). Alternatively, detection techniques can be used that do not require the use of labels, e.g., techniques based on measuring mass (e.g., surface acoustic wave measurements), refractive index (e.g., surface plasmon resonance measurements), or the inherent luminescence of an analyte.

Binding assays for measuring biomarker levels can use solid phase or homogenous formats. Suitable assay methods include sandwich or competitive binding assays. Examples of sandwich immunoassays are described in U.S. Pat. Nos. 4,168,146 and 4,366,241, both of which are incorporated herein by reference in their entireties. Examples of competitive immunoassays include those disclosed in U.S. Pat. Nos. 4,235,601, 4,442,204 and 5,208,535, each of which are incorporated herein by reference in their entireties.

Multiple biomarkers can be measured using a multiplexed assay format, e.g., multiplexing through the use of binding reagent arrays, multiplexing using spectral discrimination of labels, multiplexing of flow cytometric analysis of binding assays carried out on particles, e.g., using the Luminex® system. Suitable multiplexing methods include array based binding assays using patterned arrays of immobilized antibodies directed against the biomarkers of interest. Various approaches for conducting multiplexed assays have been described (See e.g., US 20040022677; US 20050052646; US 20030207290; US 20030113713; US 20050142033; and US 20040189311, each of which is incorporated herein by reference in their entireties. One approach to multiplexing binding assays involves the use of patterned arrays of binding reagents, e.g., U.S. Pat. Nos. 5,807,522 and 6,110, 426; Delehanty J-B., Printing functional protein microarrays using piezoelectric capillaries, Methods Mol. Bio. (2004) 278: 135-44; Lue R Y et al., Site-specific immobilization of biotinylated proteins for protein microarray analysis, Methods Mol. Biol. (2004) 278: 85-100; Lovett, Toxicogenomics: Toxicologists Brace for Genomics Revolution, Science (2000) 289: 536-537; Berns A, Cancer: Gene expression in diagnosis, nature (2000), 403, 491-92; Walt, Molecular Biology: Bead-based Fiber-Optic Arrays, Science (2000) 287: 451-52 for more details). Another approach involves the use of binding reagents coated on beads that can be individually identified and interrogated. See e.g., WO 9926067, which describes the use of magnetic particles that vary in size to assay multiple analytes; particles belonging to different distinct size ranges are used to assay different analytes. The particles are designed to be distinguished and individually interrogated by flow cytometry. Vignali has described a multiplex binding assay in which 64 different bead sets of microparticles are employed, each having a uniform and distinct proportion of two dyes (Vignali, D. A A, "Multiplexed Particle-Based Flow Cytometric Assays" J. ImmunoL Meth. (2000) 243: 243-55). A similar approach involving a set of 15 different beads of differing size and fluorescence has been disclosed as useful for simultaneous typing of multiple pneumococcal serotypes (Park, M. K et al., "A Latex Bead-Based Flow Cytometric Immunoassay Capable of Simultaneous Typing of Multiple Pneumococcal Serotypes (Multibead Assay)" Clin. Diag. Lab ImmunoL (2000) 7: 4869). Bishop, J E et al. have described a multiplex sandwich assay for simultaneous quantification of six human cytokines (Bishop, L E. et al., "Simultaneous Quantification of Six Human Cytokines in a Single Sample Using Microparticle-based Flow Cytometric Technology," Clin. Chem (1999) 45:1693-1694).

A diagnostic test can be conducted in a single assay chamber, such as a single well of an assay plate or an assay chamber that is an assay chamber of a cartridge. The assay modules, e.g., assay plates or cartridges or multi-well assay plates), methods and apparatuses for conducting assay measurements suitable for the present invention are described for example, in US 20040022677; US 20050052646; US 20050142033; US 20040189311, each of which is incorporated herein by reference in their entireties. Assay plates and plate readers are now commercially available (MULTI-SPOT® and MULTI-ARRAY® plates and SECTOR® instruments, MESO SCALE DISCOVERY,® a division of Meso Scale Diagnostics, LLC, Gaithersburg, Md.).

Reference is made to specific examples illustrating the constructs and methods above. It is to be understood that the examples are provided to illustrate rather than limit the scope of various embodiments of the invention.

EXAMPLES

Methods

Assays. Assays were developed as a number of different singleplex or multiplexed panels in MSD MULTI-ARRAY 96-well plates and analyzed using ECL detection on an MSD plate reader (such as the SECTOR or PR2 lines of plate readers available from Meso Scale Discovery, a division of Meso Scale Diagnostics, LLC, Gaithersburg, Md.). The biomarkers analyzed in the assay panels include the biomarkers listed in Table 1.

Prior to conducting an assay measurement with an assay panel, the sample was first diluted in an appropriate sample diluent to the specified dilution for that panel. The diluted sample (typically about 10 to 25 uL) was then combined with an additional volume of sample diluent (typically one to three times the diluted sample volume) in a well of a MULTI-ARRAY assay plate containing an array of capture antibodies for the targets in the panel. The plate was incubated for about 2 hours with shaking, sample was removed and the wells were washed three times with phosphate buffered saline. A 50-µL volume of a mixture of labeled (MSD SULFO-TAG™ label, an ECL label also available from MESO SCALE DISCOVERY) detection antibodies against the targets in the panel was added and the plate was incubated for about one hour with shaking. The wells were washed three times with phosphate buffered saline and about 125 µL MSD T Read Buffer (available from MESO SCALE DISCOVERY) was added. The plate was read using an MSD ECL plate reader (available from MESO SCALE DISCOVERY). The reader reports assay signals for each array element in relative ECL units.

The same procedure was used for analyzing intracellular markers in blood cell pellets, except that the initial sample was prepared by extracting the blood cell pellet in a histone extraction buffer (50 mM TRIS pH 7.5, 500-mM NaCl, 0.5% NaDeoxycholate, 1% Triton X100, 2-mM EDTA, 1% PhIC, 1% PIC and 1-mM PMSF; 200 µL per $10^6$ white blood cells).

The experimental plate layout contained a negative QC control, a positive QC control and an 8 point calibration curve, all run in duplicate. The calibration curve was fit to a 4 parameter logistic (4-PL) fit using $1/y2$ weighting and used to calculate sample concentrations.

Radiation Dose Studies in Mice. Female mice (strain B6D2F1/J) were subjected to total body irradiation (TBI) at a range of doses (doses in one study included 0, 1.5, 3, 6, 10 Gy and 14 Gy), using a $^{60}$Co γ-ray source, at a dose rate of ~0.6 Gy/min. Mice from these radiation dose levels were sampled at 6 hrs, 1, 2, 3, 5 and 7 days post irradiation (see Table 2). Whole blood was collected at the sampling times and processed into a platelet poor EDTA plasma fraction and peripheral blood leukocyte pellet (PBL). A separate aliquot of whole blood was collected and used to measure blood cell counts. In a given study, typically 6 to 8 mice were tested per dose/time condition. In one study (the "Blinded Study"), the samples covered the conditions shown in Table 3, but were provided for analysis in a blinded fashion to enable an unbiased characterization of the dose-estimation algorithm performance.

Combined Injury Study in Mice. This study examined the effect of a dorsal puncture wound covering 15% of total body surface area on radiation biomarker levels (the wound model is described in Ledney et al. 2010). Female mice (strain B6D2F1/J) exposed to 0 (sham irradiation), 3, 6 or 10 Gy were then subject, within an hour of irradiation, to the 15% surface area puncture wound. Plasma samples were collected at 6 hrs, 1, 2, 3, 5 or 7 days post irradiation. Irradiation conditions and sample collection were as described above for the Biomarker Discovery Study. As non-injury controls, an equal number of mice were subject to the same dose/time conditions and processing as the injured mice, but without receiving the puncture wound. Samples were also collected from true negative control mice, not subject to sham wounding or irradiation procedures. At least 8 replicate mice were subjected to each dose/time/wounding condition. Prior to running the full Combined Injury Study, a smaller Pilot Combined Injury Study was run that was limited to the 0 and 6 Gy dose conditions, and only 6 replicate mice for each dose/time/ injury conditions (see Table 3 and Table 4 for summaries of the test conditions for the Pilot and Full Combined Injury Studies, respectively).

Radiation Dose Testing with NHP Samples. Remnant non-human primate (NHP) samples (Rhesus monkeys—*Macaca mulatta*) from prior radiation studies were evaluated as follows. Remnant Sample Set A included EDTA plasma samples collected pre-irradiation and at various times after TBI irradiation with 0, 1.0, 3.5, 6.5, or 8.5 Gy from a $^{60}$Co γ-ray source and Remnant Sample Set B included EDTA plasma samples collected pre-irradiation and at various times after TBI irradiation with 7.5, 10.0 or 11.5 Gy (6 MV LINAC photon, 0.80 Gy/min). Table 5 summarizes the samples that were tested in feasibility testing. Sample Set A was provided with blood cell counts measured at the time of sample collection.

Human Samples. To measure the expected normal variation in radiation biomarkers, remnant platelet-poor EDTA plasma was collected from individual blood samples donated at blood donation centers (through Bioreclamation, LLC, Liverpool, N.Y.). Samples were collected from 40 normal individuals and up to 10 self-identified individuals for each of four high prevalence chronic diseases (hypertension, diabetes, asthma or rheumatoid arthritis). The samples, summarized in Table 6, were selected to be diverse in sex, age and race.

To evaluate potential new human models for radiation exposure, remnant human samples were collected from radiation oncology patients. EDTA plasma samples were collected from patients receiving standard radiotherapy for lung cancer (15 patients) and GI cancer (8 patients). These treatments involve localized, but relatively large area, irradiation of the affected organ. Typical treatment schedules have patients receiving 1.8 or 2.0 Gy per day, 5 days per week for 6 weeks for a total dose of 54 to 60 Gy. Samples were collected prior to irradiation and at the 3 and 6 week time-points. EDTA plasma was also collected from melanoma patients (13 patients) receiving TBI in preparation for cell-transfer therapy (samples collected before and 6 hours after receiving a 2 Gy dose). All treatments also included chemotherapy. More details on the samples and protocols can be found in Table 7.

TABLE 2

Summary of the test groups, and numbers of mice in each test group, for the Biomarker Discovery Study.

| Test Groups | Sample Collection Time (Post Exposure) | | | | | |
|---|---|---|---|---|---|---|
| Dose (Gy) | 6 h | 1 d | 2 d | 3 d | 5 d | 7 d |
| 0 (Sham) | 8 | 8 | 8 | 8 | 8 | 8 |
| 1.5 | 8 | 8 | 8 | 8 | 8 | 8 |
| 3 | 8 | 8 | 8 | 8 | 8 | 8 |
| 6 | 8 | 8 | 8 | 8 | 8 | 8 |
| 10 | 8 | 8 | 8 | 8 | 10 | 10 |
| 14 | 8 | 8 | 8 | 12 | 16 | 20 |

TABLE 3

Summary of the test groups, and numbers of mice in each test group, for the Combined Injury Study.

| Test Groups | | Sample Collection Time (Post Exposure) | | | | | |
|---|---|---|---|---|---|---|---|
| Dose (Gy) | Injury | 6 h | 1 d | 2 d | 3 d | 5 d | 7 d |
| 0 (Control) | No (Sham) | 6 | 6 | 6 | 6 | 6 | 6 |
| 0 (Control) | Yes | 6 | 6 | 6 | 6 | 6 | 6 |

TABLE 3-continued

Summary of the test groups, and numbers of mice in each test group, for the Combined Injury Study.

| Test Groups Dose (Gy) | Injury | \multicolumn{6}{c}{Sample Collection Time (Post Exposure)} |
|---|---|---|---|---|---|---|---|

| Dose (Gy) | Injury | 6 h | 1 d | 2 d | 3 d | 5 d | 7 d |
|---|---|---|---|---|---|---|---|
| 6 | No (Sham) | 6 | 6 | 6 | 6 | 6 | 6 |
| 6 | Yes | 6 | 6 | 6 | 6 | 6 | 6 |

TABLE 4

Summary of the test groups, and numbers of mice in each test group, for the Full Combined Injury Study. Larger numbers or replicate mice were included at higher doses and times to account for mortality in these groups. Because of the large number of animals the study was broken into two sub-studies that were carried out at different times, each sub-study comprising half the animals for each test condition.

| Test Groups Dose (Gy) | Injury | 6 h | 1 d | 2 d | 3 d | 5 d | 7 d |
|---|---|---|---|---|---|---|---|
| 0 (Control) | No (Control) | 8 | 8 | 8 | 8 | 8 | 8 |
| 0 (Sham) | No (Sham) | 8 | 8 | 8 | 8 | 8 | 8 |
| 0 (Sham) | Yes | 8 | 8 | 8 | 8 | 8 | 8 |
| 3 | No (Sham) | 8 | 8 | 8 | 8 | 8 | 8 |
| 3 | Yes | 8 | 8 | 8 | 8 | 8 | 8 |
| 6 | No (Sham) | 8 | 8 | 8 | 8 | 8 | 8 |
| 6 | Yes | 8 | 8 | 8 | 8 | 12 | 12 |
| 10 | No (Sham) | 8 | 8 | 8 | 8 | 10 | 10 |
| 10 | Yes | 8 | 8 | 8 | 12 | 12 | 12 |

TABLE 5

Summary of the remnant NHP samples analyzed in feasibility testing. Dose/Time Conditions and Number of Replicates Per Condition for NHP Sample Sets A & B Sample Set A ($^{60}$Co γ-ray)

| Time (Days) | \multicolumn{5}{c}{Dose (Gy)} |
|---|---|---|---|---|---|

| Time (Days) | 0.0 | 1.0 | 3.5 | 6.0 | 8.5 |
|---|---|---|---|---|---|
| 0 | 6 | 6 | 6 | 6 | 5 |
| 0.25 | 4 | 4 | 3 | NA | 6 |
| 1 | 5 | 5 | 6 | 6 | 6 |
| 2 | 6 | 6 | 6 | 6 | 6 |
| 3 | 6 | 6 | 6 | 6 | 6 |
| 4 | 6 | 6 | 6 | 6 | 6 |
| 7 | 4 | 6 | NA | 6 | 6 |
| 8 | NA | NA | NA | NA | 1 |
| 9 | 6 | 6 | 6 | 6 | 6 |
| 10 | NA | NA | NA | NA | 5 |

Sample Set B (6 MV LINAC Photon)

| Time | \multicolumn{3}{c}{Dose (Gy)} |
|---|---|---|---|

| Time | 7.5 | 10.0 | 11.5 |
|---|---|---|---|
| 0 | 3 | 4 | 3 |
| 1 | 3 | 4 | 3 |
| 3 | 3 | 4 | 3 |
| 5 | 3 | 4 | 3 |
| 7 | 3 | 4 | 3 |
| 9 | 4 | 4 | 4 |
| 13 | 3 | NA | NA |
| 17 | 3 | NA | NA |
| 21 | 2 | NA | NA |
| 25 | 2 | NA | NA |
| 30 | 2 | NA | NA |

TABLE 6 (a-b)

List of remnant human plasma sample from blood donors used in testing. The sample set included samples from normal individuals, as well as from individuals that self-identified as having one of four high prevalence chronic diseases.

| (a) | \multicolumn{4}{c}{Normal Individuals} |
|---|---|---|---|---|

| | Disease | Gender | Age | Race |
|---|---|---|---|---|
| 1 | N | M | 29 | AA |
| 2 | N | M | 39 | AA |
| 3 | N | M | 52 | AA |
| 4 | N | F | 20 | AA |
| 5 | N | F | 36 | AA |
| 6 | N | M | 39 | AA |
| 7 | N | M | 48 | C |
| 8 | N | M | 61 | C |
| 9 | N | M | 48 | C |
| 10 | N | M | 60 | C |
| 11 | N | M | 49 | C |
| 12 | N | M | 51 | C |
| 13 | N | M | 47 | C |
| 14 | N | M | 37 | C |
| 15 | N | M | 29 | C |
| 16 | N | M | 42 | C |
| 17 | N | M | 49 | C |
| 18 | N | M | 56 | C |
| 19 | N | M | 44 | C |
| 20 | N | M | 29 | C |
| 21 | N | F | 32 | C |
| 22 | N | F | 53 | C |
| 23 | N | F | 39 | C |
| 24 | N | F | 39 | C |
| 25 | N | F | 24 | C |
| 26 | N | F | 48 | C |
| 27 | N | F | 50 | C |
| 28 | N | F | 48 | C |
| 29 | N | F | 39 | C |
| 30 | N | F | 46 | C |
| 31 | N | F | 66 | C |
| 32 | N | F | 22 | C |
| 33 | N | F | 52 | C |
| 34 | N | F | 23 | C |
| 35 | N | M | 52 | H |
| 36 | N | M | 24 | H |
| 37 | N | M | 39 | H |
| 38 | N | M | 46 | H |

TABLE 6 (a-b)-continued

List of remnant human plasma sample from blood donors used in testing. The sample set included samples from normal individuals, as well as from individuals that self-identified as having one of four high prevalence chronic diseases.

| | | | | |
|---|---|---|---|---|
| 39 | N | F | 29 | H |
| 40 | N | F | 48 | H |
| 41 | N | F | 34 | H |
| 42 | N | F | 29 | H |

Individuals with High Prevalence Chronic Diseases

| (b) | Disease | Gender | Age | Race |
|---|---|---|---|---|
| 1 | Hy | M | 43 | C |
| 2 | Hy | M | 73 | C |
| 3 | Hy | M | 65 | C |
| 4 | Hy | F | 56 | C |
| 5 | Hy | M | 53 | AA |
| 6 | Hy | F | 50 | AA |
| 7 | Hy | F | 66 | H |
| 8 | Hy | F | 54 | C |
| 9 | Hy | F | 50 | C |
| 10 | Hy | M | 44 | H |
| 11 | As | M | 75 | C |
| 12 | As | M | 41 | C |
| 13 | As | F | 40 | C |
| 14 | As | F | 21 | C |
| 15 | As | F | 46 | C |
| 16 | As | M | 33 | AA |
| 17 | As | F | 24 | AA |
| 18 | As | M | 45 | H |
| 19 | As | F | 27 | H |
| 20 | As | M | 23 | C |
| 21 | Dia | M | 50 | C |
| 22 | Dia | M | 69 | C |
| 23 | Dia | F | 48 | C |
| 24 | Dia | M | 42 | AA |
| 25 | Dia | F | 57 | AA |
| 26 | Dia | M | 59 | H |
| 27 | Dia | F | 59 | H |
| 28 | Dia | M | 65 | C |
| 29 | Dia | F | 68 | C |
| 30 | RA | F | 47 | AA |
| 31 | RA | M | 59 | C |
| 32 | RA | M | 58 | M |
| 33 | RA | M | 60 | M |
| 34 | RA | M | 59 | C |
| 35 | RA | M | 47 | C |

N = Normal; AA = African American; C = Caucasian; H = Hispanic; Hy = Hypertension
As = Asthma; Dia = Diabetes; RA = Rheumatoid Arthritis

TABLE 7 (a-c)

List of remnant human plasma samples from radiation oncology studies. Brief summaries of the protocols are provided under the tables. (a) Melanoma patients receiving total body irradiation (TBI) prior to cell-transfer therapy were treated with cyclophosphamide and fludarabine 3-5 days prior to TBI (lymphocyte depletion chemotherapy) and plasma was collected pre-TBI and 6 hours after a single 2 Gy fraction. Melanoma patients 15-30 were in the non-TBI arm of the study. (b) Lung cancer patients receiving radiation to the thorax received 2 Gy fractions, 5 days per week, for 6 weeks, as well as neo-adjuvant and/or concurrent 5-FU and taxol. Samples were collected pre-radiation and after total doses of 30 to 60 Gy. (c) GI cancer patients receiving radiation to the GI tracts received 2 Gy fractions, 5 days per week, for 6 weeks, as well as concurrent 5-FU or gemcitabine. Samples were collected pre-radiation and after total doses of 30 and 54 Gy.

(a) Melanoma Patients

| Patient | Pre-Rad | 2 Gy (TBI) |
|---|---|---|
| 1 | X | X |
| 2 | X | X |
| 3 | X | X |
| 4 | X | X |
| 5 | X | |
| 6 | X | |
| 7 | | X |
| 8 | X | |
| 9 | X | |
| 10 | X | X |
| 11 | X | X |
| 12 | X | X |
| 13 | X | X |
| 14 | X | X |
| 15 | X | |
| 16 | X | |
| 17 | X | |
| 18 | X | |
| 19 | X | |
| 20 | X | |
| 21 | X | |
| 22 | X | |
| 23 | X | |
| 24 | X | |
| 25 | X | |
| 26 | X | |
| 27 | X | |
| 28 | X | |
| 29 | X | |
| 30 | X | |
| Total | 29 | 10 |

(b) Lung Cancer Patients

| Patient | Pre-Rad | 30 Gy | 60 Gy |
|---|---|---|---|
| 1 | X | X | X |
| 2 | X | X | X |
| 3 | X | X | X |
| 4 | X | X | X |
| 5 | X | X | X |
| 6 | X | X | X |
| 7 | X | X | X |
| 8 | X | X | X |
| 9 | X | X | X |
| 10 | X | X | X |
| 11 | X | X | X |
| 12 | X | X | X |
| 13 | X | X | X |
| 14 | X | X | X |
| 15 | X | X | X |
| Total | 15 | 15 | 15 |

(c) GI Cancer Patients

| Patient | Pre-Rad | 30 Gy | 54 Gy |
|---|---|---|---|
| 1 | X | X | X |
| 2 | X | X | |
| 3 | X | X | X |
| 4 | X | X | X |
| 5 | | | X |

TABLE 7 (a-c)-continued

List of remnant human plasma samples from radiation oncology studies. Brief summaries of the protocols are provided under the tables. (a) Melanoma patients receiving total body irradiation (TBI) prior to cell-transfer therapy were treated with cyclophosphamide and fludarabine 3-5 days prior to TBI (lymphocyte depletion chemotherapy) and plasma was collected pre-TBI and 6 hours after a single 2 Gy fraction. Melanoma patients 15-30 were in the non-TBI arm of the study. (b) Lung cancer patients receiving radiation to the thorax received 2 Gy fractions, 5 days per week, for 6 weeks, as well as neo-adjuvant and/or concurrent 5-FU and taxol. Samples were collected pre-radiation and after total doses of 30 to 60 Gy. (c) GI cancer patients receiving radiation to the GI tracts received 2 Gy fractions, 5 days per week, for 6 weeks, as well as concurrent 5-FU or gemcitabine. Samples were collected pre-radiation and after total doses of 30 and 54 Gy.

| | | | |
|---|---|---|---|
| 6 | X | X | X |
| 7 | X | X | X |
| 8 | X | X | X |
| Total | 7 | 7 | 7 |

Data Analysis. In evaluating the dose and time responses of individual biomarkers, the significance of differences in observed responses to different test conditions were determined by calculating a p value using a two-tailed unpaired t-test. The measured dose and time responses of the individual biomarkers, as determined in the mouse radiation dose study, were used to develop a multi-parameter algorithm for predicting dose. The basic approach is to model the dose and time response for each biomarker. To predict dose, the biomarker levels of a patient (or animal model) are measured and the dose is calculated that provides the best compromise for fitting each biomarker to its response surface model. In the studies described herein, it is assumed that the time of exposure will be known, so only the dose providing the best compromise fit needs to be calculated.

Results

Mouse Radiation Dose and Combined Injury Studies—Individual Biomarker Responses. The results of biomarker testing for the mouse radiation dose study are shown in FIGS. 1(a)-17(b). Each figure includes a plot of biomarker levels vs. dose for each collection time, and a plot of biomarker levels vs. time for each dose. Each data point for markers in Panels A-D represents the average over 7-8 mice for the control conditions and 10-12 mice for the sham and irradiated conditions, with the exception of the EPO, IL-5, IL10, KC/GRO and TNF-α measurements. The data points for these assays represent the averages are over 3-4 mice for the controls and 6-8 mice for the sham and irradiation conditions. The figures also provide tables of p values indicating the significance in the change in biomarker levels for each condition, relative to the non-irradiated control.

Figures are provided for selected biomarkers showing a significant change ($p<0.05$) over a range of dose/time conditions. The DNA damage and inflammatory markers were early radiation markers, peaking at 6 hrs or 1 day and dropping significantly by 2 days, although there was some evidence that IL-6 and SAA increased at late time points for the higher doses as acute radiation syndrome progressed. The exceptions were IL-5 and IL-12 which showed strong responses at later time points, IL-12 being the only marker that showed a strong dose-dependent decrease in concentration. The biomarkers of tissue-damage repair tended to rise 2 days or more after radiation, although G-CSF had a strong early and late response and Flt-3L showed a significant response at all but the earliest (6 h) time point.

FIGS. 1(a)-17(b) also include a plot of biomarker levels vs. time for each dose and injury condition tested in the Full Combined Injury Study. Focusing on the 0 Gy (non-irradiated) condition and comparing the biomarker levels for non-injured mice (closed circle) and injured mice (open circle), showed that there were a number of biomarkers that were not changed by wounding in the absence of radiation exposure (Flt-3L, GM-CSF, TPO, EPO, IL-5 and CD27). SAA, G-CSF and CD-26 by contrast were significantly elevated ($p<0.05$) by wounding, with the effect of wounding being larger in magnitude than the effect of radiation exposure. IL-12 and CD-45 showed a moderate wounding effect that was statistically significant at some time points, but lower in magnitude than the effect of radiation exposure. The results obtained with the combined injury model are roughly consistent with results using an LPS injection model, described herein, except that GM-CSF and IL-12 levels are strongly elevated in response to LPS, but not affected (GM-CSF) or only weakly affected (IL-12) by wounding.

If the biomarkers were insensitive to wounding in non-irradiated animals, wounding also did not generally affect biomarker levels after radiation exposure. The one exception was TPO; wounding appeared to accelerate the kinetics for the appearance of elevated TPO levels in irradiated animals. The effect was most pronounced for animals receiving a 6 Gy dose. At day 5 post-irradiation the wounded animals had average TPO levels that were almost 5 times higher than non-wounded animals. By day 7, the levels for wounded and non-wounded animals were roughly comparable. We anticipate that use of biomarkers with this type of effect should not affect the ability to identify patients who have been irradiated, but could potentially lead to an overestimation of dose. There is, however, to further improve algorithm accuracy by adjusting the dose assessment algorithm based on information about wounding or other trauma.

Mouse Radiation Dose Study—Algorithm Development and Testing. A multi-parameter algorithm (as described in the Methods section) using 5 biomarkers (Flt-3L, G-CSF, GM-CSF, EPO, IL12/23) was applied to the full sample set from a first mouse radiation dose and time study. For each sample, with its set of biomarker measurements, the predicted dose was calculated using the repeated random sub-sampling approach (see Methods). FIG. 18(a) shows a plot of the predicted dose vs. the actual given dose for the full set of samples. The dashed lines indicate a range of +/−1.5 Gy from 0 to 6 Gy, and indicate +/−25% above 6 Gy. Accounting for the 2.5-fold higher sensitivity of humans to radiation dose relative to the mouse model (LD50/30 for the B6D2F1/J female mouse model is ~9.5 Gy—see, Ledney et al., 2010—vs. ~3-4 Gy for humans), the corresponding human equivalent dose ranges would be +/−0.6 Gy from 0 to 2.4 Gy, and +/−25% above 2.4 Gy.

The ability of the algorithm to correctly classify doses into appropriate ranges can be calculated from FIG. 18(a). The percentage of samples that fall within the defined boundaries in FIG. 18(a) for all doses over the time window of 1-7 days after exposure is 90±3%, where the standard deviation is the variation in the calculated percentage across the different combinations of test and training sets. Note that the accuracy decreases slightly to 88±3% if the time range is expanded to include the 6 hr time point.

Figure 19A:
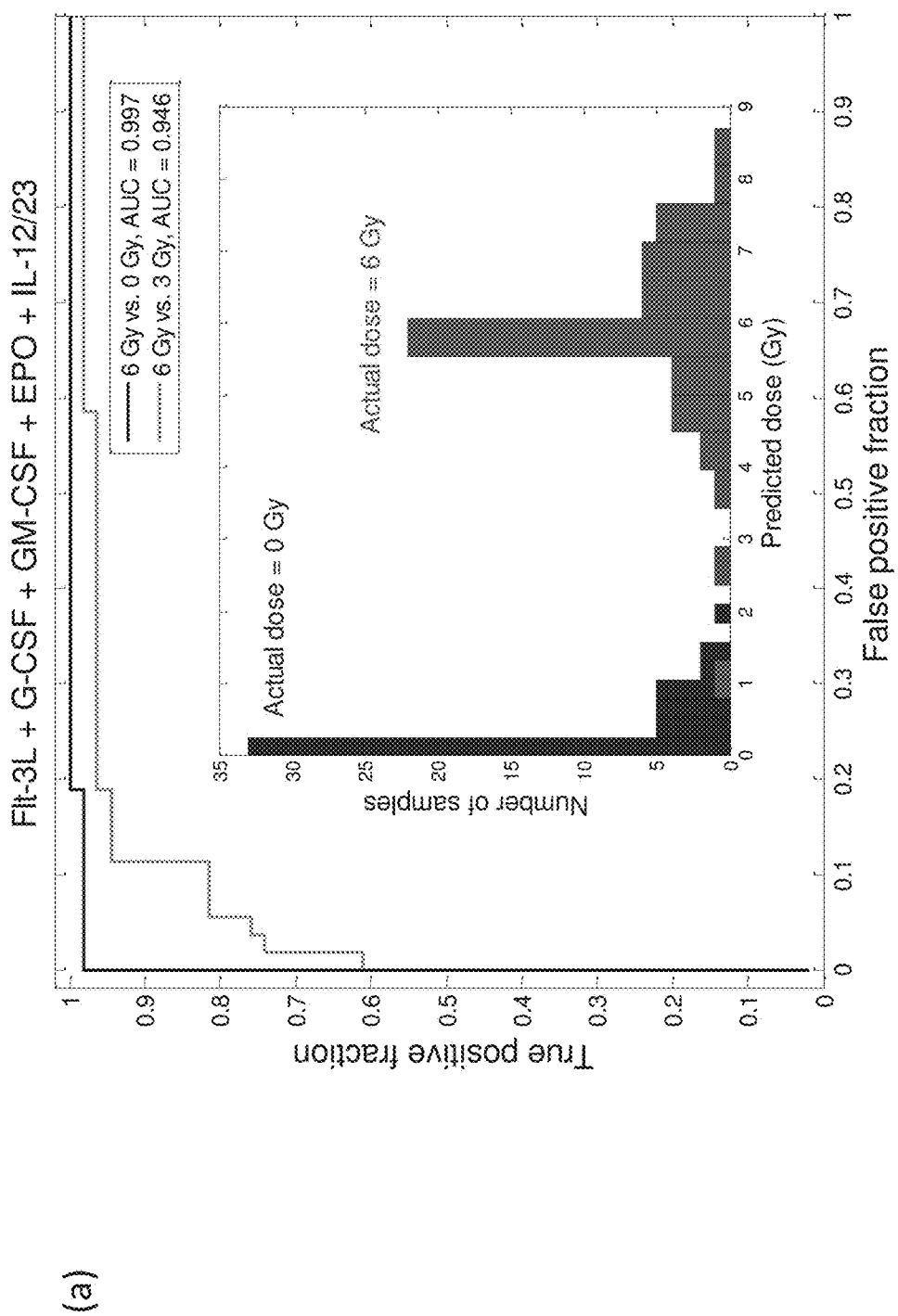
FIGS. 19(a)-(b) are ROC curves for distinguishing 6 Gy doses from non-irradiated controls (blue) and for distinguishing 6 Gy doses from 3 Gy doses. The ROC curves were generated by varying the value of the predicted dose used to classify the samples. The histogram inset shows the distribution of the predicted doses for 6 Gy and non-irradiated sample sets and demonstrates the separation of the two distributions. Panel (a) includes results using the optimal 5 biomarker panel (Flt-3L, G-CSF, GM-CSF, EPO, IL12/23). Panel (b) includes results using a smaller LPS-insensitive panel (Flt-3L, EPO).
Figure 19B:
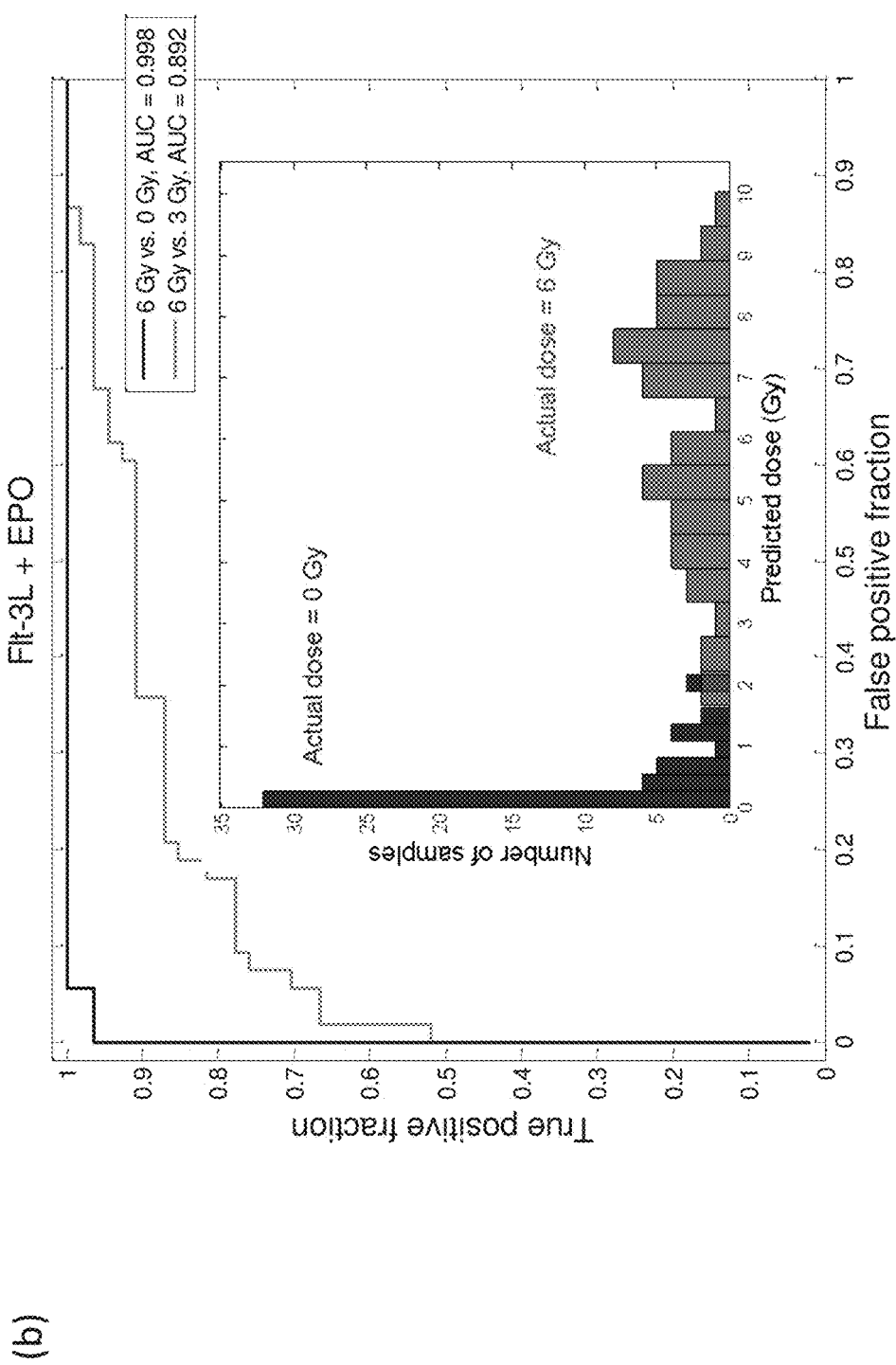

The algorithm was also characterized for its overall ability to discriminate doses of 6 Gy and above from non-irradiated control mice (0 Gy) and to discriminate doses of 6 Gy and above from 3 Gy and below. Given the lower relative survival sensitivity of the mouse model to radiation dose than humans (LD50/30 is roughly 2.5-fold higher for the mouse model), this classification should roughly correspond to the ability to classify dose above or below about 2 to 3 Gy in humans. FIG. 19(a) shows ROC curves generated by varying the predicted dose threshold used to classify the samples. The ROC curves demonstrate excellent classification ability with area under curves (AOCs) of 0.999 for distinguishing 0 Gy from ≥6 Gy and 0.956 for distinguishing ≤3 Gy from ≥6 Gy.

Supplemental Mouse Radiation Dose Study—Algorithm Development and Testing. Algorithm development was advanced using results from a second Mouse Radiation Dose Study. To select optimal biomarker panels for use with our multi-parameter dose-estimation algorithm (as described above), the performance of each possible combination of the 12 most radiation sensitive biomarkers was tested against the Biomarker Discovery Study data set. A repeated random sub-sampling approach was used so that the training and test samples were always independent. Algorithm performance was calculated using two different metrics: (i) a prediction error metric provided as the root mean square error (RMSE) in the predicted doses across the full sample set and (ii) an accuracy metric, where we defined accuracy to be the percentage of samples for which the predicted dose was within +/−1.5 Gy from 0 to 6 Gy, and +/−25% above 6 Gy. Accounting for the 2.5-fold higher sensitivity of humans to radiation dose relative to the mouse model (LD50/30 for the B6D2F1/J female mouse model is ~9.5 Gy—see, Ledney et al., 2010—vs. ~3-4 Gy for humans), the corresponding human equivalent dose ranges would be +/−0.6 Gy from 0 to 2.4 Gy, and +/−25% above 2.4 Gy.

FIGS. 20(a)-(b) shows the RMSE and Accuracy metrics for the different possible biomarkers combinations (each point in the graph represents a different combination of 1 to 12 biomarkers). Focusing on the highest performing combinations for each possible panel size (the top-most points for each panel size), the figure shows that there is no benefit to panel sizes larger than six markers. Table 8 shows the performance metrics for two top performing panels for each panel: the top performing panel including one of the three highly wound-sensitive biomarkers (SAA, G-CSF and CD26) and the top performing panel that does not include any of these three markers. There was no evidence that the injury sensitive markers were required for optimal performance, so the six marker panel without injury sensitive biomarkers (CD27, Flt-3L, GM-CSF, CD45, IL12 and TPO) was selected as the preferred panel for further performance characterization.

TABLE 8

The table shows the preferred biomarker panels identified by applying the multi-parameter dose assessment algorithm to the mouse Biomarker Discovery data set. Two panels are presented for each possible panel size. One panel is the highest performing panel, for a given panel size, that does not include the three most injury sensitive biomarkers as determined by the Combined Injury Study Results: SAA, G-CSF and CD26. The other panel is the highest performing panel that includes one or more of these injury sensitive markers. The accuracy represents the % of samples that were correctly classified by dose (i.e., predicted dose within 1.5 Gy of actual dose for doses ≤6Gy or within 25% of the actual dose for doses >6 Gy). The table also provides the root mean square error (RMSE) in the predicted dose. The six biomarker panel without injury sensitive biomarkers (CD27 + Flt3L + GM-CSF + CD45 + IL-12 + TPO) was chosen for subsequent algorithm validation work.

| # Markers | Panel | Accuracy (%) | RMSE (Gy) |
|---|---|---|---|
| 1 | CD27 | 84.5 ± 3.0 | 1.66 ± 0.16 |
| 1 | Flt-3L | 72.7 ± 3.2 | 2.74 ± 0.20 |
| 2 | CD27 + Flt-3L | 88.9 ± 2.7 | 1.46 ± 0.15 |
| 2 | CD27 + G-CSF* | 88.7 ± 2.5 | 1.48 ± 0.15 |
| 2 | CD27 + GM-CSF | 88.6 ± 2.4 | 1.40 ± 0.14 |
| 3 | CD27 + Flt-3L + GM-CSF | 92.9 ± 2.0 | 1.18 ± 0.12 |
| 3 | CD27 + IL-12 + G-CSF* | 91.9 ± 2.4 | 1.37 ± 0.17 |
| 4 | CD27 + Flt-3L + GM-CSF + CD26* | 93.8 ± 2.0 | 1.13 ± 0.12 |
| 4 | CD27 + Flt-3L + GM-CSF + IL-12 | 93.7 ± 2.0 | 1.16 ± 0.15 |
| 5 | CD27 + Flt-3L + GM-CSF + SAA + CD26* | 94.2 ± 2.3 | 1.09 ± 0.11 |
| 5 | CD27 + Flt-3L + GM-CSF + CD45 + IL-12 | 93.6 ± 2.1 | 1.15 ± 0.14 |
| 6 | CD27 + Flt-3L + GM-CSF + CD45 + SAA + CD26* | 94.7 ± 2.1 | 1.08 ± 0.11 |
| 6 | CD27 + Flt-3L + GM-CSF + CD45 + IL-12 + TPO | 93.7 ± 2.1 | 1.14 ± 0.13 |
| 7 | CD27 + Flt-3L + GM-CSF + CD45 + IL-12 + SAA + CD26* | 94.8 ± 1.9 | 1.06 ± 0.11 |
| 7 | CD27 + Flt-3L + GM-CSF + CD45 + IL-12 + TPO + CD40 | 93.1 ± 2.1 | 1.17 ± 0.13 |
| 8 | CD27 + Flt-3L + GM-CSF + CD45 + IL-12 + SAA + CD26 + G-CSF* | 94.7 ± 2.1 | 1.09 ± 0.12 |
| 8 | CD27 + Flt-3L + GM-CSF + CD45 + IL-12 + TPO + IL-5 + CD40 | 92.3 ± 2.2 | 1.21 ± 0.15 |
| 9 | CD27 + Flt-3L + GM-CSF + CD45 + IL-12 + TPO + IL-5 + SAA + CD26* | 94.4 ± 2.0 | 1.08 ± 0.14 |
| 9 | CD27 + Flt-3L + GM-CSF + CD45 + IL-12 + TPO + IL-5 + CD40 + EPO | 91.4 ± 2.4 | 1.25 ± 0.16 |
| 10 | CD27 + Flt-3L + GM-CSF + CD45 + IL-12 + TPO + CD40 + SAA + CD26 + G-CSF* | 94.0 ± 2.2 | 1.12 ± 0.12 |
| 11 | CD27 + Flt-3L + GM-CSF + CD45 + IL-12 + TPO + IL-5 + CD40 + SAA + CD26 + G-CSF* | 93.6 ± 2.1 | 1.14 ± 0.13 |
| 12 | CD27 + Flt-3L + GM-CSF + CD45 + IL-12 + TPO + IL-5 + CD40 + EPO + SAA + CD26 + G-CSF* | 93.2 ± 2.2 | 1.14 ± 0.14 |

The * and red font indicate the presence of the injury sensitive markers G-CSF, SAA and CD26

Figure 21:
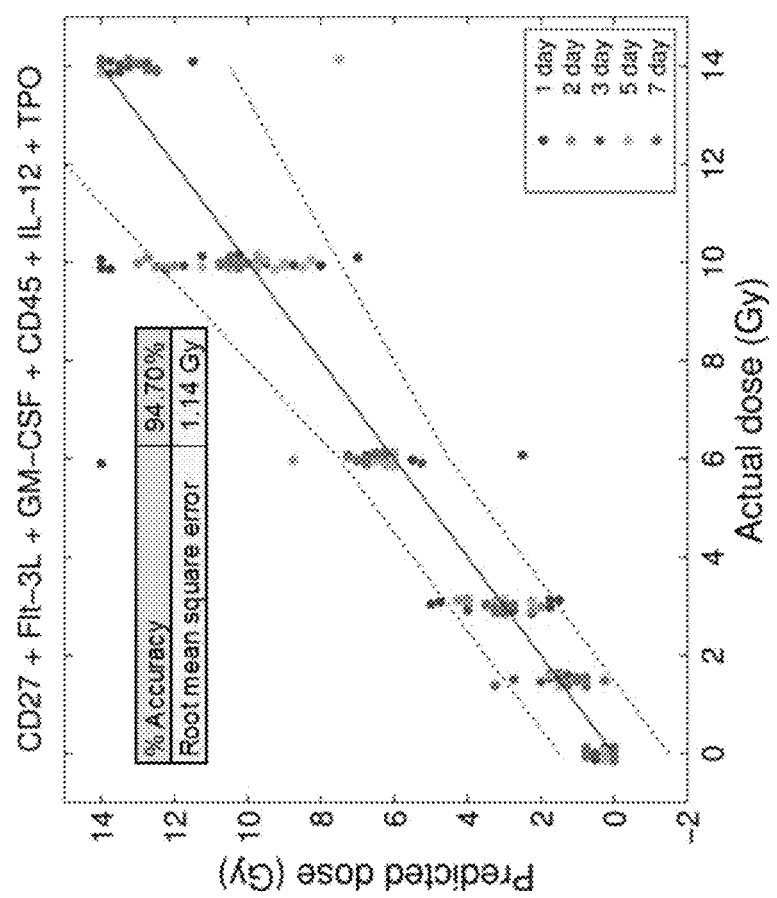
FIG. 21 show the performance of the multi-parameter algorithm and the optimal 6-plex biomarker panel (CD27+Flt-3L+GM-CSF+CD45+IL-12+TPO) for assessing radiation dose in the mouse model. All samples tested in this study were blinded to the individuals conducting the study during testing and dose prediction analysis. The plot shows the predicted dose as a function of actual dose for samples collected between 1 and 7 days after irradiation. The different colors correspond to the time of sample collection. The data are slightly dithered along the X-axis to make the points clearly visible. Points for which the predicted dose exactly matches the actual dose will fall on the solid line. Points within the dashed lines meet our dose prediction accuracy criteria and are within 1.5 Gy of the actual dose (below 6 Gy) or within 25% of the actual dose (above 6 Gy). The inset shows the percentage of the predicted doses that fall within our accuracy criteria and the root mean square error in the predicted doses across the data set.

Performance of Algorithm for Predicting Dose in Blinded Samples. Using the full Biomarker Discovery data set as the training set for the multi-parameter algorithm, the optimal 6-biomarker panel was used to calculate an estimated dose for each sample from the Blinded Study. In this analysis, the sampling time information was available and used in dose estimation, but the actual dose information was blinded to the analysts until the dose estimation was complete. FIG. 21 shows the correlation of the predicted dose and the actual dose and includes dashed lines that represent our Accuracy criteria as described above. Using this approach, 94.7% of the predicted doses fell within our accuracy criteria for all doses over the time window of 1-7 days after exposure. The RMS error in dose estimation was 1.14 Gy (which should be roughly equivalent to +/−0.46 Gy in humans). FIG. 21 also shows that the majority of the points that fell outside of our accuracy criteria were samples collected 1 day after radiation, indicating that there may be opportunities for improving performance by identifying additional early biomarkers or weighting them more heavily.

Figure 22:
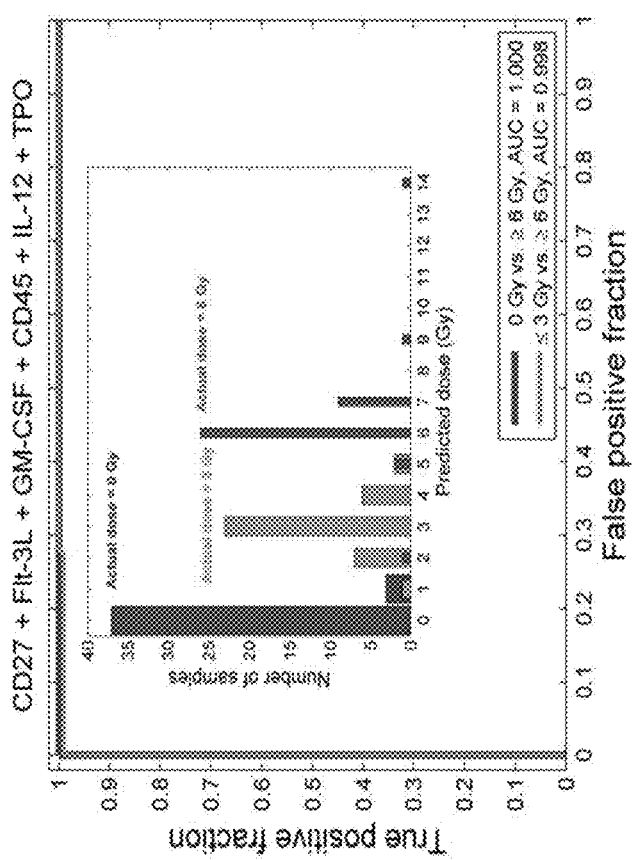
FIG. 22 shows the performance of the multi-parameter algorithm and the optimal 6-plex biomarker panel (CD27+Flt-3L+GM-CSF+CD45+IL-12+TPO) for classifying mouse sample by radiation dose. All samples tested in this study were blinded to the individual conducting the study during testing and dose prediction analysis. The focus of the analysis shown in this plot is the ability of the algorithm to correctly classify samples above or below the critical 2 Gy dose threshold in humans, which is roughly equivalent to 5 Gy in the mouse model. The plot shows ROC curves for distinguishing doses≥6 Gy from non-irradiated controls (blue) and for distinguishing doses≥6 Gy from doses≤3 Gy. The ROC curves were generated by varying the value of the predicted dose used to classify the samples. The histogram inset shows the distribution of the predicted doses for samples receiving 0 Gy, 3 Gy or 6 Gy doses and demonstrates the separation of these distributions. Classification performance at the optimal predicted dose thresholds is provided in the table below the plot.

The algorithm was also characterized for its overall ability to discriminate doses of 6 Gy and above from non-irradiated control mice (0 Gy) and to discriminate doses of 6 Gy and above from 3 Gy and below. Given the lower sensitivity of the mouse model to radiation than humans (LD50/30 is roughly 2.5-fold higher for the mouse model), this classification should roughly correspond to the ability to classify doses around the critical 2 Gy threshold in humans. FIG. 22 shows ROC curves generated by varying the predicted dose threshold used to classify the samples. The ROC curves demonstrate excellent classification ability with area under curves (AOCs) of 1.000 for distinguishing 0 Gy from ≥6 Gy and 0.998 for distinguishing ≤3 Gy from ≥6 Gy. Using the optimal classifications determined by the ROC analysis, there was perfect separation of 0 Gy and ≥6 Gy samples (100% sensitivity, 100% specificity) and near perfect separation of ≤3 Gy and ≥6 Gy samples (99.2% sensitivity and 100% specificity).

Figure 23:
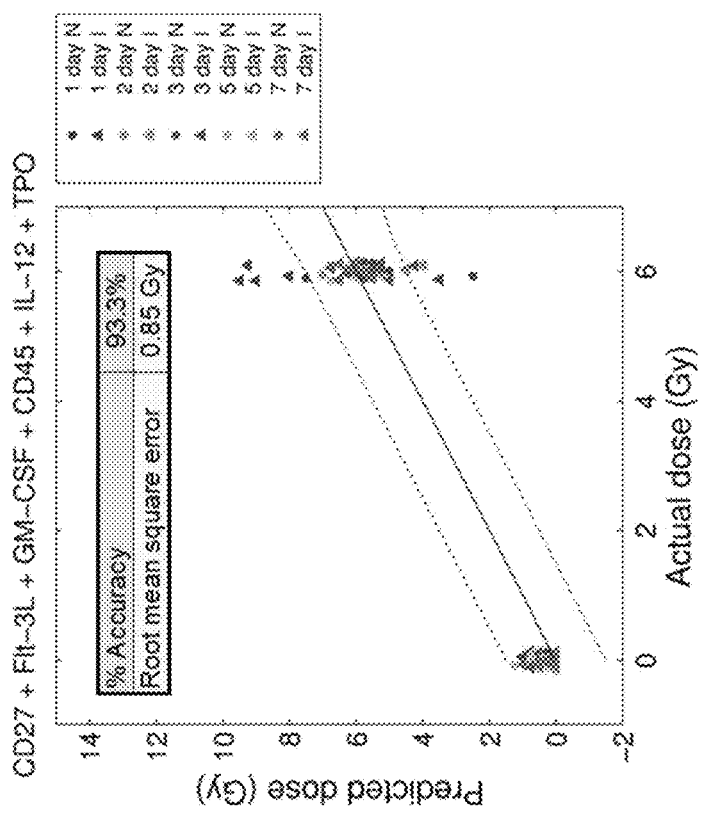
FIG. 23 shows the effect of 15% wound injury on the performance of the multi-parameter algorithm and the optimal 6-plex biomarker panel (CD27+Flt-3L+GM-CSF+CD45+IL-12+TPO) for assessing radiation dose in the mouse model. The sample set included samples from mice receiving 0 Gy or 6 Gy radiations ($^{60}$Co γ-rays) with or without skin wounding (15% surface area puncture wound). Samples were collected at different times up to 7 days after exposure. There were an equal number of replicates for each dose/injury/time condition. The plot shows the predicted dose as a function of actual dose for samples collected between 1 and 7 days after irradiation. The different colors correspond to the time of sample collection. 'Injury' data points are shown as triangles, 'No injury' data points are shown as circles. The data are slightly dithered along the X-axis to make the points clearly visible. Points for which the predicted dose exactly matches the actual dose will fall on the solid line. Points within the dashed lines meet our dose prediction accuracy criteria and are within 1.5 Gy of the actual dose (below 6 Gy) or within 25% of the actual dose (above 6 Gy). The inset shows the percentage of the predicted doses that fall within our accuracy criteria and the root mean square error in the predicted doses across the data set.

Effect of Combined Injury on Algorithm Performance. To provide a preliminary view of the robustness of the algorithm to the potential confounding effects of injury, the algorithm (using the selected optimal 6-biomarker panel) was used to predict dose in the samples from Pilot Combined Injury study (0 and 6 Gy doses, with and without 15% surface wound). FIG. 23 provides a plot of predicted dose vs. actual dose. The percentage of samples that fell within our criteria for dose prediction accuracy was 93.3%, which is roughly in line with the values that that were observed for studies without an injury component (the % accuracy for the blinded study was 94.7%). The RMSE error in dose (0.85 Gy) is lower than the value observed for the blinded study (1.14 Gy), most likely because the blinded study included higher doses. Despite the inclusion of injured animals, it was also possible to set a classification threshold in predicted dose that completely distinguished (100% sensitivity, 100% specificity) the non-irradiated and irradiated animals.

Preliminary Testing of Radiation Biomarkers in NHP Samples. Archived plasma samples from irradiated NHP (Rhesus macaques) were tested with the NHP biomarker assay panels. For almost all dose/time conditions, however, at least 5 of the 6 replicate samples were tested on all assays.

FIGS. 24(a-z) show the radiation dose responses for 13 biomarkers selected for their radiation sensitivity. FIGS. 24(a-z) show that 5 of the 6 biomarkers that were selected for the mouse dose-assessment algorithm were either radiation responsive in NHP (Flt-3L, CD27, TPO, and IL-12) and/or had mechanistic analogs that were radiation responsive in NHP (i.e., the neutrophil surface marker CD177 as an analog for CD45 in mice and the lymphocyte surface marker CD20 as an analog for CD27 in mice). One marker from the mouse panel, GM-CSF, was not detected in control or irradiated NHP; the assay may simply not have sufficient sensitivity for native Rhesus GM-CSF. FIGS. 24(a-z) show that three markers that demonstrated radiation sensitivity in the mouse model (SAA, EPO and G-CSF), but that were not selected for use in the dose-assessment algorithm also responded to radiation in the NHP model. FIGS. 24(a-z) show the response of two markers (CRP and salivary amylase) that are not useful in mice but that have been used to assess radiation exposure in people, and confirms that these biomarkers respond to radiation in the NHP model. Finally, FIGS. 24(a-z) show dose responses for two novel early responders to radiation (TIMP-1 and TNF-RII) that were identified by screening cancer biomarker panels. TIMP-1 (Tissue Inhibitor of MetalloProteinase 1) is regulates a variety of physiological processes through the inhibition of metalloproteases and also has erythroid-potentiating activity. Soluble TNF-RII (soluble TNF receptor II) is released into plasma by proteolytic cleavage of cell bound TNF receptors, and is elevated in a number of inflammatory conditions.

A first pass examination of using the multi-parameter algorithm for dose assessment in the NHP model was carried using a biomarker panel selected to roughly correspond to the preferred mouse panel. The panel included Flt-3L, TPO, IL-12, CD20, CD27, CD177 and salivary amylase. CD20 and CD177 are mechanistically analogous to CD27 and CD45 in the mouse panel. GM-CSF was not included because the NHP GM-CSF assay does not appear to be sensitive enough to detect native GM-CSF in the plasma from normal or irradiated mice. The one marker without an analog in the mouse panel was salivary amylase, which is an established marker in NHP, but is not affected by radiation in mice. The data set gathered from the NHP Sample Set A was analyzed using a slight variation for the algorithm used for the mouse studies, in which the contribution of the different markers was weighted based on their dose responsivity in a specific time range. The algorithm was trained and tested on the data set using the random sub-sampling method to avoid training bias. FIGS. 24(a-z) show the performance of the algorithm for discriminating animals receiving doses of 3.5 Gy and above from non-irradiated control animals (0 Gy) and for discriminating animals receiving doses of 3.5 Gy and above from those receiving 1 Gy and below. Given the lower sensitivity of the NHP model to radiation than humans (LD50/30 is roughly 1.5-fold higher for the mouse model), this classification should roughly correspond to the ability to classify doses around the critical 2 Gy threshold in humans (3 Gy in NHP). FIGS. 25(a)-(b) shows ROC curves generated by varying the predicted dose threshold used to classify the samples. The ROC curves demonstrate excellent classification ability with area under curves (AOCs) of 1.000 for distinguishing 0 Gy from ≥3.5 Gy and 0.995 for distinguishing ≤1 Gy from ≥3.5 Gy. Using the optimal classifications determined by the ROC analysis, there was perfect separation of 0 Gy and ≥3.5 Gy samples (100% sensitivity, 100% specificity) and near perfect separation of ≤1 Gy and ≥3.5 Gy samples (96.9% sensitivity and 98.5% specificity). FIGS. 25(a)-(b) also shows the correlation of predicted dose and actual dose and shows that the correlation is very good near the critical 3 Gy point.

Figure 26:
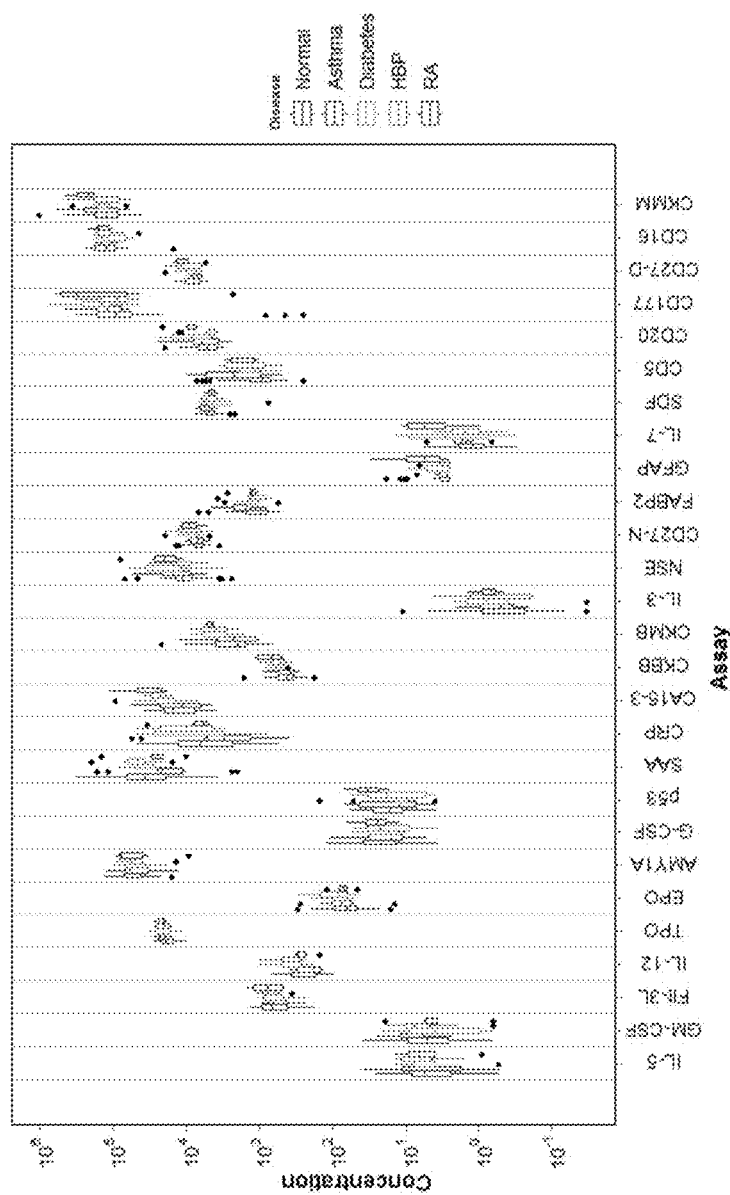
FIG. 26 shows a comparison of biomarker levels in plasma from the normal human population and from individuals having high-prevalence chronic diseases. The data for each group—normal, asthma, high blood pressure (HBP) and rheumatoid arthritis (RA)—are shown in box and whisker format providing the median value (center of the box), the lower and upper quartiles (top and bottom of the box) and 1.5 interquartile ranges (whiskers). Outliers are shown as black points directly above or below the box and whiskers. Concentrations are provided in pg/mL except for SAA and CRP which are in ng/mL.

Human Normal and Diseased Samples. The human biomarker panels were tested with a set of remnant plasma samples from blood donors (Table 6) that included 42 normal healthy individuals as well as samples from donors self-reporting as suffering from one of four high-prevalence chronic diseases: hypertension (10 samples), rheumatoid arthritis (6 samples), asthma (10 samples) and diabetes (9 samples). The results are plotted in bar and whisker format in FIG. 26. There was no evidence that the disease populations were significantly different (p<0.05) than the normal population for any of the biomarkers.

When judging the ability of the mouse model data to support the use of a dose-assessment algorithm in humans, one consideration is whether the increased normal range one would expect for biomarkers in a diverse human population (relative to an inbred mouse strain) would increase the likelihood for false positives. We decided to study this problem by adding random noise to the measured biomarker levels from the non-irradiated mice in the Biomarker Discovery Study, so that the variability in the "normal" mouse levels matched the observed variability in the normal human population. We applied this noise to 4 of the biomarkers in the preferred 6-biomarker panel (Flt-3L, CD27, GM-CSF, and IL-12). CD45 was not measured in the human sample set, so there was no reference for comparison. TPO actually showed lower variation in the human sample set than in the mouse sample set, so the mouse levels were left unchanged.

Figure 27:
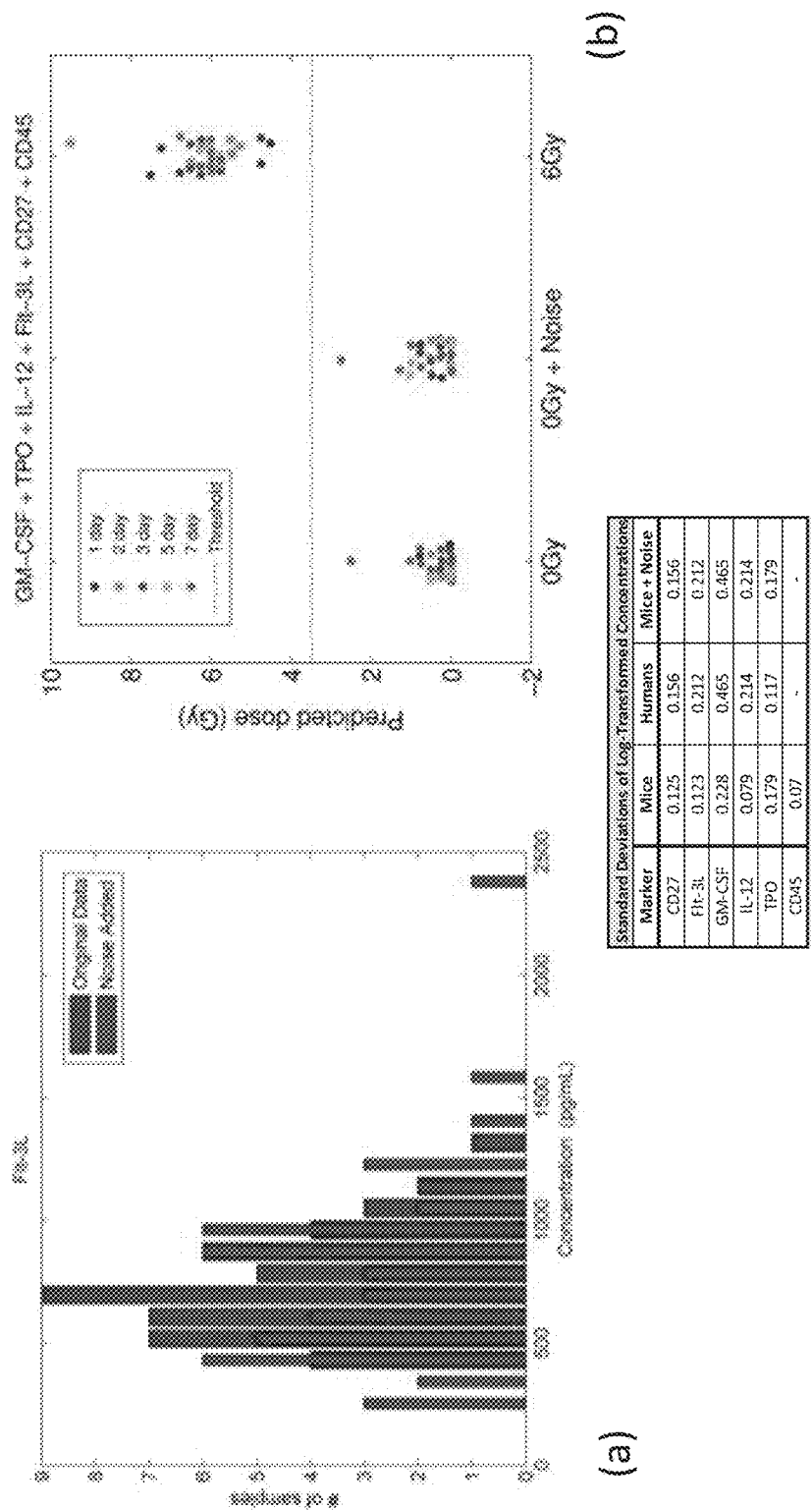
FIGS. 27(a)-(b) shows the results of an effort to model the increased baseline variation in normal humans relative to non-irradiated mice. Random noise was added to the biomarker levels from the non-irradiated mice in the Biomarker Discovery data set so that the observed standard deviations of the data (in log space) matched the observed standard deviation for the analogous markers in the study of normal human levels for the analogous markers measured in the study of normal human levels. Panel A is a histogram comparing the distribution in the baseline levels of one of the biomarkers (Flt-3L), before and after the addition of noise. A table of the observed standard deviations in mice and humans and the standard deviation after noise injection is shown below the plot) Panel B is a scatter plot showing the predicted doses for the 0 Gy samples from the Blinded Study before and after addition of noise. For comparison, the predicted doses for the 6 Gy samples are also shown (with no added noise) as is the optimal threshold selected with the original data for classifying samples as 0 Gy or ≥6 Gy (see FIGS. 27(a)-(b)). The addition of noise did not result in any additional misclassifications and the classification specificity remained at 100%.

The data was then analyzed to determine how the added noise affected the specificity by which non-irradiated control mice could be distinguished from mice exposed to 6 Gy. The classification as 0 Gy or ≥6 Gy was carried out using the optimal threshold selected in the absence of injected noise. As shown in FIGS. 27($a$)-($b$), increasing the baseline biomarker variability did not cause any additional misclassifications and the measured specificity for classification remained at 100%.

Figure 28:
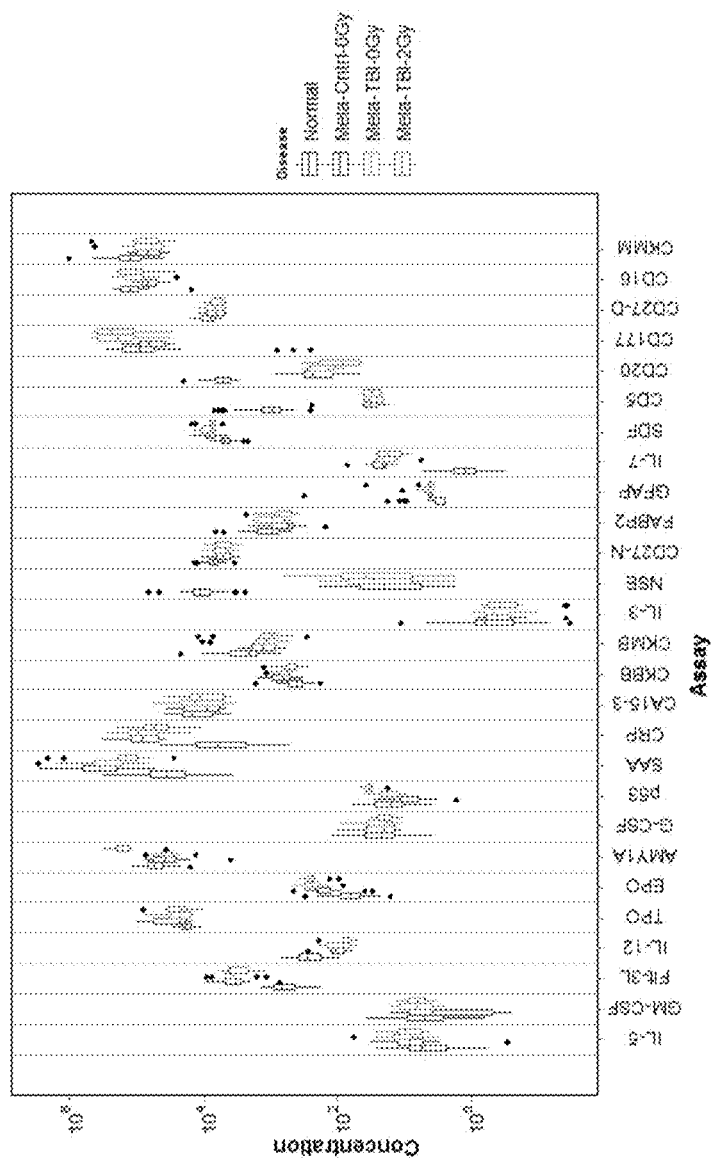
FIG. 28 shows the biomarker levels in plasma from melanoma patients receiving lymphocyte depleting chemotherapy in preparation for cell-transfer therapy. The study had two arms: one set of patients also received TBI 3 days after receiving chemotherapy and the other arm received chemotherapy without TBI. The plot compares biomarker levels in samples from the non-TBI patients (Mela-Cntrl-0 Gy), sample collected from the TBI patients prior to the radiation treatment (Mela-TBI-0 Gy) and samples collected from the TBI patients 5 to 6 hours after receiving a single 2 Gy fraction (Mela-TBI-2 Gy). Biomarker levels from 40 normal blood donors (see FIGS. 27(a)-(b)) are also provided for comparison. Concentrations are provided in pg/mL except for SAA and CRP which are in ng/mL. The levels of AMY1A (salivary amylase) and p53 in the patients receiving the 2 Gy fraction showed significant elevation (p<0.05) relative to levels prior to exposure or levels in the non-TBI control arm of the study.

Human Samples from Patients Receiving Radiation Oncology. Sample sets from cancer patients receiving radiation (Table 7) were evaluated as potential models for assessing biodosimetry algorithms. One set of samples were from melanoma patients receiving lymphocyte depleting chemotherapy prior to cell-transfer therapy. This study included one arm that also received total body irradiation (3 days after chemotherapy) and one arm that did not. Samples were only available pre-irradiation and 5 to 6 hours after the first 2 Gy fraction, so the sample set was relevant for early onset biomarkers. The results shown in FIG. 28 indicate that the biomarker levels in the pre-radiation draws and in patients in the non-TBI arm could be substantially different from the normal range due to the chemotherapy regimen. Nevertheless, two biomarkers showed up as significantly elevated in the post-irradiation group relative to the pre-irradiation group and the non-TBI arm: salivary amylase (p=0.0012), a well-known early onset radiation marker and p53 (p=0.013), a marker identified as an early (<1 day) marker.

Figure 29:
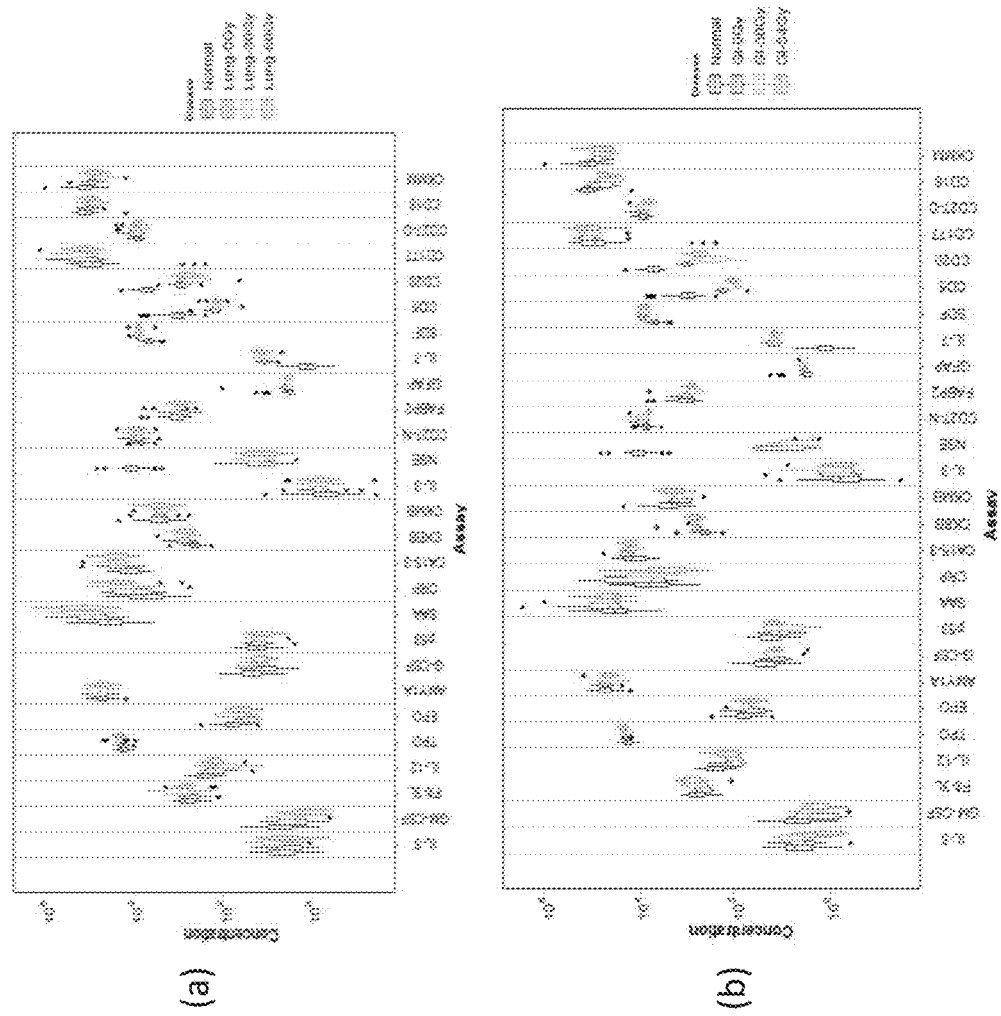
FIGS. 29(a)-(b) show the biomarker levels in plasma from lung cancer patients (top) and GI cancer patients (bottom) receiving localized radiation therapy (2 Gy fractions, 5 fractions per week, 6 weeks). The plot shows biomarker levels prior to radiotherapy and after cumulative doses of 30 Gy and 60 Gy (lung) or 54 Gy (GI). Biomarker levels from 40 normal blood donors (see FIGS. 27(a)-(b)) are also provided for comparison. Concentrations are provided in pg/mL except for SAA and CRP which are in ng/mL.

Samples were also tested from patients receiving localized radiation for lung of GI cancer (2 Gy per day, 5 times per week, 6 weeks), in combination with neo-adjuvant or concurrent chemotherapy. Biomarker levels were measured in samples taken pre-radiation and after cumulative doses of 30 and 54 to 60 Gy (FIGS. 29($a$)-($b$)). Overall, there were no significant observed changes in biomarker levels as a result of these localized radiation therapies. There was evidence for small increases in average levels of hematopoietic markers (Flt-3L and TPO) and small drops in levels of soluble lymphocyte surface markers (CD5 and CD20), but the changes were moderate (~a factor of 2) and there was considerable overlap between the distributions.

Figure 30:
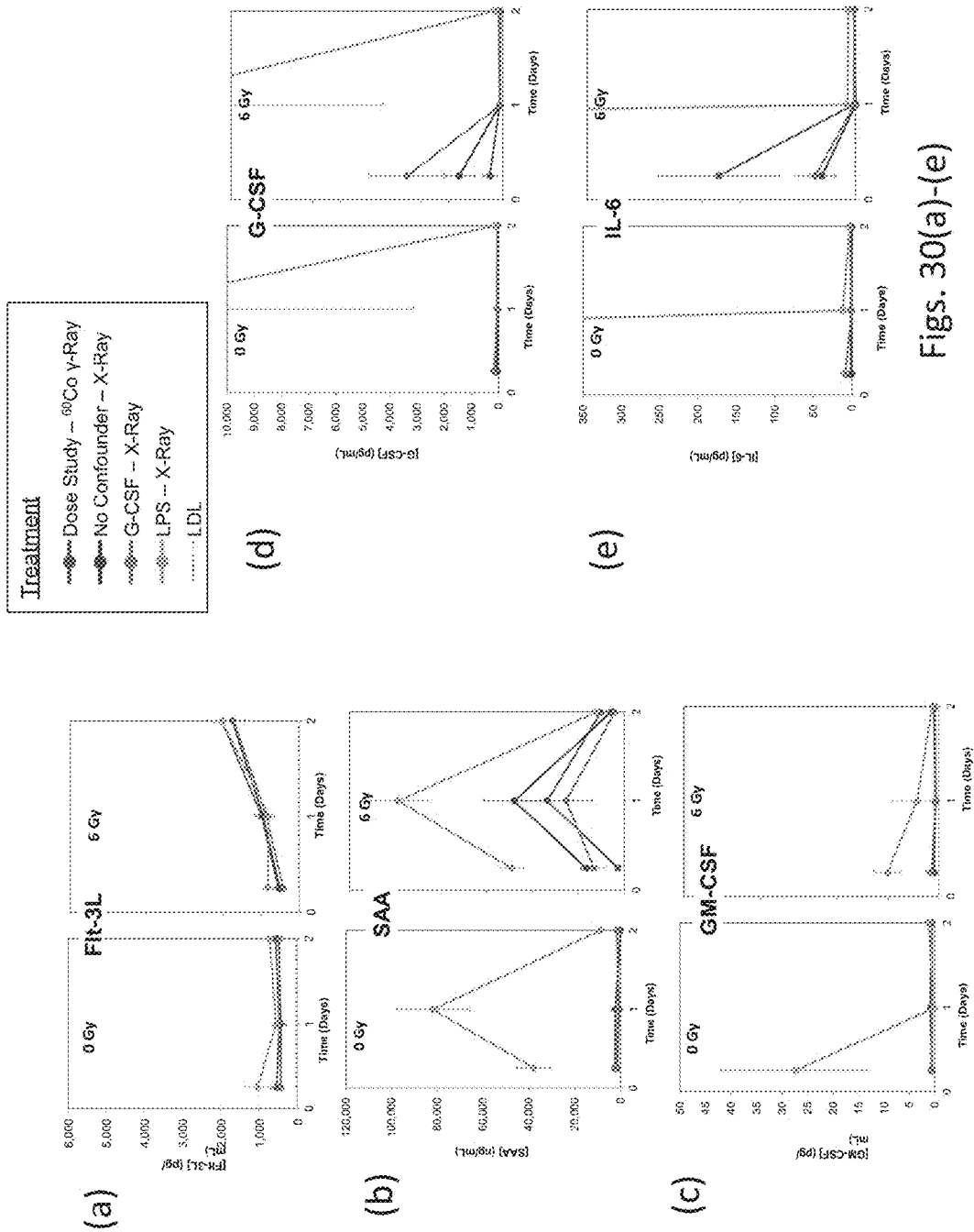
FIGS. 30(a)-(e) show the results of Confounding Effect mouse study for plasma levels of Flt-3L, SAA, G-CSF, GM-CSF and IL-6. The Y-axis is scaled to make the radiation response visible. In some case the LPS response is off-scale. The maximal responses for the different conditions can be viewed in a log scale in the figure. Results for the 0 and 6 Gy conductions from the Radiation Dose Study are plotted side by side for comparison.
Figure 31:
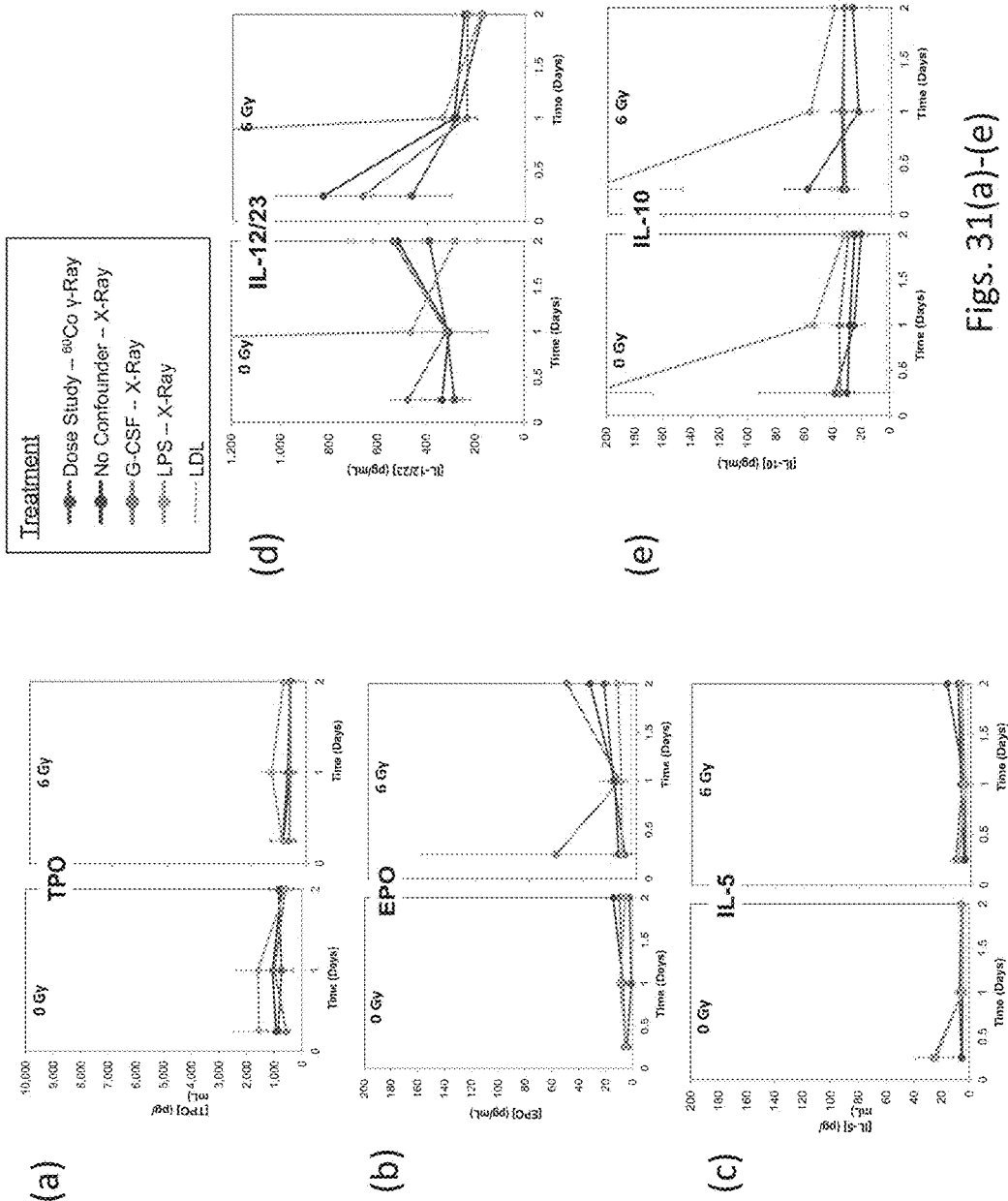
FIGS. 31(a)-(e) show the results of Confounding Effect mouse study for plasma levels of TPO, EPO, IL-12/23, IL-5 and IL-10. The Y-axis is scaled to make the radiation response visible. In some case the LPS response is off-scale. The maximal responses for the different conditions can be viewed in a log scale in figure. Results for the 0 and 6 Gy conductions from the Radiation Dose Study are plotted side by side for comparison.
Figure 32:
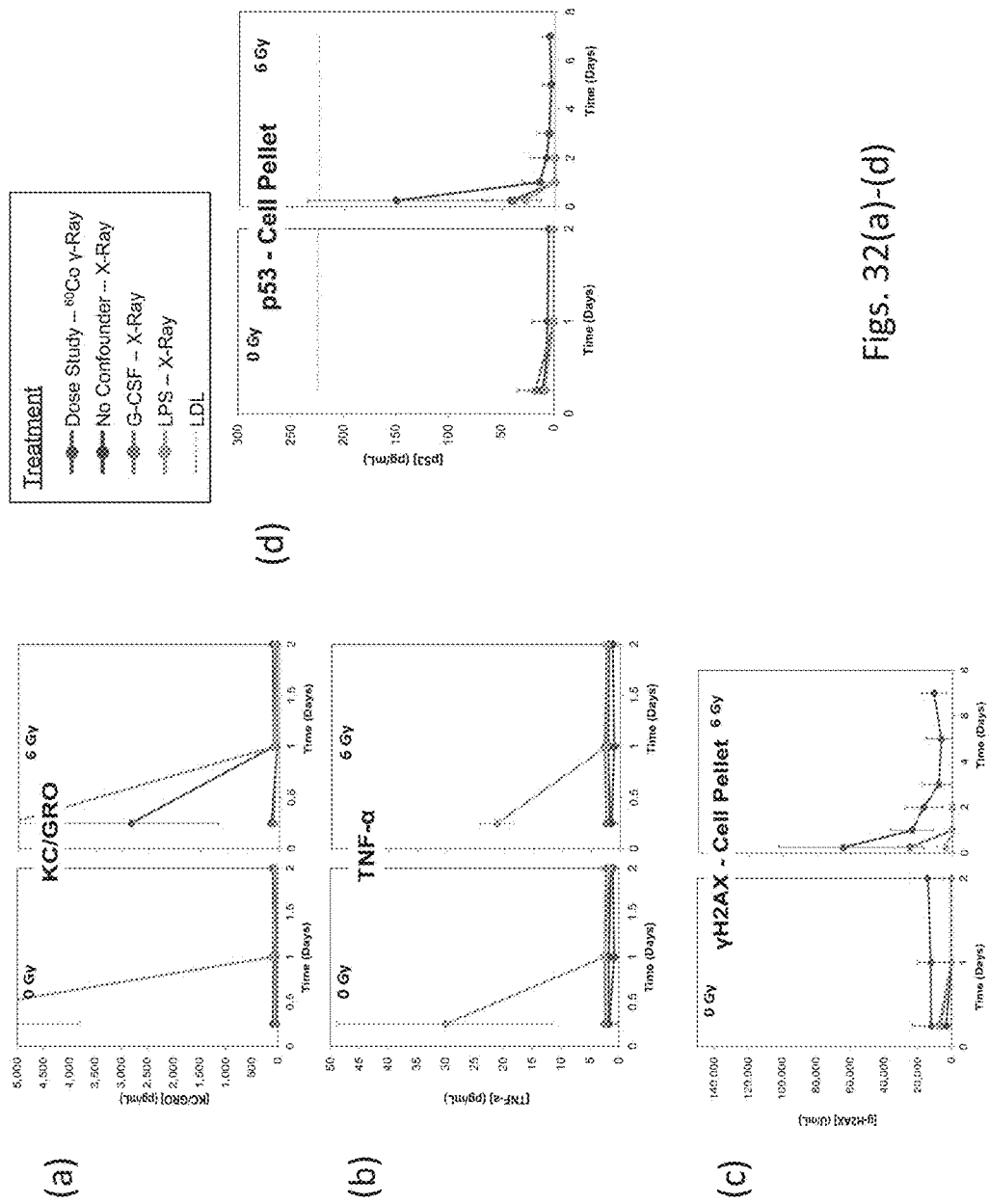
FIGS. 32(a)-(d) show the results of Confounding Effect mouse study for plasma levels of KC/GRO and TNFα and blood cell pellet levels of p53 and γH2AX. The Y-axis is scaled to make the radiation response visible. In some case the LPS response is off-scale. The maximal responses for the different conditions can be viewed in a log scale in the figure. Results for the 0 and 6 Gy conductions from the Radiation Dose Study are plotted side by side for comparison.
Figure 33:
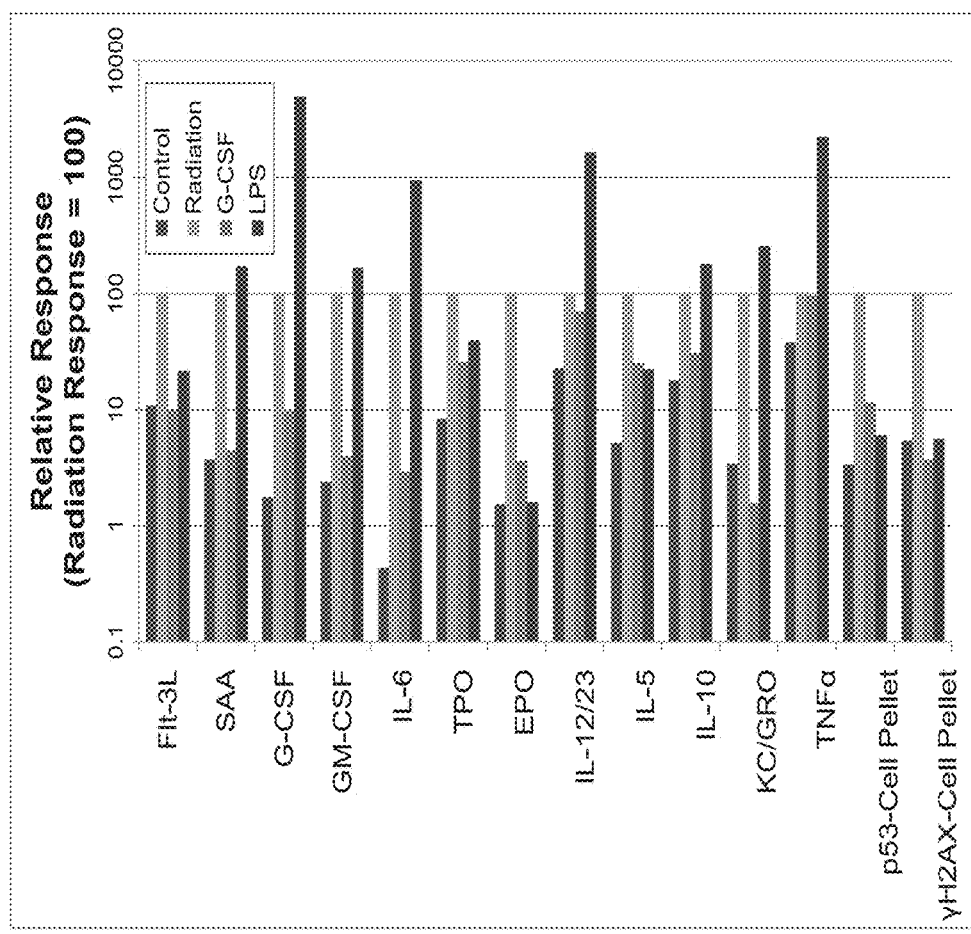
FIG. 33 provides an overview of the Confounding Effect study. For each assay, the bar graph presents the average concentration for the control mice and the average concentration at the conditions that produced the maximal response to G-CSF and LPS over all conditions tested in both the Radiation Dose and Confounding Effect Studies. The signals for each assay are normalized to the maximal radiation response, which is set at 100%.

Mouse Confounding Effect Study—Individual Biomarker Responses. The results of the preliminary mouse confounding effect study are provided in FIGS. 30($a$)-32($d$) for the biomarkers showing radiation sensitivity. The figures provide biomarker levels vs. collection time in the absence of confounding factors or after injection of LPS or G-CSF. Plots are provided for both un-irradiated mice and mice exposed to 6 Gy at 2 hours after treatment with the confounding factor. The preliminary confounding effect study used a different radiation source (X-ray) than the radiation dose-response study (γ-ray), so the 0 and 6 Gy conditions from the radiation dose study are overlaid to gauge consistency of results between the studies. FIG. 33 provides bar graphs showing the relative magnitudes of the maximal observed LPS and G-CSF responses relative to the maximal observed radiation response (including samples from the Radiation Response study) and allows for a rapid assessment of which markers can be subject to confounding effects.

FIG. 33 shows that several assays (SAA, G-CSF, GM-CSF, IL-6, IL-12, IL-12/23 and KC/GRO) showed an LPS response on the same scale or greater than the maximal radiation response. These assays were primarily cytokines or inflammatory-response markers. Flt-3L, EPO, TPO, p53 and γH2AX, in contrast, were insensitive or showed only slight elevations in response to LPS. Interestingly, TNF-α has little or no radiation response but responds strongly to LPS, and can have utility for identifying samples with significant inflammation. Most markers showed no response to G-CSF treatment. Even when a response was observed, for example EPO, the response was relatively small on the scale of the radiation response.

Figure 18B:
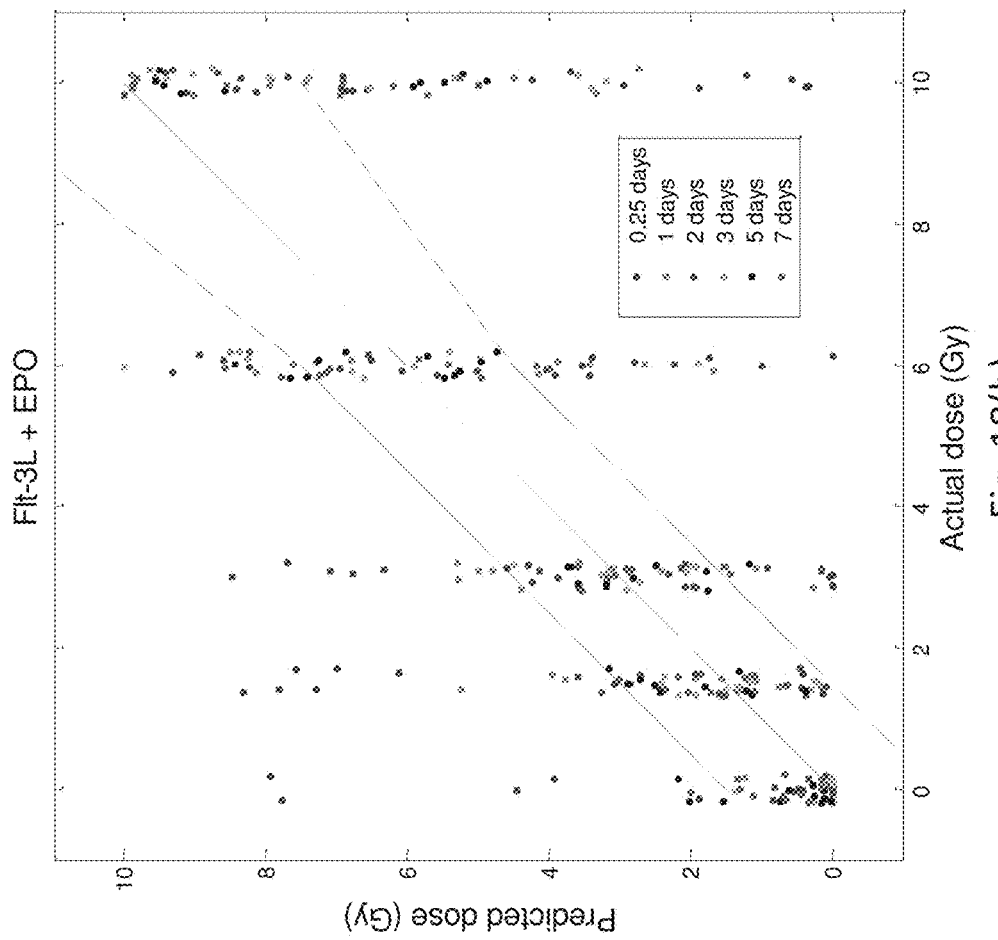

Mouse Confounding Effect Study—Algorithm with Reduced LPS Insensitive Biomarker Set. One approach to address the confounding effects of non-radiation related inflammatory responses is to remove the inflammatory biomarkers from the dose assessment algorithm for patients with obvious trauma or infections. Algorithm performance was characterized after removing the LPS-sensitive biomarkers from the preferred 5 panel biomarker set to produce a 2 biomarker LPS-insensitive panel (Flt-3L and G-CSF). FIGS. 18($b$) and 19($b$) provide plots of predicted dose vs. actual dose and ROC curves for classifying samples with dose≥6 Gy, that were produced analogously to the curves provide in FIGS. 18($a$) and 19($a$) for the full 5 marker panel. The reduced panel was still useful for predicting dose, although there was some degradation in performance relative to the full panel. The accuracy for classifying doses within 1.5 Gy for doses up to 6 Gy or within 25% for doses greater than 6 Gy was 74±4%, compared to 91±3% for the full panel. The AUC for the ROC curve for distinguishing doses≥6 Gy from non-irradiated controls was 0.989, compared to 0.999 for the full panel. The AUC for distinguishing doses≥6 Gy from doses≤6 Gy was 0.882, compared to 0.956 for the full panel.

Figure 34:
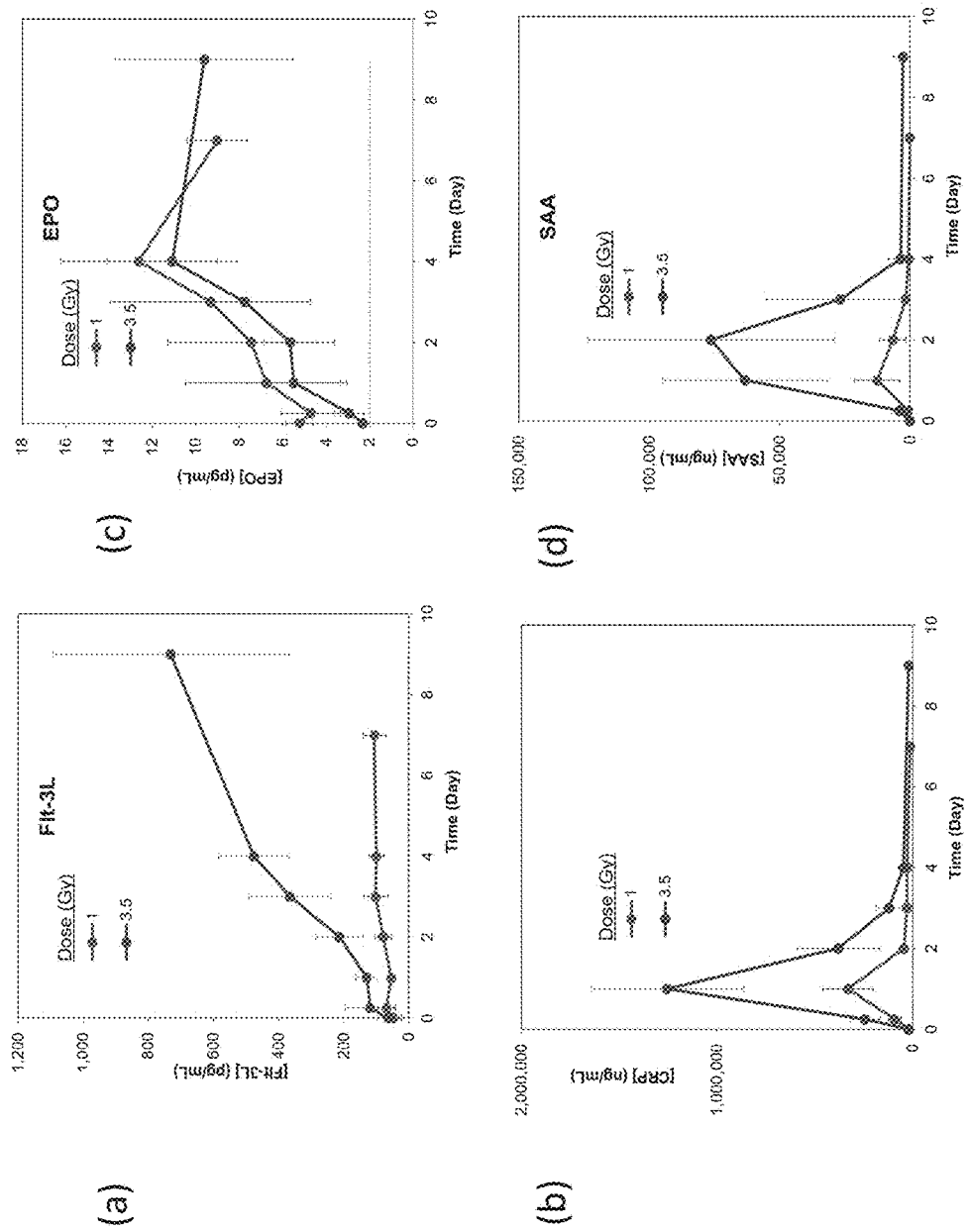
FIGS. 34(a)-(d) show the results of testing of archived plasma samples from irradiated NHPs for Flt-3L, EPO, CRP and SAA. SAA was measured using a commercial ELISA kit. Each point represents the average value for three different animals.
Figure 35:
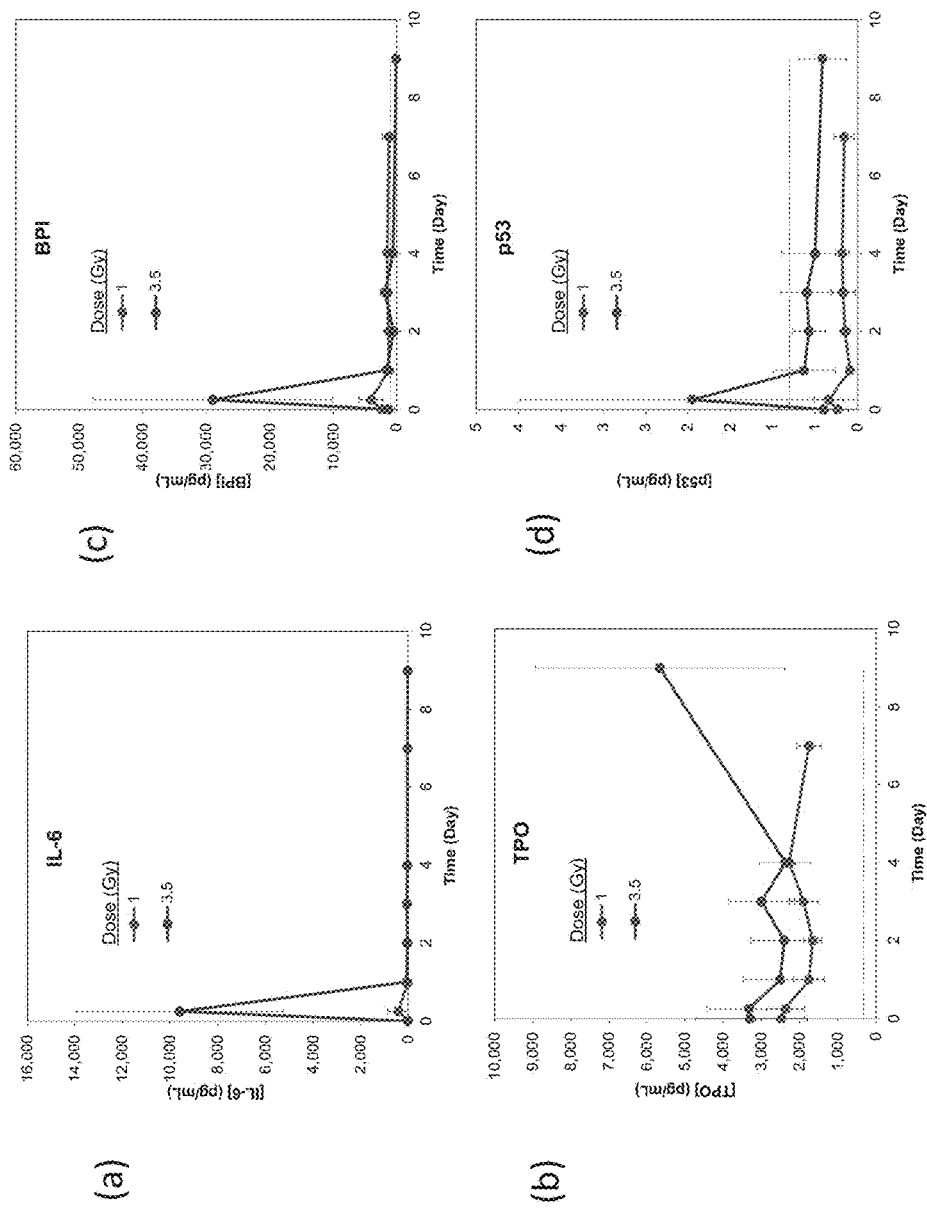
FIGS. 35(a)-(d) show the results of testing of archived plasma samples from irradiated NHPs for IL-6, BPI, TPO and p53. Each point represents the average value for three different animals.

Preliminary Testing of NHP Samples. FIGS. 34($a$)-35($d$) show the results obtained based on preliminary testing of a subset of the Rhesus plasma samples collected between 0 and 9 days after TBI with 1 or 3.5 Gy (3 animals per dose). The results largely confirm those seen with the mouse model; the differences are highlighted below. The NHP model, generally, showed higher radiation sensitivity with stronger responses at 3 Gy and many markers providing good responses at 1 Gy. EPO and SAA responded over a broader time range (1-9 days for EPO, 1-3 days for SAA) than was observed in mice. CRP, while being non-radiation responsive in mice, provided a strong early response in NHP. BPI and p53 were both observed as very early (6 h) markers. GM-CSF did not respond to radiation in the NHP model (data not shown).

Figure 36:
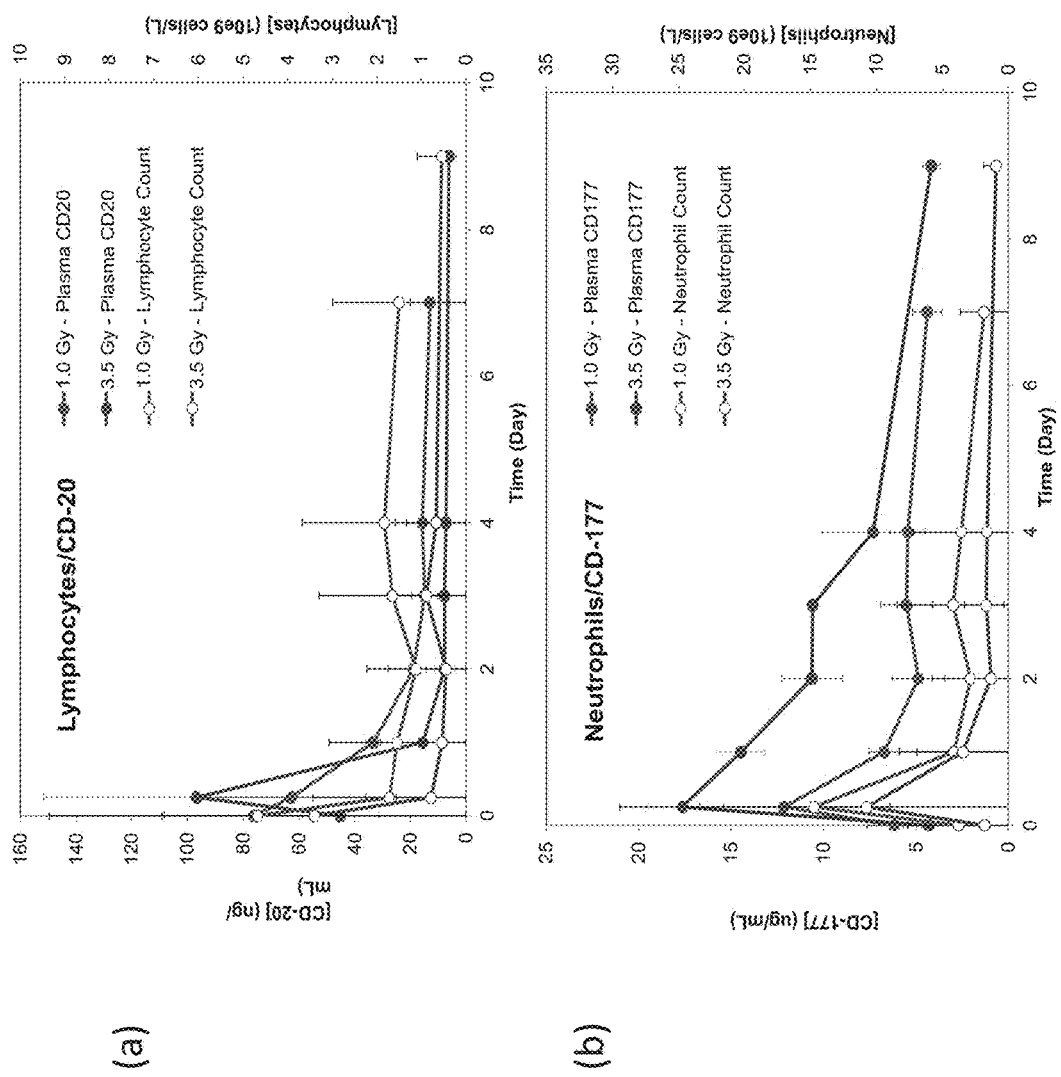
FIGS. 36(a)-(b) show results of testing of archived plasma samples from irradiated NHPs for the lymphocyte cell surface marker CD20 and the neutrophil cell surface marker CD177. The biomarker concentrations for the two tested doses (1.0 and 3.5 Gy) are shown as closed circles with the y-axis scale provided on the left side of the plots. For comparison, lymphocyte and neutrophil cell counts measured on the same animals at the same times are also shown as open circles, with the y-axis scale provided on the right side of the plots. Each point represents the average value for three different animals.

FIGS. 36($a$)-($b$) shows interesting results obtained when the plasma samples were tested with the CD20 (lymphocyte) and CD177 (neutrophil) surrogate markers. Preliminary testing with a small set of archived blood pellet samples collected 0, 1 or 2 days after irradiation showed that the CD20 and CD177 levels showed a similar drop over time as observed by cell counting (data not shown). More interestingly, FIGS. 36($a$)-($b$) shows, for the plasma samples from the 1 and 3.5 Gy cohort, that there are measurable levels of free (not cell-bound) CD-20 and CD-177 in the plasma and that the dose- and time-course changes in the plasma levels of these markers exhibit useful diagnostic information.

Figure 37:
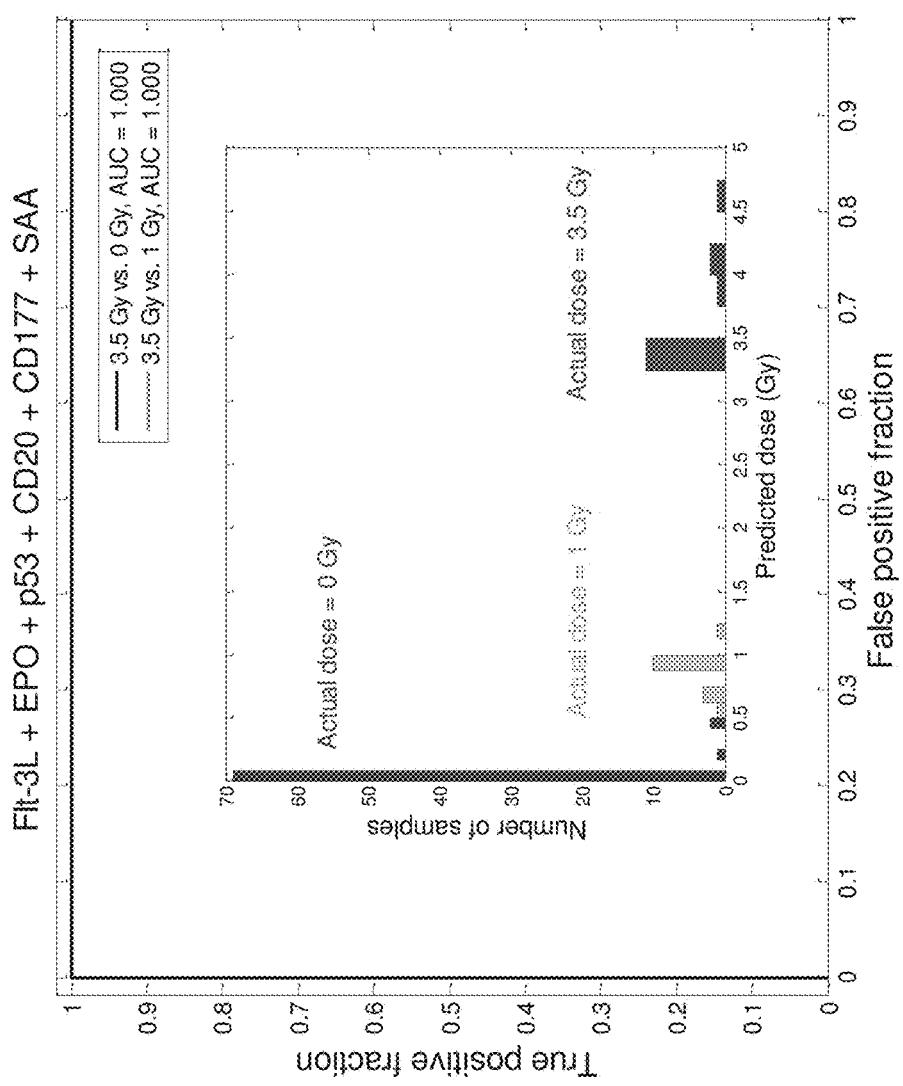
FIG. 37 shows the results from a panel of 6 plasma markers (Flt-3L, EPO, p53, CD20, CD177 and SAA) which provides good discrimination of animals receiving greater than 3.5 Gy (equivalent to ~2 Gy in humans) from those receiving less than 3.5 Gy and also provided high accuracy for semi-quantitative dose prediction.

Additional NHP sample testing and development of dose assessment algorithm for the NHP model. Using data from the NHP model, the approach of assessing radiation dose by fitting multiplexed biomarker data to time-dose response surfaces for each biomarker was evaluated (the same approach described above for the mouse data). The results showed that a panel of 6 plasma markers (Flt-3L, EPO, p53, CD20, CD177 and SAA) can provide good discrimination of animals receiving greater than 3.5 Gy (equivalent to ~2 Gy in humans) from those receiving less than 3.5 Gy and also provided high accuracy for semi-quantitative dose prediction. The results for these 6 biomarkers are shown in Table 26 below and in FIG. 37. Table 26 also illustrates the discrimination utility of additional biomarkers measured in this study.

TABLE 26

| # Markers | Panel | % Accuracy | RMSE (Gy) |
|---|---|---|---|
| 1 | CD20 | 64.8 | 1.51 |
| 1 | SAA | 63.5 | 1.57 |
| 1 | Flt-3L | 69.6 | 1.44 |
| 1 | CD177 | 45.5 | 2.85 |
| 2 | p21 + CD20 | 69.1 | 0.97 |
| 2 | Flt-3L + CD20 | 69.1 | 1.04 |
| 2 | CD20 + CD177 | 66.4 | 1.01 |
| 3 | TPO + p21 + CD20 | 96.5 | 0.73 |
| 3 | Flt-3L + EPO + CD20 | 92.0 | 0.87 |
| 4 | Flt-3L + EPO + CD20 + SAA | 94.2 | 0.58 |
| 4 | Flt-3L + EPO + CD20 + p53 | 94.2 | 0.69 |
| 5 | Flt-3L + EPO + CD20 + CD177 + SAA | 97.1 | 0.44 |
| 5 | Flt-3L + EPO + CD20 + CD177 + CRP | 96.4 | 0.49 |
| 6 | Flt-3L + EPO + CD20 + CD177 + p53 + SAA | 97.5 | 0.35 |
| 7 | Flt-3L + EPO + CD20 + CD177 + CRP + p53 + p21 | 96.5 | 0.41 |
| 8 | Flt-3L + EPO + CD20 + CD177 + CRP + p53 + p21 + TPO | 99.3 | 0.34 |
| 9 | Flt-3L + EPO + CD20 + CD177 + CRP + p53 + p21 + TPO + Amylase | 96.6 | 0.42 |
| 10 | Flt-3L + EPO + CD20 + CD177 + CRP + p53 + p21 + TPO + Amylase + SAA | 97.1 | 0.42 |

The impact of replacing the individual values of CD20 and CD177 in the model with the ratio of CD177/CD20 was evaluated in order to determine if this change would improve the accuracy of the algorithm (analogous to the use of neutrophil/lymphocyte ratio for dose assessment based on hematology results). As shown in Table 27 (a)-(b), the use of the ratio provided roughly equivalent accuracy to the use of the individual values.

TABLE 27 (a)-(b)

| | | X = CD177 + CD20 | | X = CD177/ CD20 | |
|---|---|---|---|---|---|
| # of Markers | Best Panel Including X, When X = CD177 + CD20 | % Correct | RMSE | % Correct | RMSE |
| 2 | X | 88 | 1.17 | 75 | 1.41 |
| 3 | X + SAA | 91 | 1.01 | 86 | 1.41 |
| 4 | X + Flt-3L + CRP | 94 | 0.80 | 89 | 1.16 |
| 5 | X + Flt-3L + EPO + SAA | 97 | 0.44 | 92 | 0.77 |
| 6 | X + Flt-3L + EPO + p53 + SAA | 98 | 0.35 | 94 | 0.51 |
| 7 | X + Flt-3L + EPO + CRP + p53 + p21 | 99 | 0.41 | 94 | 0.49 |
| 8 | X + Flt-3L + EPO + CRP + p53 + p21 + TPO | 99 | 0.34 | 96 | 0.42 |
| 9 | X + Flt-3L + EPO + CRP + p53 + p21 + TPO + Amylase | 99 | 0.42 | 96 | 0.50 |
| 10 | X + Flt-3L + EPO + CRP + p53 + p21 + | 97 | 0.42 | 97 | 0.41 |
| 2 | X | 88 | 1.17 | 75 | 1.41 |
| 3 | X + SAA | 91 | 1.01 | 86 | 1.41 |
| 4 | X + p21 + SAA | 92 | 0.84 | 91 | 1.12 |
| 5 | X + Flt-3L + p21 + SAA | 94 | 0.72 | 93 | 0.77 |
| 6 | X + Flt-3L + CRP + p21 + SAA | 95 | 0.65 | 95 | 0.65 |
| 7 | X + Flt-3L + EPO + CRP + p21 + SAA | 97 | 0.45 | 97 | 0.42 |
| 8 | X + Flt-3L + EPO + CRP + TPO + p53 + SAA | 98 | 0.34 | 98 | 0.34 |
| 9 | X + Flt-3L + EPO + CRP + TPO + p21 + p53 + SAA | 97 | 0.40 | 97 | 0.37 |
| 10 | X + Flt-3L + EPO + CRP + TPO + p21 + p53 + SAA + Amylase | 97 | 0.42 | 97 | 0.41 |

Alternate algorithms for dose assessment were also evaluated. A simple linear model (Dose=$A_1C_1+A_2C_2+A_3C_3+\ldots$, where Ci is the concentration of marker i and Ai is an empirically determined coefficient) was equivalent to the response surface based model for distinguishing animals exposed to 0 and 3.5 Gy (both models were able to correctly classify all samples from animals in these two groups). The linear model has the advantage of not requiring knowledge of the time between exposure and sample collection, but does not quantify dose as well as the response surface model (root mean square error for dose assessment for the optimal panel was ~1 Gy vs. ~0.3 Gy for the response surface model).

* * *

Various publications and test methods are cited herein, the disclosures of which are incorporated herein by reference in their entireties, In cases where the present specification and a document incorporated by reference and/or referred to herein include conflicting disclosure, and/or inconsistent use of terminology, and/or the incorporated/referenced documents use or define terms differently than they are used or defined in the present specification, the present specification shall control.

REFERENCES

1. Baranov A E, Guskova A K, Nadejina N M, Nugis V Y. (1995). Chernobyl experience: biological indicators of exposure to ionizing radiation. Stem Cells. 13(Suppl 1): 69-77.
2. Bertho J M, Roy L. (2009) A rapid multiparametric method for victim triage in cases of accidental protracted irradiation or delayed analysis. Br J Radiol. August; 82(981):764-70.

3. Bertho J M, Roy L, Souidi M, Benderitter M, Bey E, Racine R, Fagot T, Gourmelon P. (2009) Initial evaluation and follow-up of acute radiation syndrome in two patients from the Dakar accident. Biomarkers. March; 14(2):94-102.
4. Bertho J-M, Demarquay C, Frick J, Joubert C, Arenales S, Jacquet N, Sorokine-Durm I, Quang Chau, Lopez M, Aigueperse J, Gorin N-C, Gourmelon P. (2001). Level of Flt3-ligand in plasma: a possible new bio-indicator for radiation-induced aplasia. Int. J. Radiat. Biol. 77(6): 703-712.
5. Blakely W F, Ossetrova N I, Whitnall M H, Sandgren D J, Krivokrysenko V I, Shakhov A, Feinstein E. (2010) Multiple parameter radiation injury assessment using a nonhuman primate radiation model-biodosimetry applications. Health Phys. February; 98(2):153-9.
6. Dainiak N, Waselenko J K, Armitage J O, MacVittie T J, Farese A M. (2003) The hematologist and radiation casualties. Hematology Am Soc Hematol Educ Program.:473-96. Review.
7. Dainiak, N. (2002). Hematologic consequences of exposure to ionizing radiation. Exp. Hematol. 30, 513-28.
8. Fliedner T M, Friesecke I., and Beyrer K. (2001). Medical management of radiation accidents. Manual on the acute radiation syndrome. The British Institute of Radiology, London, United Kingdom.
9. Goans, R. E., Holloway, E. C., Berger, M. E., Ricks, R. C. (1997). Early dose assessment following severe radiation accidents, Health Phys. 72(4), 513-18.
10. Huchet A, Belkacemi Y, Frick J, Prat M, Muresan-Kloos I, Altan D, Chapel A, Gorin N C, Gourmelon P, Bertho J M. (2003) Plasma Flt-3 ligand concentration correlated with radiation-induced bone marrow damage during local fractionated radiotherapy. Int J Radiat Oncol Biol Phys. October 1; 57(2):508-15.
11. Ledney G. D. and Elliot T. B. (2010). Combined injury: factors with potential to impact radiation dose assessments. Health Physics 98: 145-152.
12. Kabacik S, Mackay A, Tamber N, Manning G, Finnon P, Paillier F, Ashworth A, Bouffler S, Badie C. (2011) Gene expression following ionising radiation: identification of biomarkers for dose estimation and prediction of individual response. Int J Radiat Biol. February; 87(2):115-29.
13. Koc M., Taysi S., Sezen O., Bakan N. (2003). Levels of some acute-phase proteins in the serum of patients with cancer during radiotherapy. Biology Pharmaceutical Bulletin 26(10):1494-1497.
14. MacVittie T J, Monroy R L, Patchen M L, Souza L M. (1990): Therapeutic use of recombinant human G-CSF in a canine model of sublethal and lethal whole-body irradiation. Int J Radiat Biol 57:723.
15. Mal'tsev V N, Strel'nikov V A, and Ivanov A A. (1978). C-reactive protein in the blood serum as an indicator of the severity of radiation lesion. Doklady Akademii Nauk SSR 239(3):750-2.
16. Mal'tsev V N, Ivanov A A, Mikhailov V F, Mazurik V K. (2006) [The individual prognosis of the gravity and of the outcome of acute radiation disease based on immunological indexes]. Radiats Biol Radioecol. March-April; 46(2):152-8.
17. Metcalf D. (1985) The granulocyte-macrophage colony-stimulating factors. Science, 229:16-22.
18. Monroy R L, Skelly R R, MacVittie T J, Davis T A, Sauber J J, Clark S C, Donahue R E. (1987) The effect of recombinant GM-CSF on the recovery of monkeys transplanted with autologous bone marrow. Blood 70:1696.
19. Mouthon M A, Vandamme M, Gourmelon P, Vainchenker W, Wendling F. (1999) Preferential liver irradiation enhances hematopoiesis through a thrombopoietin-independent mechanism. Radiat Res. October; 152(4):390-7.
20. Ossetrova N I, Sandgren D J, Gallego S, Blakely W F. (2010) Combined approach of hematological biomarkers and plasma protein SAA for improvement of radiation dose assessment triage in biodosimetry applications. Health Phys. February; 98(2):204-8.
21. Ossetrova N I, Farese A M, MacVittie T J, Manglapus G L, Blakely W F. (2007). The use of discriminant analysis for evaluation of early-response multiple biomarkers of radiation exposure using non-human primate 6-Gy whole-body radiation model. Radiation Measurements 42(6-7): 1158-1163.
22. Ossetrova N I, Blakely W F. Multiple blood-proteins approach for early-response exposure assessment using an in vivo murine radiation model. International Journal of Radiation Biology. 2009. 85(10): 837-850.
23. Ossetrova N I, Sandgren D J, Blakely W F. C-reactive Protein and Serum Amyloid A as Early-phase and Prognostic Indicators of Acute Radiation Exposure in Nonhuman Primate Total-body Irradiation Model. Radiation Measurements. 2011. 46:1019-1024.
24. Redon C E, Nakamura A J, Martin O A, Parekh P R, Weyemi U S, Bonner W M. (2011) Recent developments in the use of γ-H2AX as a quantitative DNA double-strand break biomarker. Aging (Albany N.Y.). February; 3(2):168-74.
25. Redon C E, Nakamura A J, Gouliaeva K, Rahman A, Blakely W F, Bonner W M. The use of gamma-H2AX as a biodosimeter for total-body radiation exposure in non-human primates. (2010) PLoS One. November 23; 5(11):e15544.
26. Rothkamm K, Horn S. (2009) gamma-H2AX as protein biomarker for radiation exposure. Ann Ist Super Sanita. 45(3):265-71.
27. Taneja N, Davis M, Choy J S, Beckett M A, Singh R, Kron S J, Weichselbaum R R. (2004) Histone H2AX phosphorylation as a predictor of radiosensitivity and target for radiotherapy. Journal of Biological Chemistry 279:2273-2280.
28. Tukachinski S. E. and Moiseeva V. P. (1961). Cx-reactive protein in radiation injury. Bulletin of Experimental Biology and Medicine, 52:48-52.
29. Welte K, Bonilla M A, Gillio A P, Boone T C, Potter G K, Gabrilove J L, Moore M A S, OReilly R J, Souza L M. (1987) Recombinant human granulocyte colony-stimulating factor. Effects on hemopoiesis in normal and cyclophosphamide-treated primates. J Exp Med 165:941.
30. Wilson J W, Pritchard D M, Hickman J A, Potten C S. (1998) Radiation-induced p53 and p21WAF-1/CIP1 expression in the murine intestinal epithelium: apoptosis and cell cycle arrest. Am J Pathol. September; 153(3):899-909.
31. WO 2008/140463; Blakely, et al., "Biomarker Panels for Assessing Radiation Injury and Exposure."

What is claimed is:

1. A method of assessing an absorbed dose of ionizing radiation in a plasma or blood sample from a patient, said method comprising (a) measuring the level of each of at least six markers in said sample, wherein said at least six markers comprise CD20, Flt-3L, CD177, AMY, IL-12, and TPO;

(b) applying, by a processor, an algorithm to assess said absorbed dose in said patient as being above or below a 2 Gray (Gy) threshold based on said level of each of said at least six markers in said sample over time with a sensitivity of 96.9% or higher and a specificity of 98.5% or higher;

(c) grouping the patient into one of two groups, a first group being a group having an assessed absorbed dose below the threshold of 2 Gy, a second group being a group having an assessed absorbed dose above the threshold of 2 Gy; and (d) administering a medical countermeasure to the patient if the patient is grouped in the second group.

2. The method of claim 1 wherein said algorithm quantifies an absorbed dose of ionizing radiation in the range of about 1-10 Gy.

3. The method of claim 1 wherein the sample comprises plasma.

4. The method of claim 1, wherein the sample comprises blood.

5. The method of claim 1, wherein said levels of said at least six markers are measured using an immunoassay.

6. The method of claim 5, wherein the immunoassay is conducted in a multi-well assay plate or in a cartridge.

7. The method of claim 6, wherein the immunoassay is conducted in the cartridge.

* * * * *